United States Patent
Yampol'skiy

(10) Patent No.: US 11,913,033 B2
(45) Date of Patent: Feb. 27, 2024

(54) LUCIFERASES AND METHODS FOR USING SAME

(71) Applicant: LIGHT BIO, INC., Mount Horeb, WI (US)

(72) Inventor: Il'ya Viktorovich Yampol'skiy, Moscow (RU)

(73) Assignee: Light Bio, Inc., Ketchum, ID (US)

( * ) Notice: Subject to any disclaimer, the term of this patent is extended or adjusted under 35 U.S.C. 154(b) by 758 days.

(21) Appl. No.: 16/479,693

(22) PCT Filed: Dec. 6, 2017

(86) PCT No.: PCT/RU2017/050125
§ 371 (c)(1),
(2) Date: Jul. 22, 2019

(87) PCT Pub. No.: WO2018/139956
PCT Pub. Date: Aug. 2, 2018

(65) Prior Publication Data
US 2021/0079363 A1    Mar. 18, 2021

(30) Foreign Application Priority Data
Jan. 30, 2017  (RU) .......................... RU2017102986

(51) Int. Cl.
| | | |
|---|---|---|
| *C12N 15/52* | (2006.01) | |
| *C12N 15/62* | (2006.01) | |
| *C12N 9/02* | (2006.01) | |
| *C12N 15/10* | (2006.01) | |
| *G01N 33/535* | (2006.01) | |

(52) U.S. Cl.
CPC ....... *C12N 9/0069* (2013.01); *C12N 15/1096* (2013.01); *C12N 15/52* (2013.01); *C12N 15/625* (2013.01); *G01N 33/535* (2013.01)

(58) Field of Classification Search
CPC ..................................................... G01N 33/53
See application file for complete search history.

(56) References Cited

U.S. PATENT DOCUMENTS

| | | |
|---|---|---|
| 5,484,956 A | 1/1996 | Lundquist et al. |
| 5,538,879 A | 7/1996 | Muller-Rober et al. |
| 5,576,198 A | 11/1996 | McBride et al. |
| 5,595,896 A | 1/1997 | Coruzzi et al. |
| 5,629,470 A | 5/1997 | Lam et al. |
| 5,633,155 A | 5/1997 | Kim et al. |
| 5,656,666 A | 8/1997 | Yu et al. |
| 5,674,731 A | 10/1997 | Lin et al. |
| 5,689,049 A | 11/1997 | Cigan et al. |
| 5,690,045 A | 11/1997 | Gauthier |
| 5,739,409 A | 4/1998 | Fischer et al. |
| 5,750,870 A | 5/1998 | Mathews et al. |
| 5,767,367 A | 6/1998 | Dudits et al. |
| 2002/0192755 A1* | 12/2002 | Francis .................. C12N 15/74 435/69.1 |
| 2005/0081268 A1* | 4/2005 | Kay .................. C12N 15/8241 800/288 |

FOREIGN PATENT DOCUMENTS

RU    2251571    5/2005

OTHER PUBLICATIONS

DF848432-1, GenBank Entry (Year: 2016).*
Emboss sequence alignment of Seq ID No. 10 (Year: 2021).*
Tanaka et al., UniProt database, accession No. A0A146I1K1, Jun. 2016.*
International Search Report for PCT/RU2017/050125 dated Feb. 28, 2018, 9 pages (with English Translation).

* cited by examiner

*Primary Examiner* — Maryam Monshipouri
(74) *Attorney, Agent, or Firm* — Nixon & Vanderhye PC

(57) ABSTRACT

The present invention is directed to nucleic acid molecules which encode novel luciferases, functional fragments thereof, homologs and mutants, as well as to proteins encoded by said nucleic acids. The nucleic acid molecules of interest are isolated from fungi or obtained by genetic engineering methods. Also, host cells, stable cell lines and transgenic organisms comprising said nucleic acid molecules are provided. In addition, antibodies specific to the proteins of the present invention are provided. Said proteins and nucleic acids are used in many applications and methods, in particular, in labelling organisms, cells, cellular organelles, or proteins. Also, said protein and nucleotide compositions are used in methods for detecting protein-protein interactions, for testing promoter activity under various conditions. Finally, provided are kits for the use of proteins and nucleic acids of the present invention in the diversity of methods and applications.

6 Claims, 8 Drawing Sheets

Specification includes a Sequence Listing.

```
              10         20         30         40         50
              |          |          |          |          |
SEQ_ID_NO:_35 -----------------------------------------DYXTFLX
SEQ_ID_NO:_2  MRINISLS-SLFERLSKLSSRSIAIT-CVVLASAIAFPIIRRDYQTFLE
SEQ_ID_NO:_4  MSFIDSMKLDLVGHLFGIRNRGLAAACCAVAVASTIAFPYIRRDYQTFLS
SEQ_ID_NO:_6  MSFFDSVKLDLVGRLFGIRNRGLAVTCCAVAVASIIAFPYIRRDYQTFLS
SEQ_ID_NO:_8  MSFIDSMKLDFVGHLFGIRNRGLATACCAVAVASAIAFPIIRRDYQTFLS
SEQ_ID_NO:_10 -MVQLTRTSGFI--------------AAAVAAIAFPFIRRDYQTFLR
SEQ_ID_NO:_12 MAYQLTWIQTLV--------------LGALVAMAVAFPFIKRDYQTFLK
SEQ_ID_NO:_14 MLPAFIYKPRLVIT------------CVFVIASAIAFPFIRRDYQTFLE
SEQ_ID_NO:_16 --MNINLK-ALIGV------------CAVLITAAV-PPFVRDYHTFLE
SEQ_ID_NO:_18 --MNINLK-ALIGV------------CAVLITAAV-PPFVRDYHTFLE 60         70         80         90        100
              |          |          |          |          |
SEQ_ID_NO:_35 XGPSYAPQNXXGYXIVXVLXLFRXEXXXXXIVXXXPEKRXWLXXLPXRXG
SEQ_ID_NO:_2  VGPSYAPQNFRGYIIVCVLSLFRQEQKGLAIYDRLPEKRRWLADLPPREG
SEQ_ID_NO:_4  GGPSYAPQNFRGYFIVCVLALFRQEQKGLAIYDRLPEKRRWLPDLPPRNG
SEQ_ID_NO:_6  GGPSYAPQNFRGYIIVCVLALFRQEQKGLAIYDRLPEKRRWLPDLPPRNG
SEQ_ID_NO:_8  GGPSYAPQNFKGYIIVCVLALFRQEQKGLAIYDRLPEKRRWLPDLPPRNG
SEQ_ID_NO:_10 GGPSYAPQNYRGYIIVVLSLFRGEEKGLAIYDRLPEKRTWLPELPRRAG
SEQ_ID_NO:_12 GGPSYAPQNYRGYIIVLVLALFRQEQLGLEIYDRXPEKRRWLANLPQREG
SEQ_ID_NO:_14 VGPSYAPQNLQGYIIVCVLSLFRQEQKDVAIYDRLPEKRRWLGDLPFREG
SEQ_ID_NO:_16 GGPSYAPQNLQGYIIVLVLSLFRGEETGLEIYDRLPEKRRWLEELPVREG
SEQ_ID_NO:_18 GGPSYAPQNLQGYIIVLVLSLFRGEETGLEIYDRLPEKRRWLEELPVREG 110        120        130        140        150
              |          |          |          |          |
SEQ_ID_NO:_35 XRPXXTSHIIQRQXXQXXDXXFXXXXXLXXXXIXRXQXRHXXXTXXXXSXF
SEQ_ID_NO:_2  TRPSITSHIIQRQRTQLVDQEFATRELIDKVIPRVQARHTDKTFLSTSKF
SEQ_ID_NO:_4  PRPITTSHIIQRQRNQAPDPKFALEELKATVIPRVQARHTDLTHLSLSKF
SEQ_ID_NO:_6  PRPITTSHIIQRQRNQAPDLKFALEELKATVIPRVQARHTDLTHLSLSKF
SEQ_ID_NO:_8  PRPITTSHIIQRQRNQAPDSKFALEELKATVIPRVQARHTDLTHLSLSKF
SEQ_ID_NO:_10 DRPKTSHIIQRQLDQYPDPDVLKALKATVIPRVQARHTDKTHLALSKF
SEQ_ID_NO:_12 PRPKTTSHIIQRQLSQHTDPAGAAYLKDTVIPRVQARHAANTHIARSTF
SEQ_ID_NO:_14 PRPSITSHIIQRQRTQLADAEFATKELIGKHIPRVQARHTNTFLSTSKF
SEQ_ID_NO:_16 PRPKTTSHIIQRQLNQHVDPDFGMNSLKGSVIRRLQSRHQDITQLALSKF
SEQ_ID_NO:_18 PRPKTTSHIIQRQLNQHVDPDFGMNSLKGSVIRRLQSRHQDITQLALSKF 160        170        180        190        200
              |          |          |          |          |
SEQ_ID_NO:_35 EFHAXAIFXXXXXXXXPXXXPXXXTVRRTKXEIAHMHDYHDXTXHLALA
SEQ_ID_NO:_2  EFHAKAIFLLPSIPINDPLNIPSHDTVRRTKREIAHMHDYHDCTLHLALA
SEQ_ID_NO:_4  EFHAEAIFLLPSVPIDDPKNVPSHDTVRRTKREIAHMHDYHDFTLHLALA
SEQ_ID_NO:_6  EFHAEAIFLLPSVPIDDPKNVPSHDTVRRTKREIAHMHDYHDFTLHLALA
SEQ_ID_NO:_8  EFHAEAIFLLPSVPIDDPKNVPSHDTVRRTKREIAHMHDYHDFTLHLALA
SEQ_ID_NO:_10 EFHAEAIFVRPEIALDPKHIPSHDTVRRTKREIAHMHDYHDCTLHLALA
SEQ_ID_NO:_12 EFHAAAIFLNADVPL--PEGLPASETVRRTKGEIAHMHDYHDCTLHLALA
SEQ_ID_NO:_14 EFHAQAIFLLPSIPINDPQNIPSHDTVRRTKREIAHMHDYHDCTLHLALA
SEQ_ID_NO:_16 EFHAEAIFLRPDVAINDPKHVPSHDTVRRTKREIAHMHDYHDYTCHLALA
SEQ_ID_NO:_18 EFHAEAIFLRPDIAINDPKHVPSHDTVRRTKREIAHMHDYHDYTCHLALA 210        220        230        240        250
              |          |          |          |          |
SEQ_ID_NO:_35 AXDKKXVXXKGWGQRHPLAGPGXPGPPXEWTFXYAPRXEXXXVXEXIXE
SEQ_ID_NO:_2  AQDGKEVLKKGWGQRHPLAGPGVPGPPTEWTFLYAPRNEEEARVVEMIIE
SEQ_ID_NO:_4  AQDGKEVVSKGWGQRHPLAGPGVPGPPTEWTFIYAPRNEEELAVVEMIIE
SEQ_ID_NO:_6  AQDGKEVVSKGWGQRHPLAGPGVPGPPTEWTFIYAPRNEEELAVVEMIIE
SEQ_ID_NO:_8  AQDGKEVVAKGWGQRHPLAGPGVPGPPTEWTFIYAPRNEEELAVVEMIIE
SEQ_ID_NO:_10 AQDGKQVLQKGWGQRHPLAGPGXPGPPTEWTFLYAPRTEEEVKVVETIVE
SEQ_ID_NO:_12 AADGKEVVGKGWGQRHPLAGPGVPGPPNEWTFIYAPRNEEEGVVEQIVE
SEQ_ID_NO:_14 AQDGKEVLEKGWGQRHPLAGPGVPGPPTEWTFLYAPRSEEEVRVVEMIVE
SEQ_ID_NO:_16 AQDGKQVIAKGWGQRHPLAGPGVPGPPTEWTFLYAPRNEAEVQVLETIIE
SEQ_ID_NO:_18 AQDGKQVIAKGWGQRHPLAGPGXPGPPTEWTFLYAPRNEAEVQVLETIIE 260        270
              |          |
SEQ_ID_NO:_35 AXXXYMXN--------
SEQ_ID_NO:_2  ASIGYMTN-DPAGKIVENAK-----
SEQ_ID_NO:_4  ASIGYMTN-DPAGVVIA--------
SEQ_ID_NO:_6  ASIGYMTN-DPAGKTIA--------
SEQ_ID_NO:_8  ASIGYMTN-DPAGTVIV--------
SEQ_ID_NO:_10 ASIYYMTNAEKPVELVQ--------
SEQ_ID_NO:_12 AAIGYMSN-VPALE-----------
SEQ_ID_NO:_14 ASVVYMTN-DPADKIVEATVQGTEE
SEQ_ID_NO:_16 ASIGYMSN-APALGGSE--------
SEQ_ID_NO:_18 ASIGYMSN-APALGGSE--------
```

Fig. 5

LUCIFERASES AND METHODS FOR USING SAME

This application is the U.S. national phase of International Application No. PCT/RU2017/050125 filed Dec. 6, 2017 which designated the U.S. and claims priority to RU 2017102986 filed Jan. 30, 2017, the entire contents of each of which are hereby incorporated by reference.

FIELD OF THE INVENTION

The present invention relates generally to the field of biology and chemistry and more particularly to luciferases.

BACKGROUND OF THE INVENTION

Bioluminescence refers to the ability of biological organisms or biomolecules to produce and emit light. Ability to produce bioluminescence is determined by the presence of a specific protein: a luciferase or a photoprotein. Luciferases are enzymes which catalyze the oxidation of low molecular weight compounds, i. e. luciferins, and convert them into oxyluciferins. The oxidation is accompanied by the emission of light and release of oxyluciferin.

Photoproteins also catalyze the oxidation of luciferin; however, in this case, luciferin acts as a prosthetic group to form a stable photoprotein complex. The quantity of light produced by a photoprotein is approximately proportional to a concentration thereof, while for luciferase it depends on concentrations of both the enzyme and luciferin. In many cases, bioluminescent reaction catalyzed by a photoprotein is activated in response to release of metal ions in the medium. For example, aequorin photoprotein catalyzes the oxidation of luciferin (coelenterazine) in response to release of calcium ions, which results in emitting short flashes of light.

Luciferases are used as reporter genes in many applications of biomedicine and biotechnology. In particular, they are used in diagnostic methods, methods for detecting microorganisms and toxic agents in a medium; they are also used for determining concentrations of various substances, for detecting activation of signalling cascades, etc. [Scott et al., Annu Rev Anal Chem, 2011, 4: 297-319; Badr and Tannous, Trends Biotechnol. 2011, 29: 624-33; Andreu et al., FEMS Microbiol Rev. 2011, 35: 360-94]. Many methods of the application of luciferases have been reviewed [Kaskova et al., Chem Soc Rev., 2016, 45: 6048-6077; Scott et al., Annu Rev Anal Chem, 2011, 4: 297-319; Widder and Falls, IEEE Journal of Selected Topics in Quantum Electronics, 2014, 20: 232-241].

Several types of bioluminescent systems are known nowadays. It has been shown that various organisms developed them independently in the course of evolution more than forty times [Herring, Journal of Bioluminescence and Chemiluminescence, 1987, 1: 147-63; Haddock et al., Annual Review of Marine Science, 2010; 2: 443-93].

Luciferase from *Photinus pyralis* (North American firefly) catalyzing the oxidation of D-luciferin has been described [de Wet et al., Proc. Natl. Acad. Sci. USA, 1985, 82: 7870-3; de Wet et al., Proc. Natl. Acad. Sci. USA, 1987, 7: 725-37]. Oxidation of D-luciferin is accompanied by the release of yellow-green light having an emission maximum at 560 nm. The same D-luciferin is oxidized by other insect luciferases: as of today, more than 30 enzymes from various insect species of Phengodidae, Elateridae and Lampyridae families, emitting light with emission maxima in the range of 536 to 630 nm have been cloned. Also, mutant forms of insect luciferases have been described and synthetic D-luciferin analogs have been produced making it possible to obtain luciferin-luciferase pairs having different properties [Thorne et al., Chem Biol., 2010, 17: 646-57. Despite a wide variety of analogs, D-luciferin remains the most common substrate for in vivo bioluminescence due to high quantum efficiency of the reaction (0.88+−0.25 [Seliger and McElroy, Arch Biochem Biophys, 1960, 88: 136-141]). A significant difficulty in using this system is a relatively large molecular weight of luciferase from *Photinus pyralis* (61 kDa). This fact makes it unsuitable for creating several chimeric proteins (for example, for investigation of viruses) because of low stability of the increased genome thereof [Tran et al., J Virol, 2013, 87: 13321-13329; Tran et al., Viruses, 2015, 7: 5319-5327]. Another difficulty is a need to obtain D-luciferin in enantiomerically pure form since an isomer thereof, L-luciferin, is a strong competitive inhibitor of the reaction [Lembert, Biochem J, 1996, 317: 273-277]. The fact that luciferase from *Photinus pyralis* is not secreted places additional limitations upon quantifying the in vivo bioluminescent signal.

Also, a large group of luciferases and photoproteins catalyzing the oxidation of coelenterazine has been described. For example, coelenterazine-dependent bioluminescent systems in *Renilla, Gaussia* and *Metridia longa* have been described [O. Shimomura, Bioluminescence: Chemical Principles and Methods, World Scientific Publishing Co. Pte. Ltd, Singapore, 2006, 470 p.] and are widely used. Mutant forms of coelenterazine-dependent luciferases and photoproteins and synthetic analogs of coelenterazine have also been obtained [Kaskova et al., Chem Soc Rev., 2016, 45: 6048-6077]. Despite the plurality of advantages of the coelenterazine system, i. e. the ability to be secreted, small size and a wide variety of available luciferases, the main limitations for application thereof are primarily related to the location of a bioluminescence emission maximum in the blue region; as a result, the blue light is mostly absorbed in vivo by the tissues of interest. Besides, bioluminescence substrate itself can emit light during non-enzymatic oxidation by ambient oxygen (presence of superoxide anions and peroxynitrite ions in tissues enhances the process) resulting in noise in the measured bioluminescent signal.

Another example of a bioluminescent system related to marine bacteria has been described. This system is significantly different from other bioluminescent systems. Bacterial luciferin (myristic aldehyde) is oxidized during the reaction but is not a bioluminescence emitter [O. Shimomura, Bioluminescence: Chemical Principles and Methods, World Scientific Publishing Co. Pte. Ltd, Singapore, 2006? 470 p.]. In addition to luciferin, the key components of the luminescent reaction are NADH (nicotinamide adenine dinucleotide), and FMN-$H_2$ (flavin mononucleotide), the oxidized derivative of which acts as the true light source. Bioluminescent systems of marine bacteria are of limited use since they are applicable only for prokaryotic expression systems.

Bioluminescent system of the ostracod *Cypridina* which is characterized by highly reactive luciferin and highly stable luciferase are also known. [Shimomura et al., Science, 1969, 164: 1299-300]. One of the main disadvantages of this bioluminescent system is extremely low stability of *Cypridina* luciferin on air, especially in the presence of impurities. The bioluminescence maximum of luciferin falls in the range of 448-463 nm (depending on the ionic strength of a solution). This fact makes this system unsuitable for in vivo application in unaltered form in deep tissues.

Bioluminescent systems of dinoflagellates and euphausiids are also known. As of today, the genes coding three luciferases of this group have been cloned [O. Shimomura, Bioluminescence: Chemical Principles and Methods, World Scientific Publishing Co. Pte. Ltd, Singapore, 2006]. A significant disadvantage of these systems is the lack of knowledge thereof: full luciferase sequences have not been identified yet, and the range of application of the system have not been determined. As of today, knowledge associated with the bioluminescence mechanism of dinoflagellates and euphausiids is fragmentary.

Despite the plurality of bioluminescent systems used today, there is still a need for more luciferin-luciferase pairs possessing new properties. In particular, ATP- and NAD(P)H-independent luciferases capable of oxidizing water-soluble cell-permeant luciferins may be advantageous.

In this respect, fungal luciferases are of great interest. Fungal bioluminescence is well-known. Moreover, it was referred to in Aristotle's tractates. However, the fungal bioluminescent systems remain poorly known. In 1959, Airth and McElroy showed that the fungal bioluminescent system comprises at least a heat-sensitive component, i. e. luciferase, and a heat-insensitive component, i. e. luciferin, and NAD(P)H [Airth and McElroy, Journal of Bacteriology, 1959, 77: 249-50]. In 2015, Purtov et al. detected fungal luciferin: it was a membrane-permeant molecule—3-hydroxyhispidin [Purtov et al., Angewandte Chemie, 2015, 54: 8124-28]. However, no fungal luciferases were cloned.

SUMMARY OF THE INVENTION

The present invention provides isolated nucleic acid molecules encoding novel luciferases and functional mutants thereof. Said luciferases oxidize 3-hydroxyhispidin resulting in emission of light. Said luciferases are independent of ATP and NAD(P)H. In preferred embodiments, said nucleic acids are isolated from fungi or obtained using genetic engineering methods.

In some embodiments, the nucleic acid of the present invention encodes luciferase selected from the group SEQ ID NO: 02, 04, 06, 08, 10, 12, 14, 16 or 18. Examples of nucleotide sequences are shown in SEQ ID NO: 1, 3, 5, 7, 9, 11, 13, 15, 17.

In some embodiments, the nucleic acid of the present invention encodes luciferase comprising a specific consensus amino acid sequence shown in SEQ ID NO:35.

In some embodiments, the nucleic acid of the present invention encodes a functional fragment of luciferase which is shorter from C- and/or N-end as compared to natural luciferase.

In some embodiments, the nucleic acid of the present invention encodes luciferase, amino acid sequence of which is substantially identical to luciferase selected from the group SEQ ID NO: 02, 04, 06, 08, 10, 12, 14, 16 or 18. In some embodiments, the nucleic acid of the present invention encodes a functional fragment of luciferase, the amino acid sequence of which is substantially identical to a functional fragment selected from the group SEQ ID NO: 20, 22, 24, 26, 28, 30, 32 or 34.

Nucleic acid molecules which differ from the nucleotide sequences provided because of degeneracy of the genetic code or hybridize therewith also fall within the scope of the present invention.

In other embodiments, vectors comprising the nucleic acid of the present invention are also provided. In addition, the present invention provides expression cassettes comprising the nucleic acid of the present invention and regulatory elements necessary for the expression of the nucleic acid in a selected host cell. In addition, cells, stable cell lines, transgenic organisms (for example, plants, animals, fungi, microorganisms) comprising the nucleic acids, vectors or expression cassettes of the present invention are provided.

In other embodiments, the functional luciferases of the present invention which are encoded by the abovementioned nucleic acids are provided.

In addition, a kit comprising nucleic acids or vectors or expression cassettes comprising the nucleic acids of the present invention is provided.

In addition, antibodies specifically binding the proteins of the present invention or fragments thereof are provided.

In addition, methods for labelling cells, cell structures and biomolecules using the nucleic acids and proteins of the present invention are provided.

The technical result involves expansion of technical means in the field of use of bioluminescent systems. It is achieved by identifying the amino acid and nucleotide sequences of a new group of enzymes capable of catalyzing 3-hydroxyhispidin oxidation accompanied by emission of light.

BRIEF DESCRIPTION OF FIGURES

FIG. 5 shows multiple alignment of amino acid sequences of luciferases of the present invention. The N-terminal transmembrane domain is underlined. The consensus sequence is shown at the top.

DETAILED DESCRIPTION

Figure 1:
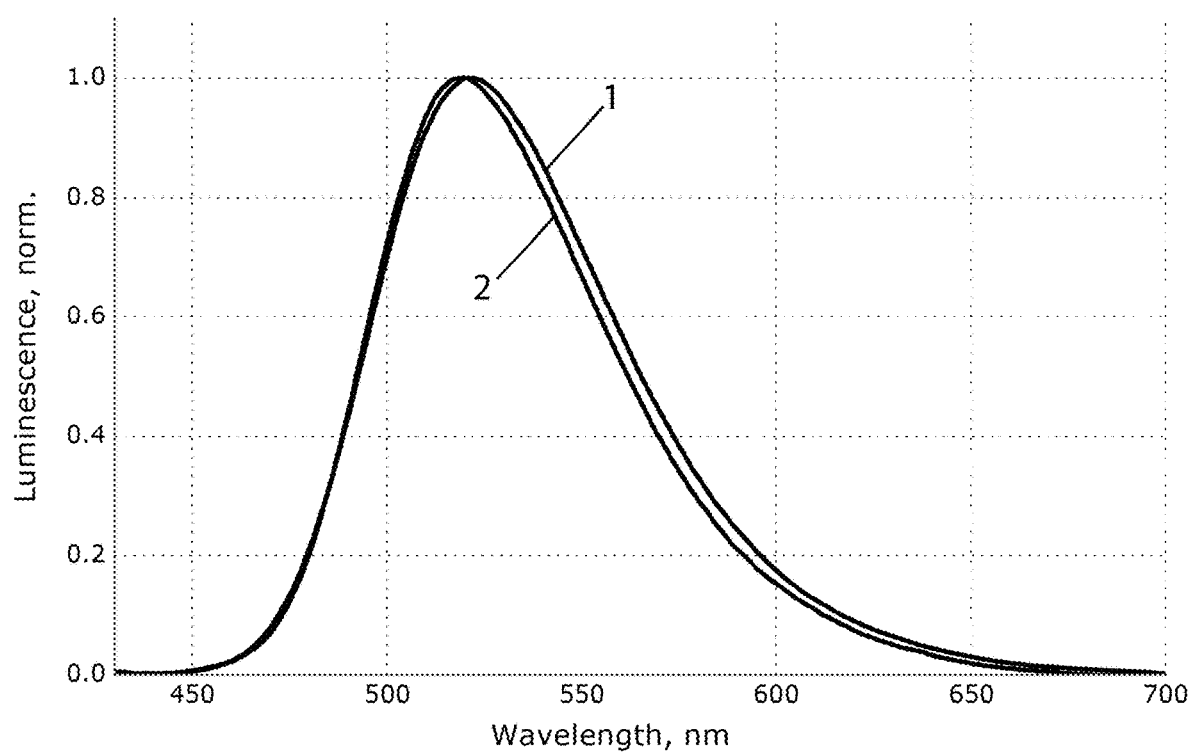
FIG. 1 shows bioluminescence spectra of luciferase from *Neonothopanus nambi* when expressed in natural (1) and heterologous (2) systems.

The present invention is directed to nucleic acid molecules which encode novel luciferases, functional fragments thereof, homologs and mutants, as well as to proteins encoded by said nucleic acids. The nucleic acid molecules of interest are isolated from fungi or are genetically engineered. Also, host cells, stable cell lines and transgenic organisms comprising these nucleic acid molecules are provided. In addition, antibodies specific to the proteins of the present invention are provided.

Said protein and nucleotide compositions are used in many applications and methods, in particular, in labelling organisms, cells, cellular organelles or proteins. Also, said protein and nucleotide compositions are used in methods for detecting protein-protein interactions and in testing promoter activity under various conditions. Finally, kits for such methods and applications are provided.

Definitions

Various terms relating to the subjects of the present invention are used above as well as in the description and claim sections.

As used herein, the term "luciferase" means a protein capable of oxidizing luciferin where the oxidation reaction is accompanied by the emission of light (luminescence) and oxidized luciferin is released.

As used herein, the term "humanized" refers to changes made to the nucleic acid sequence to optimize the codons for expression of the protein in mammalian cells (Yang et al., 1996, Nucleic Acids Research 24:4592-4593).

As used herein, the term "isolated" means a molecule or cell which are in an environment different from an environment in which the molecule or cell exist under natural conditions.

As used herein, the term "mutant" or "derivative" refers to the protein of the present invention, in which one or more amino acids are added and/or substituted and/or deleted and/or inserted at the N-terminus and/or C-terminus and/or within the native amino acid sequences of proteins of the present invention. As used herein, the term "mutant" refers to a nucleic acid molecule which encodes a mutant protein. In addition, here, the term "mutant" refers to any variant that is shorter or longer than a protein or nucleic acid.

The term "homology" is used to describe interconnection of nucleotide or amino acid sequences with other nucleotide or amino acid sequences; this interconnection is determined by the degree of identity and/or similarity between these compared sequences.

As used herein, the amino acid or nucleotide sequence is "substantially similar" or "substantially identical" to a reference sequence provided the amino acid or nucleotide sequences are at least 40% identical to the specified sequence within the region selected for comparison. Thus, substantially similar sequences are those which are, for example, at least 45% identical, or at least 50% identical, or at least 55% identical, or at least 60% identical, or at least 62% identical, or at least 65% identical, or at least 70% identical, or at least 75% identical, for example, at least 80% identical, at least 85% identical, at least 90% identical (for example, 90%, 91%, 92%, 93%, 94%, 95%, 96%, 97%, 98%, 98% or 99% identical). Two sequences which are identical to each other are also substantially similar. For the purposes of the present invention, the length of luciferase sequences being compared is at least 100 amino acids, preferably at least 200 amino acids, for example 200-230 amino acids or the full length of amino acid sequence of a protein or functional fragment. As for the nucleic acids, the length of the sequences being compared is commonly at least 300 nucleotides, preferably at least 600 nucleotides.

Identity of sequences is determined based on a reference sequence. Algorithms for sequence analysis are known in the art, for example, BLAST described in Altschul et al., J. Mol. Biol., 215, pp. 403-10 (1990). For the purposes of the present invention, comparison of nucleotide and amino acid sequences by means of Blast software package provided by the National Center for Biotechnology Information using gapped alignment with standard parameters can be used to determine the degree of identity and similarity between the nucleotide sequences and amino acid sequences.

As used herein, the term "functional" means that a nucleotide or amino acid sequence can function for a specified test or task. The term "functional" used in regard to luciferases means that a protein is capable of catalyzing a luciferin oxidation reaction accompanied by luminescence.

As used herein, "biochemical properties" refer to protein folding and maturation rate, half-life, catalysis rate, pH and temperature stability, and other similar properties.

As used herein, "spectral properties" refer to spectra, quantum efficiency and luminescence intensity, and other similar properties.

The term "operably linked" or a similar term used in regard to chimeric proteins refers to polypeptide sequences which are physically and functionally linked to each other. In the most preferred embodiments, the functions of the polypeptide components of a chimeric molecule are unchanged as compared to the functional properties of isolated polypeptide components. For example, luciferase of the present invention can be fused to a fusion partner of interest. In this case, the chimeric protein retains luciferase properties, and the polypeptide of interest retains the original biological activity thereof. In some embodiments, activity of both luciferase and a fusion partner can be reduced as compared to activities of isolated proteins. Such chimeric proteins also find application within the bounds of the present invention. The term "operably linked" or a similar term used in regard to nucleic acids means that the nucleic acids are covalently bound in such a way that the junctions thereof contain no "failures" of the reading frame and stop codons. It will be appreciated by those having skill in the art that nucleotide sequences encoding a chimeric protein comprising "operably linked" components (proteins, polypeptides, linking sequences, protein domains, etc.) consist of fragments encoding said components, where the fragments are covalently bound in such a way that a full-length chimeric protein is produced during transcription and translation of a nucleotide sequence.

As used herein, the term "specifically hybridize" refers to an association between two single-stranded nucleic acid molecules or sufficiently complementary sequences, allowing such hybridization under predetermined conditions commonly used in the art (the term "substantially complementary" is used sometimes).

A reference to a nucleotide sequence "encoding" polypeptide means that such polypeptide is produced from a nucleotide sequence during mRNA transcription and translation. For this, both a coding strand, which is identical to mRNA and commonly used in the sequence listing, and a complementary strand, which is used as a template during transcription, can be specified. It will be appreciated by those having skill in the art that the term also includes any degenerate nucleotide sequences encoding a uniform amino acid sequence. Nucleotide sequences encoding polypeptide include sequences which contain introns.

Nucleic Acid Molecules

The present invention provides nucleic acid molecules encoding luciferases and functional fragments thereof (for example, encoding truncated or extended luciferase variants). In preferred embodiments, the nucleic acid of the present invention encodes luciferase, the amino acid sequence of which is selected from the groups SEQ ID NO: 2, 4, 6, 8, 10, 12, 14, 16, 18. Nucleic acid molecules encoding homologs and mutants of said luciferases which are substantially similar to the abovementioned luciferases also fall within the scope of the present invention. Each of these specific types of nucleic acid molecules of interest is disclosed in more detail in the experimental part below.

As used herein, a nucleic acid molecule is a DNA molecule, such as genomic DNA or cDNA, or an RNA molecule, such as an mRNA molecule. In some embodiments, the nucleic acid molecule of the present invention is a DNA molecule (or cDNA) having an open reading frame that encodes the luciferase of the present invention and is capable under suitable conditions (for example, under physiological intracellular conditions) of being expressed as a luciferase in a heterologous expression system.

In some embodiments, the nucleic acid molecule of the present invention encoding luciferase is isolated from a fungus. Specific nucleic acid molecules of interest include nucleic acids encoding luciferases from *Neonothopanus nambi* (SEQ ID NO: 2), *Armillaria gallica* (SEQ ID NO: 4), *Armillaria mellea* (SEQ ID NO: 6), *Armillaria ostoyae* (SEQ ID NO: 8), *Mycena chlorophos* (SEQ ID NO: 10), *Mycena citricolor* (SEQ ID NO: 12), *Omphalotus olearius* (SEQ ID NO: 14), and *Panellus stipticus* (SEQ ID NO: 16 and 18). The nucleotide sequences of such nucleic acids are shown in SEQ ID NO: 1, 3, 5, 7, 9, 11, 13, 15, 17.

In some embodiments, the nucleic acid molecule of the present invention is genetically engineered. Methods for obtaining nucleic acids are well known in the art. For example, the availability of amino acid sequence information (for example, SEQ ID NO: 2-18) or nucleotide sequence information (for example, SEQ ID NO: 3, 5, 7, 9, 11, 13, 15 or 17) makes it possible to prepare the isolated nucleic acid molecules of the present invention by oligonucleotide synthesis. Provided the information on amino acid sequence is available, several nucleic acids which are different from each other because of degeneracy of the genetic code can be synthesized. Methods for selecting codon variants for the desired host are well known in the art.

Synthetic oligonucleotides can be prepared using the phosphoramidite method. The obtained constructs can be purified by the methods well known in the art, such as high-performance liquid chromatography (HPLC) or other methods, as described, for example, in Sambrook et al., Molecular Cloning: A Laboratory Manual, 2$^{nd}$ Ed., (1989) Cold Spring Harbor Press, Cold Spring Harbor, NY, and according to instructions described in, for example, United States Dept. of HHS, National Institute of Health (NIH) Guidelines for Recombinant DNA Research. The long double-stranded DNA molecules of the present invention can be synthesized as follows: several smaller fragments with necessary complementarity, which contain suitable ends capable of cohesion with an adjacent fragment can be synthesized. Adjacent fragments can be bound by a DNA ligase in recombination-based methods, or during PCR.

Nucleic acid molecules encoding the luciferases of the present invention can also be cloned from biological sources from a fungus belonging to the Basidiomycota division, preferably the Basidiomycetes class, in particular the Agaricales order.

The present invention also encompasses nucleic acids which are homologous, substantially similar, identical, or derived from nucleic acids encoding the proteins of the present invention.

The nucleic acids of the present invention are in an environment that is different from an environment in which they exist under natural conditions, for example, they are isolated, their number is increased, they exist or are expressed in in vitro systems or in cells or organisms other than those in which they exist under natural conditions.

Alterations or differences in a nucleotide sequence between highly similar nucleotide sequences may represent nucleotide sequence substitutions that occur during normal replication or duplication. Other substitutions can be specifically calculated and inserted into a sequence for specific purposes, such as altering the codons of certain amino acids or the nucleotide sequence of the regulatory region. Such special substitutions can be made in vitro using various mutagenesis technologies or obtained in host organisms under specific breeding conditions which induce or select these changes. Such specially prepared variants of the sequence can be called "mutants" or "derivatives" of the original sequence.

The present invention also provides a nucleic acid encoding luciferase which is substantially similar to luciferase, the amino acid sequence of which is shown in SEQ ID NO: 2, 4, 6, 8, 10, 12, 14, 16, 18. The nucleic acid encoding such a polypeptide or fragment thereof can be obtained by any of the plurality of known methods. The cDNA fragment of the present invention can be used as a hybridization probe against a cDNA library from the target organism under high stringency conditions. The probe can be a large fragment or a shorter degenerate primer. Nucleic acids having a similar sequence can be detected by hybridization under high stringency conditions, for example, at 50° C. or higher temperatures (for example, 60° C. or 65° C.), 50% formamide, 0.1×SSC (15 mM sodium chloride/1.5 mM sodium citrate), 0.1% SDS. Nucleic acids having regions substantially identical to the reference sequence, for example, allelic variants, genetically modified nucleic acid variants, etc. are bound to the reference sequence under highly stringent hybridization conditions. Such nucleotide sequences can be isolated using probes, in particular labelled probes complementary to the reference DNA sequence.

A nucleic acid encoding such a polypeptide or fragment thereof can also be detected during genomic or transcriptomic sequencing. In particular, a substantially similar luciferase can be identified among sequences of hypothetical proteins predicted based on data obtained during organism sequencing, for example, during sequencing of fungi of various species, predominantly of the Basidiomycota division, for example, of the Basidiomycetes class, in particular of the Agaricales order.

The present invention also provides a nucleic acid encoding luciferase containing a specific consensus amino acid sequence substantially similar to the sequence shown in SEQ ID NO: 35. Here, the term "consensus sequence" means an averaged amino acid sequence regularly occurring (with small variations in individual amino acids) in different luciferases of the present invention.

Mutant or derived nucleic acids can be obtained from a template nucleic acid selected from the above-described nucleic acids by modifying, deleting, or adding one or more nucleotides in the template sequence or a combination thereof to generate a variant of the template nucleic acid. Modifications, additions or deletions may be performed using any method known in the art (see for example Gustin et al., Biotechniques (1993) 14: 22; Barany, Gene (1985) 37: 111-123; and Colicelli et al., Mol. Gen. Genet. (1985) 199:537-539, Sambrook et al., Molecular Cloning: A Laboratory Manual, (1989), CSH Press, pp. 15.3-15.108), including error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, random mutagenesis, gene reassembly, gene site saturation mutagenesis (GSSM), synthetic ligation reassembly (SLR), or a combination thereof. The modifications, additions and deletions may also be introduced by a method which includes recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deleted mutagenesis, restriction-selection mutagenesis, restriction-purification mutagenesis, artificial gene synthesis, ensemble mutagenesis, chimeric nucleic acid multimer creation, or a combination thereof. In some embodiments, luciferases encoded by mutant or derived nucleic acids have the same spectral or biochemical properties as wild-type luciferase. In other embodiments, mutant or derived nucleic acids encode luciferases having altered properties.

Also, degenerate variants of nucleic acids which encode proteins of the present invention are provided. The degenerate nucleic acid variants include substitutions of nucleic acid codons with other codons which encode the same amino acids. In particular, degenerate variants of nucleic acids are generated to increase expression in a host cell. In this embodiment, nucleic acid codons that are not preferred or less preferred in host cell genes are substituted with codons that are abundantly present in the coding sequences of genes in the host cell where said substituted codons encode the same amino acid. Examples of degenerate variants of interest are described in more detail in the experimental part below.

Nucleic acids encoding truncated and extended variants of these luciferases also fall within the scope of the present invention. As used herein, these protein variants comprise amino acid sequences with the altered C-terminus, N-terminus, or both termini of a polypeptide chain.

In truncated variants, one or more (normally up to 39, more often 37 or less) amino acids may be removed from the sequence or substituted with any other amino acid. In particular, the sequence encoding a transmembrane domain and the preceding amino acid sequence from the N-terminus of luciferase can be completely or partially removed. The transmembrane domain can be identified using methods known in the prior art: for example, using algorithms described in [Krogh et al., Journal of Molecular Biology2001, 305(3):567-580] and [Sonnhammer et al., Proceedings of the Sixth International Conference on Intelligent Systems for Molecular Biology, pages 175-182, Menlo Park, C A, 1998. AAAI Press]. For analysis, software which is based on said algorithm and described in TMHMM Server v. 2.0 (Prediction of transmembrane helices in proteins) can be used. In extended variants, the C- or N-terminus of protein may contain additional amino acids. The examples of amino acid sequences of functional fragments and the corresponding encoding nucleotide sequences are shown in SEQ ID NO: 19-34. For expression of functional fragments, nucleic acids which encode them are operably linked to nucleic acids containing at least regulatory sequences and transcription initiation site. Also, these nucleic acids may comprise 6-his-tag-encoding sequences, signal peptide or functional protein domains.

The above-mentioned modifications do not substantially change the spectral properties of luciferases but can change intracellular localisation, stimulate protein folding in host cells, decrease aggregation or modulate other biochemical protein properties, for example, half-life. In some embodiments, these modifications do not change biochemical protein properties. All the above types of modifications and mutations are, as a rule, performed on the nucleic acid level.

The nucleic acid molecules of the present invention may encode the entire subject protein or a part thereof. Two- and single-stranded fragments can be obtained from a DNA sequence by chemical synthesis of oligonucleotides in accordance with standard methods, enzymatic restriction, PCR amplification, etc. In general, the size of DNA fragments will be at least approximately 15 nucleotides, normally at least approximately 18 nucleotides or approximately 25 nucleotides and may be at least approximately 50 nucleotides. In some embodiments, the subject nucleic acid molecules may have a size of approximately 100, approximately 200, approximately 300, approximately 400, approximately 500, approximately 600 or more. The subject nucleic acids can encode fragments of the subject proteins or complete proteins; for example, the subject nucleic acids may encode polypeptides of approximately 25 amino acids, approximately 50, approximately 75, approximately 100, approximately 125, approximately 150, approximately 200 amino acids, up to the complete length of the protein.

The subject nucleic acids may be isolated and obtained in substantially pure form. A substantially pure form means that the nucleic acids are at least approximately 50% pure, normally at least approximately 90% pure and normally are "recombinant", i. e. flanked by one or more nucleotides commonly not bound to a sequence in a chromosome existing in nature in the natural host thereof.

Also provided are nucleic acids which encode a fused protein comprising proteins of the present invention or fragments thereof which are described in detail below.

A vector and other nucleic acid constructs comprising the subject nucleic acids are also provided. Suitable vectors comprise viral and non-viral vectors, plasmids, cosmids, phages, etc., preferably plasmids, and are used for cloning, amplifying, expressing, transferring, etc. the nucleic acid sequence of the present invention to a suitable host. It is easy to choose a suitable vector to those skilled in the art. To prepare the constructs, the partial or full-length nucleic acid is inserted into a vector typically by means of DNA ligase attachment to a cleaved restriction enzyme site in the vector. Alternatively, the desired nucleotide sequence can be inserted by in vivo homologous recombination, typically by attaching homologous regions to the vector on the flanks of the desired nucleotide sequence. Regions of homology are added by ligation of oligonucleotides, or by polymerase chain reaction using primers comprising both the region of homology and a portion of the desired nucleotide sequence, for example. The vector, as a rule, has an origin of replication, which ensures replication thereof in the hosts as a result of being introduced into a cell as an extrachromosomal element. The vector may also contain regulatory elements providing the expression of the nucleic acid in the host and the generation of recombinant functional luciferase. In the expression vector, said nucleic acid is functionally linked to a regulatory sequences which may include promoters, enhancers, terminators, operators, repressors, silencers, insulators and inducers.

Expression cassettes or systems used inter alia for obtaining the subject luciferases or chimeric proteins based thereof, or for replication of the subject nucleic acid molecules are also provided. The expression cassette may exist as an extrachromosomal element or may be integrated into the genome of the cell as a result of introduction of said expression cassette into the cell. For expression, the gene product encoded by the nucleic acid of the invention is expressed in any convenient expression system, including, for example, bacterial, yeast, plants, insects, amphibians or mammalian systems. In the expression cassette, the target nucleic acid is operably linked to regulatory sequences that can include promoters, enhancers, termination sequences, operators, repressors, and inducers. Methods for preparing expression cassettes or systems capable of expressing the desired product are known for a person skilled in the art.

Cell lines which sustainably express the proteins of the present invention can be selected by the methods known in the art (e.g. co-transfection with a selection marker, such as dhfr, gpt, neomycin or hygromycin allows the identification and isolation of the transfected cells that contain the gene integrated into a genome).

The above expression systems can be used in prokaryotic or eukaryotic hosts. Host cells, such as *E. coli, B. subtilis, S. cerevisiae*, insect cells or higher organism cells which are not human embryo cells, such as yeast, plants (for example, *Arabidopsis thaliana, Nicotiana benthamiana, Physcomitrella patens*), vertebrates, for example, COS 7 cells, HEK 293, CHO, *Xenopus* oocytes, etc. may be used for production of the protein.

When any of the above-referenced host cells, or other appropriate host cells or organisms are used to replicate and/or express the nucleic acids of the invention, the resulting replicated nucleic acid, expressed protein or polypeptide is within the scope of the invention as a product of the host cell or organism. The product may be recovered by an appropriate means known in the art.

Also provided are small DNA fragments of the subject nucleic acids, that are useful as primers for PCR, rolling circle amplification, hybridization screening probes, etc. Larger DNA fragments are useful for production of the encoded polypeptide, as described previously. However, for use in geometric amplification reactions, such as PCR, a pair of small DNA fragments, i.e. primers, is used. The exact composition of the primer sequence is not critical to the invention, but for most applications the primers will hybridize to the subject sequence under stringent conditions, as known in the art. It is preferable to choose a pair of primers that will generate an amplification product of at least approximately 50 nucleotides, preferably at least approximately 100 nucleotides and extend to the entire nucleic acid sequence. Algorithms for the selection of primer sequences are generally known, and are available in commercial software packages. Amplification primers hybridize to complementary strands of DNA, and will prime towards each other.

The nucleic acid molecules of the present invention may also be used to identify expression of the gene in a biological sample. The manner in which one probes cells for the presence of particular nucleotide sequences, such as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridization, and hybridization to DNA probes arrayed on a solid chip may also find use. Detection of mRNA hybridizing to the subject sequence is indicative of gene expression in the sample.

Proteins

The subject invention also provides luciferases, as well as homologs, derivatives and mutants thereof, including full-length proteins and parts or fragments thereof.

The subject proteins are luciferases capable of catalyzing the oxidation of luciferin in the presence of oxygen. The oxidation reaction is independent of the presence of ATP, NAD(P)H and other metabolites in the medium. The subject proteins differ from the known luciferases because the subject proteins oxidize 3-hydroxyhispidin having the following structure:

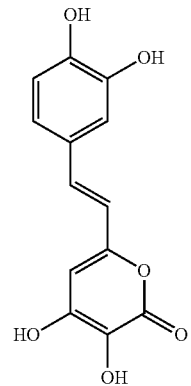

The subject luciferases can catalyze oxidation of other chemical compounds. In order to detect such compounds, isolated luciferase and said chemical compound are combined under suitable conditions, and light emitted during the oxidation reaction is detected. Examples of compounds capable of acting as luciferins for the subject luciferases are, for example, (E)-6-(4-diethylamino)styryl)-3,4-dihydroxy-2H-pyran-2-one having the following structure:

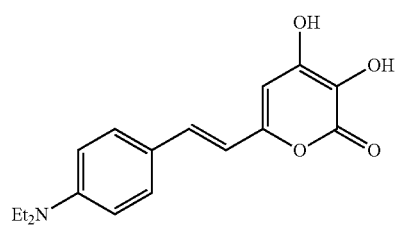

(E)-3,4-dihydroxy-6-(4-hydroxystyryl)-2H-pyran-2-one having the following structure:

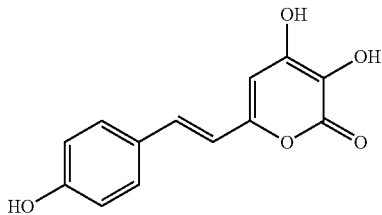 [SMILES: O=c1oc(/C=C/c2ccc(O)cc2)cc(O)c1O]

(E)-6-(2-1H-indol-3-yl)vinyl)-3,4-dihydroxy-2H-pyran-2-one having the following structure:

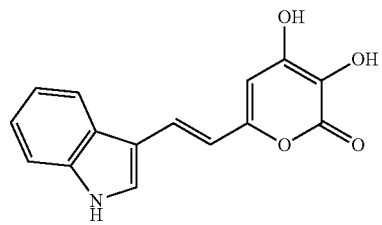 [SMILES: O=c1oc(/C=C/c2c[nH]c3ccccc23)cc(O)c1O]

(E)-6-(2-(1,2,3,5,6,7-hexahydropyrido[3,2,1-ij]quinoline-9-yl)vinyl)-3,4-dihydroxy-2H-pyran-2-one having the following structure:

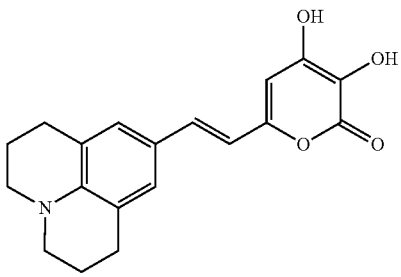 [SMILES: O=c1oc(/C=C/c2cc3c4c(c2)CCCN4CCC3)cc(O)c1O]

and (E)-3,4-dihydroxy-6-(2-(6-hydroxynaphthalene-2-yl)vinyl)-2H-pyran-2-one having the following structure:

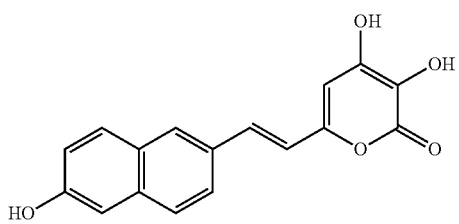 [SMILES: O=c1oc(/C=C/c2ccc3cc(O)ccc3c2)cc(O)c1O]

Oxidation of luciferin by luciferase of the present invention is accompanied by the release of detectable light.

In some embodiments of the present invention, the light released during the reaction can be detected using conventional methods (for example, visual inspection, night vision, spectrophotometry, spectrofluorimetry, image photographic recording, special luminescence and fluorescence detection equipment, such as, for example, IVIS Spectrum In Vivo Imaging System (Perkin Elmer), etc.). The recorded light may be emitted within the intensity range of one photon to easily visible light, for example, with an intensity of 1 cd, and bright light with an intensity of, for example, 100 cd or more.

The light emitted during oxidation of 3-hydroxyhispidin is within the range of 400 to 700 nm, more often within the range of 450 to 650 nm, with an emission maximum at 520-590 nm.

The subject proteins remain active at temperatures below 50° C., more often at temperatures up to 45° C., i. e. they remain active within the range of temperatures of 30-42° C. and can be used in heterologous expression systems in vitro and in vivo.

The subject proteins have pH stability within the range of 4 to 10, more often within the range of 6.5 to 9.5. The optimum pH stability of the subject proteins falls within the range of 7.0 to 8.0, for example, 7.3 to 7.5.

The specific proteins of interest include natural luciferases from *Neonothopanus nambi* (SEQ ID NO: 2), *Armillaria gallica* (SEQ ID NO: 4), *Armillaria mellea* (SEQ ID NO: 6), *Armillaria ostoyae* (SEQ ID NO: 8), *Mycena chlorophos* (SEQ ID NO: 10), *Mycena citricolor* (SEQ ID NO: 12), *Omphalotus olearius* (SEQ ID NO: 14), and *Panellus stipticus* (SEQ ID NO: 16 and 18), their recombinant and truncated variants, for example, comprising amino acid sequences shown in SEQ ID NO: 20, 22, 24, 26, 28, 30, 32, 34, and described in more detail in the experimental section below.

Luciferases substantially similar to the above luciferases and functional fragments thereof are also provided. In many embodiments, the amino acid sequences of interest are significantly identical in the sequence, for example, at least 40% identical, for example, at least 45% identical, or at least 50% identical, or at least 55% identical, or at least 60% identical, or at least 65% identical, or at least 70% identical, or at least 75% identical, for example, at least 80% identical, at least 85% identical, at least 90% identical (for example, 90%, 91%, 92%, 93%, 94%, 95%, 96%, 97%, 98%, 98% or 99% identical). In particular, this refers to the sequence of amino acids that provide protein functional regions, i.e. to the protein sequence located after the sequence of a transmembrane domain which is a part of natural luciferases of the present invention.

The present invention also provides luciferases containing a specific consensus sequence inherent in natural luciferases of the present invention and shown in SEQ ID NO: 35. The consensus sequence is obtained based on multiple comparison of luciferases of the present invention via identifying amino acids which are most commonly encountered at this position in the plurality of related sequences.

The present invention also provides mutants of the above referred proteins. Mutants may retain the biological properties of proteins from which they were obtained or may have biological properties that differ from those of wild-type proteins. The term "biological property" of proteins according to the present invention refers, without limitation, to ability to oxidize various luciferins; biochemical properties, such as in vivo and/or in vitro stability (for example, half-life); maturation rate; aggregation or oligomerization tendency as well as other similar properties. Mutations comprise alterations to one or more amino acids, deletions or insertions of one or more amino acids; N-terminus truncations or extensions, C-terminus truncations or extensions, etc.

Mutants may be obtained using conventional molecular biology techniques, such as those described in detail in the "Nucleic Acid Molecules" section above.

The proteins of the present invention are in isolated form, i.e. a given protein is substantially free from other proteins or other natural biological molecules such as oligosaccharides, nucleic acids and fragments thereof, etc. In this context, the term "substantially free" means that less than 70%, normally less than 60%, and more often less than 50% of said composition containing the isolated protein is made up of another natural biological molecule. In some embodiments, said proteins are in substantially pure form. In this context, the term "substantially pure form" means that said proteins are at least 95% pure, normally at least 97% pure, and more often at least 99% pure.

In the preferred embodiment, the target proteins are obtained using a synthesis method, for example, by expressing a recombinant nucleic acid encoding a sequence encoding the protein of interest in a suitable host, as described above. Any convenient protein purification procedures may be employed where suitable protein purification techniques are described in the appropriate reference guide (Guide to Protein Purification, (Deuthser ed.) (Academic Press, 1990). For example, a lysate may be prepared from the original source and purified using HPLC, exclusion chromatography, gel electrophoresis, affinity chromatography, etc.

The present invention also involves fusion proteins comprising the protein of the present invention or functional fragments thereof fused, for example, to a subcellular localization sequence (for example, nuclear localization signal, peroxisome localization signal, mitochondria, Golgi apparatus, etc.), signal peptide or any protein or polypeptide of interest. The fusion proteins may comprise, for example, luciferase of the present invention and a second polypeptide ("the fusion partner") operably fused in-frame to the N-terminus and/or C-terminus of luciferase. Fusion partners include, but are not limited to, polypeptides that can bind to antibodies specific to the fusion partner (for example, epitope tags), antibodies or binding fragments thereof, polypeptides that provide a catalytic function or induce a cellular response, ligands or receptors or mimetics thereof, etc.

The present invention also provides antibodies which specifically bind to luciferases of the present invention. Suitable antibodies may be obtained using techniques known in the art. For example, polyclonal antibodies may be obtained using the technique described in (Harlow and Lane Antibodies: A Laboratory Manual, (1988) Cold Spring Harbor Laboratory Press, Cold Spring Harbor, New York). Monoclonal antibodies may be obtained as described in (Goding Monoclonal Antibodies: Principles and Practice: Production and Application of Monoclonal Antibodies in Cell Biology, Biochemistry and Immunology; 3rd edition, (1996) Academic Press). Chimeric antibodies comprising humanized antibodies, single-chain antibodies and antibody fragments, such as Fv, F (ab')2 and FAb, are also of interest.

Transformants

The nucleic acids of the present invention may be used to generate transformants including transgenic organisms or site-specific gene modifications in cell lines. Transgenic cells of the present invention include one or more nucleic acids of the present invention which are present as a transgene. For the purposes of the present invention, any suitable host comprising prokaryotic (for example, *Escherichia coli*, *Streptomyces* sp., *Bacillus subtilis, Lactobacillus acidophilus*, etc.) or eukaryotic hosts other than human embryonic cells may be used. The transgenic organisms of the present invention may be prokaryotic or eukaryotic organisms including bacteria, cyanobacteria, fungi, plants and animals wherein one or more cells of the organism comprising the heterologous nucleic acid of the present invention are introduced by way of human intervention, such as by transgenic techniques well known in the art.

The isolated nucleic acid of the present invention can be introduced into the host by methods known in the art, for example, infection, transfection, transformation, gene-gun delivery or transconjugation. Techniques for transferring the nucleic acid molecules (i.e. DNA) into such organisms are widely known and provided in references, such as Sambrook et al. (Molecular Cloning: A Laboratory Manual, 3nd Ed., (2001) Cold Spring Harbor Press, Cold Spring Harbor, NY).

In one embodiment, the transgenic organism can be a prokaryotic organism. Methods for transformation of prokaryotic hosts are well known in the art (see, for example, Sambrook et al. (Molecular Cloning: A Laboratory Manual, 2nd Ed., (1989) Cold Spring Harbor Laboratory Press and Ausubel et al., Current Protocols in Molecular Biology (1995) John Wiley & Sons, Inc).

In other embodiment, said transgenic organism can be a fungus, for example, yeast. Yeast is widely used as a vehicle for heterologous gene expression (see, for example, Goodey et al., Yeast biotechnology, D R Berry et al., eds, (1987) Allen and Unwin, London, pp. 401-429, and Kong et al., Molecular and Cell Biology of Yeasts, E. F. Walton and G. T. Yarronton, eds, Blackie, Glasgow (1989) pp. 107-133). Several types of yeast vectors are available, including integrative vectors, which require recombination with the host genome for maintenance thereof, and autonomously replicating plasmid vectors.

Another host organism is an animal. Transgenic animals can be obtained by transgenic techniques well known in the art and provided in references (such as: Pinkert, Transgenic Animal Technology: A Laboratory Handbook, 2nd edition (2003) San Diego: Academic Press; Gersenstein and Vinterstein, Manipulating the Mouse Embryo: A Laboratory Manual, 3rd ed, (2002) Nagy A. (Ed), Cold Spring Harbor Laboratory; Blau et al., Laboratory Animal Medicine, 2nd Ed., (2002) Fox J. G., Anderson L. C., Loew F. M., Quimby F. W. (Eds), American Medical Association, American Psychological Association; Gene Targeting: A Practical Approach by Alexandra L. Joyner (Ed.) Oxford University Press; 2nd edition (2000)). For example, transgenic animals can be obtained via homologous recombination, where the endogenous locus is altered. Alternatively, a nucleic acid construct is randomly integrated into the genome. Vectors for stable integration include plasmids, retroviruses and other animal viruses, YACs, etc.

The nucleic acid can be introduced into a cell, directly or indirectly, via introducing into a precursor of the cell by way of deliberate genetic manipulation, such as by microinjection, or by infection with a recombinant virus or with a recombinant viral vector, etc. The term "genetic manipulation" does not include classical cross-breeding or in vitro fertilization, but rather refers to the introduction of a recombinant nucleic acid molecule. This nucleic acid molecule may be integrated within a chromosome, or it may be an extrachromosomally replicating DNA.

DNA constructs for homologous recombination comprise at least a portion of the nucleic acid of the present invention, wherein said gene has the desired one or more genetic modifications, and includes regions of homology to the target locus. DNA constructs for random integration do not need to include regions of homology to mediate recombination. Markers for positive and negative selection may also be included. Methods for generating cells having targeted gene modifications via homologous recombination are known in the art. Various techniques for transfecting mammalian cells have been described, for example, in Keown et al., Meth. Enzymol. (1990) 185:527-537).

For embryonic stem (ES) cells, an ES cell line may be employed, or embryonic cells may be obtained freshly from a host, such as a mouse, rat, guinea pig, etc. Such cells are grown on an appropriate fibroblast-feeder layer or grown in the presence of leukemia inhibiting factor (LIF). Transformed ES or embryonic cells may be used to produce transgenic animals using the appropriate technique known in the art.

The transgenic animals may be any non-human animals including non-human mammal (e.g. mouse, rat), a bird or an amphibian, etc., and used in functional studies, drug screening, etc.

Transgenic plants may also be obtained. Methods of preparing transgenic plant cells and plants are described in U.S. Pat. Nos. 5,767,367, 5,750,870, 5,739,409, 5,689,049, 5,690,045, 5,674,731, 5,656,666, 5,633,155, 5,629,470, 5,595,896, 5,576,198, 5,538,879 and 5,484,956, the disclosures of which are incorporated herein by reference. Methods for producing transgenic plants are also reviewed in Plant Biochemistry and Molecular Biology (eds. Lea and Leegood, John Wiley & Sons (1993) pp. 275-295 and in Plant Biotechnology and Transgenic Plants (eds. Oksman-Caldentey and Barz) (2002) 719 p.

For example, embryogenic explants comprising somatic cells may be used for preparation of the transgenic host. Following cell or tissue harvesting, exogenous DNA of interest is introduced into the plant cells, where a variety of different techniques is available for such introduction. With isolated protoplasts, the opportunity arises for introduction via DNA-mediated gene transfer protocols, including incubation of the protoplasts with naked DNA, such as plasmids comprising the exogenous coding sequence of interest in the presence of polyvalent cations (for example, PEG or PLO); or electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, such as auxins and cytokinins.

Other suitable methods for producing plants may be used such as "gene-gun" approach or *Agrobacterium*-mediated transformation available for those skilled in the art.

Methods of Use

The polypeptides and nucleic acids of the present invention find use in a variety of different applications. For example, they are used as reagents for diagnostics, quality control, environmental tests and other similar assays in biotechnology and medicine. In addition, they find use in domestic and entertainment-oriented applications, for example, in the generation of bioluminescent transgenic plants and animals which can be used as light sources.

For example, the nucleic acids of the composition find use for the detection of various external signals in a medium, for example, for the detection of signals in mammalian intestines. For the embodiment, expression cassettes encoding a signalling cascade are introduced into the genome of the host, where the analyzed ambient signal acts as a trigger, and luciferase gene expression acts as a reporter. Luciferase gene expression can be caused either directly by signalling cascade transmission, or via inducing genetic alterations in the cell genome using techniques described in, for example, [Kotula et al., Proc. Natl. Acad. Sci. USA, 2014, 111: 4838-4843]. For example, for creating an *E. coli* strain detecting the presence of tetracycline in an ambient medium, a luciferase coding sequence under the control of a tetA gene promoter as well as a sequence encoding tetracycline repressor (TetR) of transposon Tn10 under the control of constitutive promoter are introduced into the *E. coli* genome. Genome editing of *E. coli* is performed via techniques well known in the art, for example, described in [Sabri et al., Microbial Cell Factories, 2013, 12:60]. The presence of tetracycline in the medium is detected by comparing bioluminescence intensity after adding a 3-hydroxyhispidin solution to the genetically modified *E. coli* cells after being incubated in the sample medium and to control cells without such incubation. Similarly, other microorganism strains sensitive to other ambient medium signals can be created by substituting corresponding elements of a signalling cascade with elements specifically sensitive to the desired signals. The independence of light emission by subject luciferases from the intracellular availability of ATP, NAD(P)H and other metabolites ensures stability of the reporter signal in various physiological states of the cell.

Also, the nucleic acids of the present invention find use in methods for determining the presence of toxic substances in water, for example, hexachlorocyclohexane derivatives and others. An expression cassette providing constitutive production of luciferase operably fused to the signal of rapid protein degradation is introduced into the host (for example, *E. coli*). In order to measure toxicity, lyophilized bacteria are incubated for 90 minutes with the sample liquid in a bioluminescence detection cuvette; at the same time another aliquot of bacteria is incubated with a control liquid. Alternation in bioluminescence intensity in the analyzed probe as compared to that of a sample with a solution not containing toxic substances is the criterion for the toxic effect. Thus, one may measure the toxic effect based on the drop of luminescence intensity.

Also, the molecules of the present invention may be used for determining the concentration of 3-hydroxyhispidin in the sample solution. To this end, a reagent containing purified luciferase in a known concentration is placed into a cuvette, and the background bioluminescent signal is recorded using a luminometer. Control calibration measurements are then carried out as follows: 3-hydroxyhispidin solution of a known concentration is added to the cuvette while recording bioluminescence intensity. Difference in the magnitude of a bioluminescence intensity signal in the presence and absence of 3-hydroxyhispidin is a value proportional to concentration of 3-hydroxyhispidin. The operation is repeated for those concentrations of 3-hydroxyhispidin solutions which are relevant for the measurements to be performed. Based on the obtained data, a calibration curve of the dependence of bioluminescence intensity on 3-hydroxyhispidin concentration is plotted. The 3-hydroxyhispidin concentration in an unknown sample is determined based on bioluminescence intensity after adding 3-hydroxyhispidin solution of an unknown concentration to the reagent using the above calibration curve. The subject proteins and nucleic acids are the only existing reagents which can specifically determine the concentration of 3-hydroxyhispidin in complex mixtures comprising other compounds.

The nucleic acid of the composition can further be used to produce light-emitting transgenic plants or animals. For example, in order to produce transgenic moss (*Physcomitrella patens*), it is necessary to integrate into the genome thereof a luciferase encoding sequence optimized for expression in host cells under the control of a constitutive promoter, for example, the promoter of AktI gene of rice, or an inducible promoter, for example, the heat-sensitive promoter of Gmhsp17.3B gene of soybean. Any of the methods known in the art may be used for such integration, for example, homologous recombination induced by the formation of a double-stranded gap in the genomic DNA of moss using the Cas9 nuclease from *Streptococcus pyogenes* and a guide RNA complementary to the genomic locus. In this case, the genetic construct being integrated should be flanked by regions homologous to the regions of the genome in the area of a double-stranded gap having about 250 nucleotides in length. Any of the known techniques may also be used to deliver DNA to the moss cells, for example, transformation of moss protoplasts with naked DNA using polyethylene glycol. After the transformation, the moss protoplasts should be grown in a growth medium for cell wall regeneration, then they should be plated on a solid medium for the regeneration of gametophytes. Genetically modified plants may serve as light sources when 3-hydroxyhispidin or related molecules are added to the medium or soil, or autonomously bioluminesce if 3-hydroxyhispidin biosynthesis occurs in the host cells. The subject luciferases emit predominantly green light and thus are optimally suitable for the emission of light through photosynthetic plant tissues due to reduced absorption of such tissues in the green region of the visible spectrum.

The nucleic acids of the composition can also be used to visualize cell proteins, organelles, individual cells or tissues. For example, in order to visualize the migration of cancer cells in an organism, the nucleic sequences of luciferases are introduced into cancer cells as part of an expression cassette or expression vector. Any of the methods known in the art can be used for such introduction. For example, nucleic acids encoding luciferase can be integrated into the genome of cancer cells before implanting into the host. In other embodiments, nucleic acids are introduced into all organism cells, but are under the control of promoters active in cancer cells only. Since 3-hydroxyhispidin is capable of penetrating through cell membranes, the subject luciferases can be visualized in vivo in living organisms without tissue fixation and permeabilization. In order to visualize the development of cancer tumours and metastasis, luciferin solution must be introduced into the sample organism, and the tissues must be visualized using equipment suitable for detecting bioluminescence.

Kits

The present invention also provides kits for implementing one or more applications of the nucleic acids and proteins of the present invention.

Said kits typically include the protein according to the present invention or a nucleic acid encoding such protein, preferably with elements to provide the expression of the target protein in the host, for example, an expression vector or expression cassette containing a nucleic acid encoding the target protein. Also, said kits include luciferin for carrying out a luminescence reaction mediated by luciferase of the present invention.

In some embodiments, luciferin is selected from the group comprising 3-hydroxyhispidin, (E)-6-(4-diethylamino)styryl)-3,4-dihydroxy-2H-pyran-2-one, (E)-3,4-dihydroxy-6-(4-hydroxystyryl)-2H-pyran-2-one, E)-6-(2-1H-indol-3-yl)vinyl)-3,4-dihydroxy-2H-pyran-2-one, (E)-6-(2-(1,2,3,5,6,7-hexahydropyrido[3,2,1-ij]quinoline-9-yl)vinyl)-3,4-dihydroxy-2H-pyran-2-one and (E)-3,4-dihydroxy-6-(2-(6-hydroxynaphthalene-2-yl)vinyl)-2H-pyran-2-one.

Said kit components are normally present in a suitable storage medium, such as a buffered solution, normally in a suitable container. Said components may be present in a kit in a lyophilized form.

Also, a kit may comprise antibodies specific for the subject protein. In some embodiments, said kit comprises a plurality of different vectors, each of which encodes the target protein, where said vectors are designed for expression in different media and/or under various conditions such as, for example, constitutive expression, where said vector comprises a strong promoter for expression in mammalian cells, or a non-promoter vector with a multiple cloning site for conventional promoter integration and prolonged expression, etc.

In addition to the above components, the target kits also include instructions for implementing the subject methods. Instructions may be present in the target kits in different forms, and one or more of such forms may be present in each kit.

The examples below are offered by way of illustration and not by way of limitation.

EXAMPLES

Example 1. Isolating Coding Sequence of Luciferase from *Neonothopanus nambi*

The total RNA from the mycelium of *Neonothopanus nambi* was isolated using the method described in [Chomczynski and Sacchi, Anal. Biochem., 1987, 162, 156-159]. cDNA was amplified using SMART PCR cDNA Synthesis Kit (Clontech, USA) according to the manufacturer's protocol. The PCR product was cloned into pGAPZ vector (Invitrogen, USA) and transformed into competent *E. coli* cells of XL1 Blue strain. The bacteria were grown on Petri dishes in the presence of zeocin antibiotic. After 16 hours, the colonies were washed from the dishes, mixed intensively, and plasmid DNA was extracted therefrom using a plasmid DNA extraction kit (Evrogen, Russia). The isolated plasmid DNA was linearized by AvrII restriction site and used to transform *Pichia pastoris* GS115 cells. Electroporation was carried out according to a method using lithium acetate and dithiothreitol, described in [Wu and Letchworth, Biotechniques, 2004, 36:152-4]. The electroporated cells were spread on Petri dishes containing RDB medium comprising 1 M sorbitol, 2% (w/v) glucose, 1.34% (w/v) yeast nitrogen base (YNB), 0.005% (w/v), 0.00004% (w/v) biotin and 2% (w/v) agar. The diversity of the resulting cDNA library of *Neonothopanus nambi* in yeast amounted to approximately one million clones. The obtained colonies were sprayed with a solution of 3-hydroxyhispidin and the presence of luciferase in the cells was detected by light emission. IVIS Spectrum CT (PerkinElmer, USA) was used to detect light emitted by the colonies. The colonies in which luminescence was detected after adding 3-hydroxyhispidin were selected and used as a template with standard plasmid primers for PCR. The PCR products were sequenced by the Sanger method. The obtained nucleic acid sequence is shown in SEQ ID NO: 01. The amino acid sequence encoded therewith is shown in SEQ ID NO: 02.

In order to analyse the bioluminescence of expressed luciferase, *Pichia pastoris* colonies in which luminescence was observed were isolated and grown in 750 ml flasks filled with 250 ml of YPD medium for 72 hours at 30° C. and stirred at 200 rpm. Luciferase-expressing cells were then pelleted by centrifugation at 5000 g for 15 minutes at 4° C. The obtained pellet was resuspended in a 0.1 M phosphate buffer, pH 7.4, comprising 0.1% DDM for two hours at 4° C. The suspension was centrifuged at 21000 g for 30 min at 4° C. The bioluminescence reaction was activated by adding 750 µl of the obtained supernatant to 250 µl of the solution of 3-hydroxyhispidin (25 µM) in 1% DDM. Varian Cary Eclipse spectrofluorimeter was used to detect bioluminescence. The obtained spectrum was substantially identical to that of *Neonothopanus nambi* mycelium bioluminescence (FIG. 1).

Example 2. Isolating Coding Sequences of Luciferases from Various Fungal Species Genomic DNA was isolated from *Armillaria gallica, Armillaria mellea, Armillaria ostoyae, Mycena chlorophos, Omphalotus olearius* and *Panellus stipticus* and full genomic sequencing was carried out using Illumina HiSeq technology (Illumina, USA) according to the manufacturer's recommendations. The sequencing results were used to predict the amino acid sequences of hypothetical proteins and to search for homologs of luciferase from *Neonothopanus nambi*, detected as described in Example 1. The homologs were searched using an algorithm for sequence analysis, which is described in Altschul et al., J. Mol. Biol., 215, pp. 403-10 (1990), and software provided by the National Center for Biotechnology Information. The amino acid sequences were searched in fungal genomic sequencing data in the NCBI Genbank database. The standard parameters of BLASTP search program were used for the search. As a result, sequences of hypothetical proteins, i. e. homologs of luciferase from *Neonothopanus nambi* in *Armillaria gallica, Armillaria mellea, Armillaria ostoyae, Mycena chlorophos, Omphalotus olearius, Panellus stipticus* and *Mycena citricolor* were detected. All the detected luciferases are substantially identical to each other. The degree of identity of the amino acid sequences is shown in Table 1.

vector (Clontech), plasmid DNA was isolated and sequenced by the Sanger method using M13 universal primers. In all cases, the cDNAs of the sample fungi revealed luciferase sequences.

Amplification of *Panellus stipticus* cDNA resulted in two variants of luciferase sequence characterized by a single amino acid substitution of valine with isoleucine at position 146 (SEQ ID NO: 15-18).

Example 3. Expressing Luciferases in Mammalian Cells

Figure 2:
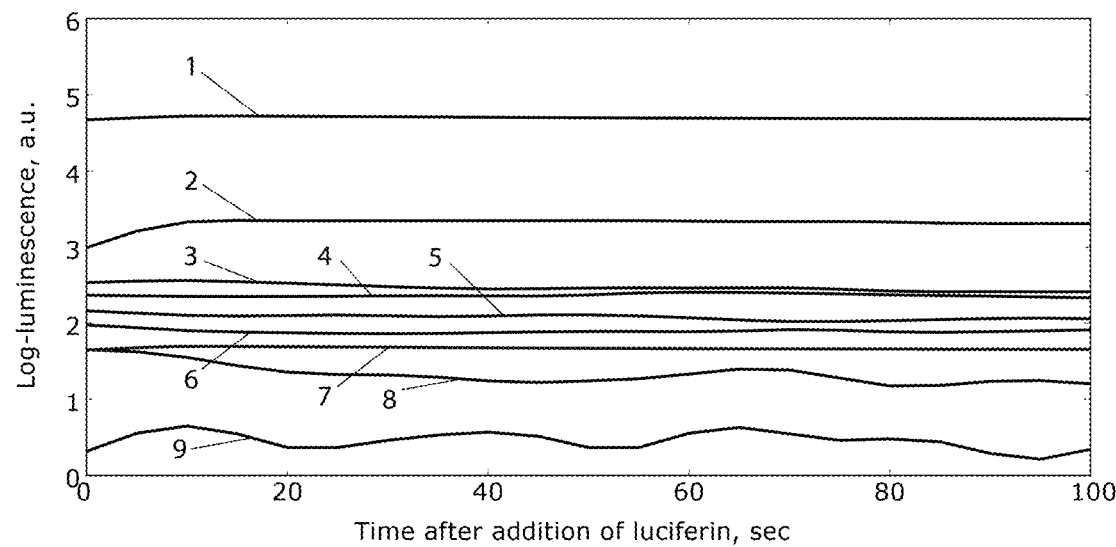
FIGS. 2 and 3 show change in bioluminescence intensity by HeLa Kyoto (FIG. 2) and HEK293T (FIG. 3) cells expressing luciferases from *Neonothopanus nambi* (1), *Armillaria mellea* (2), *Mycena citricolor* (3), *Armillaria ostoyae* (4), *Mycena chlorophos* (5), *Armillaria gallica* (6), *Panellus stipticus* (7), *Omphalotus olearius* (8) and by non-transfected control cells (9), over time.
Figure 3:
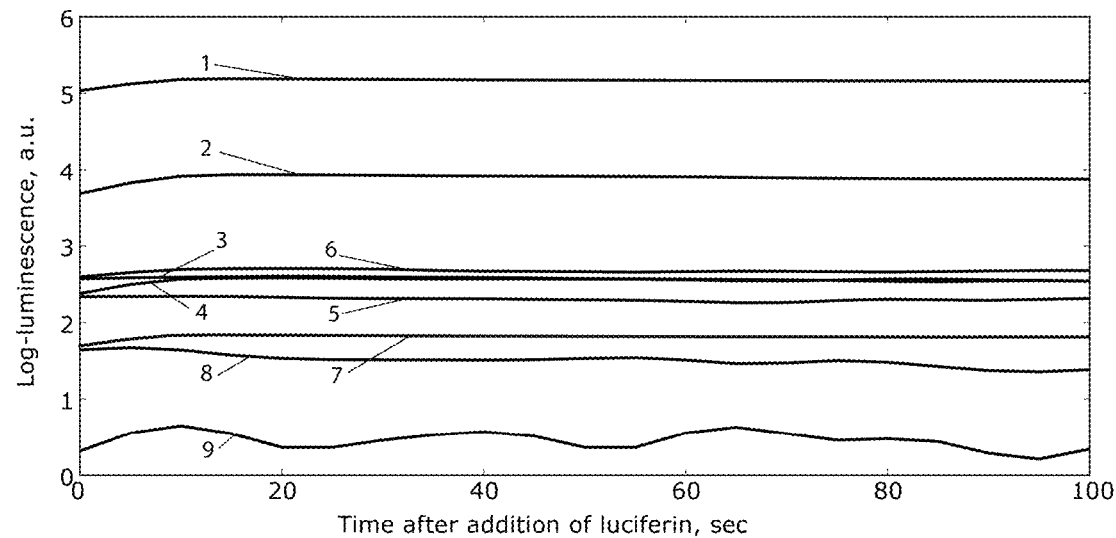

Coding sequences of luciferases obtained as shown in examples 1 and 2 were optimized (humanized) for expression in mammalian cells. Humanized nucleic acids were obtained by oligonucleotide synthesis using standard techniques. The nucleotide profile of humanized nucleic acids is shown in SEQ ID NOs: 44-51, the amino acid profile of the corresponding proteins is identical to wild-type proteins shown in SEQ ID NOs: 2, 4, 6, 8, 10, 12, 14, 16. The obtained nucleic acids were cloned into pmKate2-keratin vector (Evrogen, Russia) using NheI and NotI restriction sites instead of a sequence encoding mKate2-keratin fusion protein. Plasmid DNA was purified and transfected into HEK293NT and HeLa cells using FuGENE HD Transfection Reagent (Promega, USA) according to the manufacturer's protocol. 24 hours after the transfection procedure, 3-hydroxyhispidin at a concentration of 660 µg/ml was added to the medium, and cell luminescence was detected using IVIS Spectrum CT (PerkinElmer). Intensity of light emission of all samples was by an order of magnitude and greater than the signal coming from the non-transfected control cells (FIG. 2). Nucleotide sequence SEQ ID No:51

TABLE 1

Degree of identity of amino acid sequences of luciferases

|  | SEQ ID NO: 2 | SEQ ID NO: 4 | SEQ ID NO: 6 | SEQ ID NO: 8 | SEQ ID NO: 10 | SEQ ID NO: 12 | SEQ ID NO: 14 | SEQ ID NO: 16 | SEQ ID NO: 18 |
|---|---|---|---|---|---|---|---|---|---|
| SEQ ID NO: 2 | 1.000 | 0.745 | 0.760 | 0.745 | 0.658 | 0.629 | 0.789 | 0.655 | 0.658 |
| SEQ ID NO: 4 |  | 1.000 | 0.953 | 0.964 | 0.687 | 0.658 | 0.684 | 0.665 | 0.662 |
| SEQ ID NO: 6 |  |  | 1.000 | 0.945 | 0.684 | 0.651 | 0.687 | 0.669 | 0.665 |
| SEQ ID NO: 8 |  |  |  | 1.000 | 0.687 | 0.651 | 0.684 | 0.669 | 0.665 |
| SEQ ID NO: 10 |  |  |  |  | 1.000 | 0.669 | 0.662 | 0.731 | 0.735 |
| SEQ ID NO: 12 |  |  |  |  |  | 1.000 | 0.633 | 0.684 | 0.680 |
| SEQ ID NO: 14 |  |  |  |  |  |  | 1.000 | 0.662 | 0.665 |
| SEQ ID NO: 16 |  |  |  |  |  |  |  | 1.000 | 0.996 |
| SEQ ID NO: 18 |  |  |  |  |  |  |  |  | 1.000 |

Based on multiple alignment of conserved regions of nucleotide sequences, degenerate primers were constructed. Structures of the primers are shown in SEQ ID No: 36-43. Total RNA was isolated from fruiting bodies and mycelia of *Armillaria gallica, Armillaria mellea, Armillaria ostoyae, Mycena chlorophos, Mycena citricolor, Omphalotus olearius,* and *Panellus stipticus* and cDNA was prepared as described in Example 1. The obtained cDNA was used for PCR with the above primers. PCR was carried out in 50 µl reaction mixture comprising 1 µl of 20-fold amplified cDNA, Encyclo polymerase mix (Evrogen), 1-fold buffer provided by the manufacturer, 200 µM dNTPs and 0.5 µM of one of primers 1711-1714 and 0.5 µM of one of primers 1715-1718. 30 PCR cycles were carried out in PTC-200 MJ Research Thermal Cycler using the "Block" temperature control method (each cycle was carried under the following conditions: 95° C. for 10 sec, 55° C. for 10 seconds, and 72° C. for 1 minute). The PCR product was cloned into pTAdv incorporated into vector was subjected to site-directed mutagenesis with the replacement of valine with isoleucine at position 146. Vector comprising the obtained sequence was transfected into HEK293NT cells. 24 hours after the transfection procedure, 3-hydroxyhispidin at a concentration of 660 µg/ml was added to the medium, and cell luminescence was detected using IVIS Spectrum CT (PerkinElmer). It was shown that this variant is also capable of the oxidation of 3-hydroxyhispidin in a bioluminescent reaction.

Example 4. Expressing Luciferase from *Neonothopanus nambi* in *Pichia pastoris* Cells DNA encoding luciferase from *Neonothopanus nambi* was obtained as shown in Example 1. The luciferase gene was amplified using gene-specific terminal primers and cloned into GAP-pPicZA expression vector (Invitrogen) using BstBI and SalI restriction endonuclease sites, in-frame with a sequence encoding C-terminal his-tag. By means of electroporation, the obtained gene construct was transformed into *Pichia pink* strain characterized by low protease activity. The electroporation procedure was carried out according to a method using lithium acetate and dithiothreitol, described in [Wu and Letchworth, Biotechniques, 2004, 36:152-4]. The electroporated cells were spread on Petri dishes containing YPD medium (2% (w/v) peptone, 1% (w/v) yeast extract, 2% (w/v) glucose, 2% (w/v) agar) and zeocin antibiotic at a concentration of 100 µg/ml.

Figure 4:
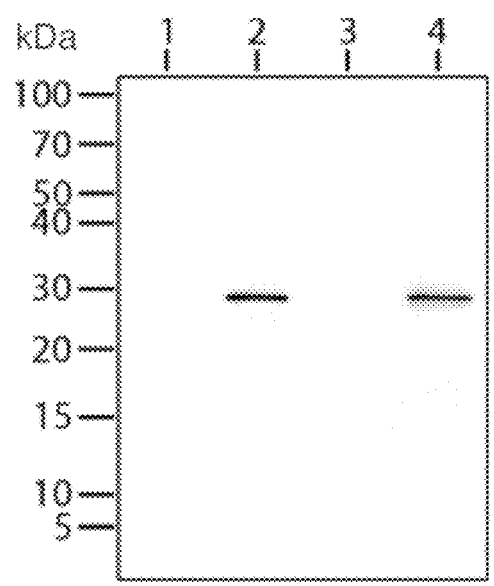
FIG. 4 shows a photograph of a western blot with antibodies directed to the his-tag and conjugated with horseradish peroxidase. Lane 1: post-nuclear supernatant of cells expressing non-his-tagged luciferase from *Neonothopanus nambi*. Lane 2: post-nuclear supernatant of cells expressing his-tagged luciferase from *Neonothopanus nambi*. Lane 3: supernatant obtained by centrifugation at 140000 g. Lane 4: pellet obtained by centrifugation at 140000 g.

*Pichia pink* clones producing luciferase were detected via spraying the colonies with a solution of 3-hydroxyhispidin and visualizing bioluminescence (emitting light) using IVIS Spectrum CT (PerkinElmer). Clones characterized by the highest luminescence intensity were selected. The clones were isolated and grown in 750 ml flasks filled with 250 ml of YPD medium for 72 hours at 30° C. and stirred at 200 rpm. Luciferase-expressing cells were pelleted by centrifugation at 5000 g for 15 minutes at 4° C. The obtained pellet was resuspended in 100 ml of lysing buffer (0.1 M sodium phosphate, 0.1 M KCl, 4 mM EDTA, 2 mM TCEP, 1 mM PMSF, pH 7.4) and processed 20 times at 600 bar using APV2000 high pressure homogenizer (SPX). Lysate was centrifuged at 8000 g for 15 min at 4° C. The obtained post-nuclear supernatant was centrifuged at 140000 g for 2 hours at 4° C. The obtained residue (microsomal fraction) was resuspended in 10 ml of water. The samples were resolved by denaturing polyacrylamide gel electrophoresis according to Laemmli method (10-25% polyacrylamide gel colored with Coomassie Blue) and used for western blot with antibody conjugate directed to his-tag and horseradish peroxidase, with chemiluminescence signal detection. (FIG. 4). Western blot showed specific staining of luciferase moving in the gel in the region of 28 kDa proteins, which roughly corresponds to the expected molecular weight of luciferase from *Neonothopanus nambi*. Also, western blot revealed coprecipitation of recombinant luciferase with a residue obtained by centrifugation at 140000 g.

Example 5. Obtaining Functional Fragments of Luciferases

Open reading frames encoding truncated fragments of luciferase from *Neonothopanus nambi* were obtained using oligonucleotide synthesis. Nucleic acids encoding luciferase fragments with cut N-terminal 6, 9, 12, 15, 21, 25, 31, 33, 35, 37 and 40 amino acid residues were operably fused to a nucleic acid encoding transcription initiation site and his-tag, and then cloned into pET-23 vector using BamHI and HindIII restriction endonucleases. The vector was used to transform *Escherichia coli* cells of BL21-CodonPlus strain (the derivative of Stratagene BL21-Gold high-yield strain). The cells were plated on Petri dishes containing the following medium: 1% NaCl, 1% tryptone, 0.5% yeast extract, 1.5% agar, 100 µg/ml of ampicillin, 100 µg/ml of chloramphenicol and water) and incubated overnight at 37° C. *Escherichia coli* colonies were then sprayed with a solution of luciferin and visualized in IVIS Spectrum CT (PerkinElmer, USA) to determine the functionality of the expressed luciferase fragments. It was found that luciferase fragments with cut N-terminal 6, 9, 12, 15, 21, 25, 31, 33, 35, 37 amino acid residues emit light when sprayed with a solution of luciferin.

The nucleotide and amino acid sequences of the N-terminus, to which luciferase fragments were operably fused, are shown in SEQ ID NO: 52 and 53, correspondingly.

The analysis of amino acid sequence of luciferase from *Neonothopanus narnbi* carried out using software described in TMHMM Server v. 2.0 (Prediction of transmembrane helices in proteins) showed that the first 39 amino acids comprise a transmembrane domain (FIG. 5). Based on the data obtained, it was concluded that removal of the sequence containing a transmembrane domain does not affect the ability of fungal luciferases to catalyze the oxidation of 3-hydroxyhispidin, which is accompanied by light emission.

Using software provided on TMHMM Server v. 2.0 (Prediction of transmembrane helices in proteins), luciferases from *Armillaria gallica, Armillaria mellea, Armillaria ostoyae, Mycena chlorophos, Mycena citricolor, Omphalotus olearius* and *Panellus stipticus*, cloned as described in Example 2, were analyzed. In each case, N-terminal fragments containing transmembrane domains were detected in the amino acid sequence (FIG. 5). The nucleotide and amino acid sequences of luciferase fragments, which were obtained after removal of N-terminal sequences containing transmembrane domains, are shown in SEQ ID NO: 19-34.

Multiple alignment of luciferases is shown in FIG. 5. It can be seen that the proteins contain a non-conserved fragment of 8-11 amino acids in length at the C-terminus. The fragment can also be removed or substituted with other C-terminus without loss of luciferase functionality. It can be also seen that luciferases contain a high-homologous central region containing a consensus sequence shown in SEQ ID NO: 35.

Example 6. Using Luciferase with Other Luciferins

Plasmids comprising coding sequences of fungal luciferases necessary for expression in mammalian cells were obtained as described in Example 3 and used for the transfection of HEK293N cells. 24 hours after the transfection procedure, the cells were detached from dishes using trypsin-Versen solution (0.025% trypsin), the medium was substituted with a phosphate saline buffer, pH 8.0, by centrifugation, the cells were resuspended and lysed using ultrasound; 3-hydroxyhispidin or one of analogs thereof ((E)-6-(4-diethylamino)styryl)-3,4-dihydroxy-2H-pyran-2-one, (E)-3,4-dihydroxy-6-(4-hydroxystyryl)-2H-pyran-2-one, E)-6-(2-1H-indol-3-yl)vinyl)-3,4-dihydroxy-2H-pyran-2-one, (E)-6-(2-(1,2,3,5,6,7-hexahydropyrido[3,2,1-ij] quinoline-9-yl)vinyl)-3,4-dihydroxy-2H-pyran-2-one and (E)-3,4-dihydroxy-6-(2-(6-hydroxynaphthalene-2-yl)vinyl)-2H-pyran-2-one) at a concentration of 660 µg/ml was added to the medium.

Varian Cary Eclipse spectrofluorimeter was used to detect bioluminescence spectra. All the samples emitted light with all examined luciferins. Depending on luciferin used, luminescence optimum displacement was observed as follows: during the oxidation of (E)-3,4-dihydroxy-6-(2-(6-hydroxynaphthalene-2-yl)vinyl)-2H-pyran-2-one, a shift to the long-wavelength region accompanied by a significant emission of photons having a wavelength of more than 580 nm is observed, and during oxidation of (E)-6-(2-1 H-indol-3-yl)vinyl)-3,4-dihydroxy-2H-pyran-2-one, a shift to the short-wavelength region is observed.

Example 7. Obtaining Recombinant Luciferases

Sequence SEQ ID No: 52 was operably linked to the 5' end of the nucleic acids encoding functional fragments of luciferases (SEQ ID NOs: 19, 21, 23, 25, 27, 29, 31, 33); the obtained constructs were cloned into pET-23 vector using BamHI and HindIII restriction endonucleases. The vector was used to transform *Escherichia coli* cells of BL21-CodonPlus strain (the derivative of Stratagene BL21-Gold high-yield strain) The cells were plated on Petri dishes containing LB medium comprising 1.5% agar, 100 µg/ml of ampicillin and 100 µg/ml of chloramphenicol, and incubated overnight at 37° C. *Escherichia coli* colonies were then transferred to 4 ml of liquid LB medium supplemented with ampicillin and chloramphenicol and incubated overnight at 37° C., with rocking. 1 ml of the overnight culture was transferred to 100 ml of Overnight Express Autoinduction medium (Novagen) containing preliminary added ampicillin and chloramphenicol. The culture was grown at 37° C. for 2.5 hours until it reached an optical density of 0.6 OE at 600 nm, and then it was grown at room temperature for 16 hours. The cells were then pelleted by centrifugation at 4500 rpm for 20 minutes in Eppendorf 5810R centrifuge, resuspended in 35 ml of buffer (50 mM Tris HCl, pH 8.0, 150 mM NaCl) and sonicated. The cell lysate was centrifuged at 7500 rpm for 15 minutes, the residue was extracted, and the supernatant was further subjected to centrifugation at 35000 rpm for one hour to separate the microsomal fraction from the soluble fraction. The residue was dissolved overnight at room temperature in 10 ml of buffer containing urea (8M urea, 50 mM Tris, pH 8.0).

Figure 6:
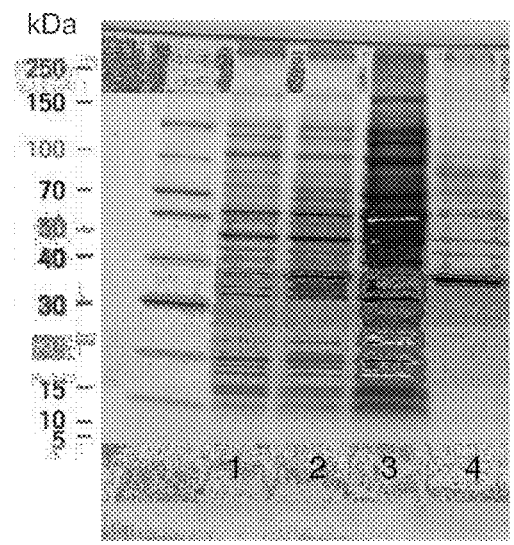
FIG. 6 shows a photograph of Coomassie Blue-stained gradient polyacrylamide gel (10-25%) with *E. coli* lysate before IPTG induction (lane 1); *E. coli* lysate after overnight expression at room temperature (lane 2); supernatant after cell lysis and centrifugation at 35000 g (lane 3); extract from *E. coli* inclusion bodies (lane 4).
Figure 7:
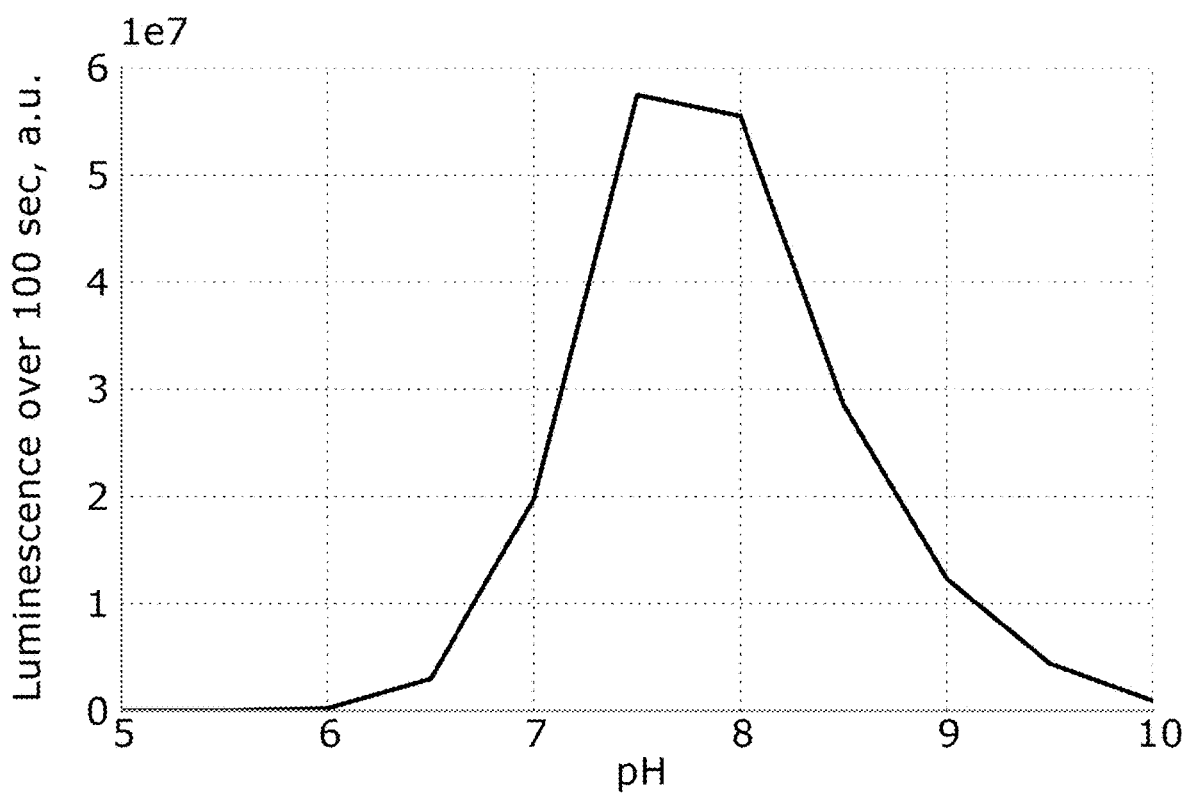
FIG. 7 shows the dependence of bioluminescence intensity of recombinant luciferase from *Neonothopanus nambi* on pH.
Figure 8:
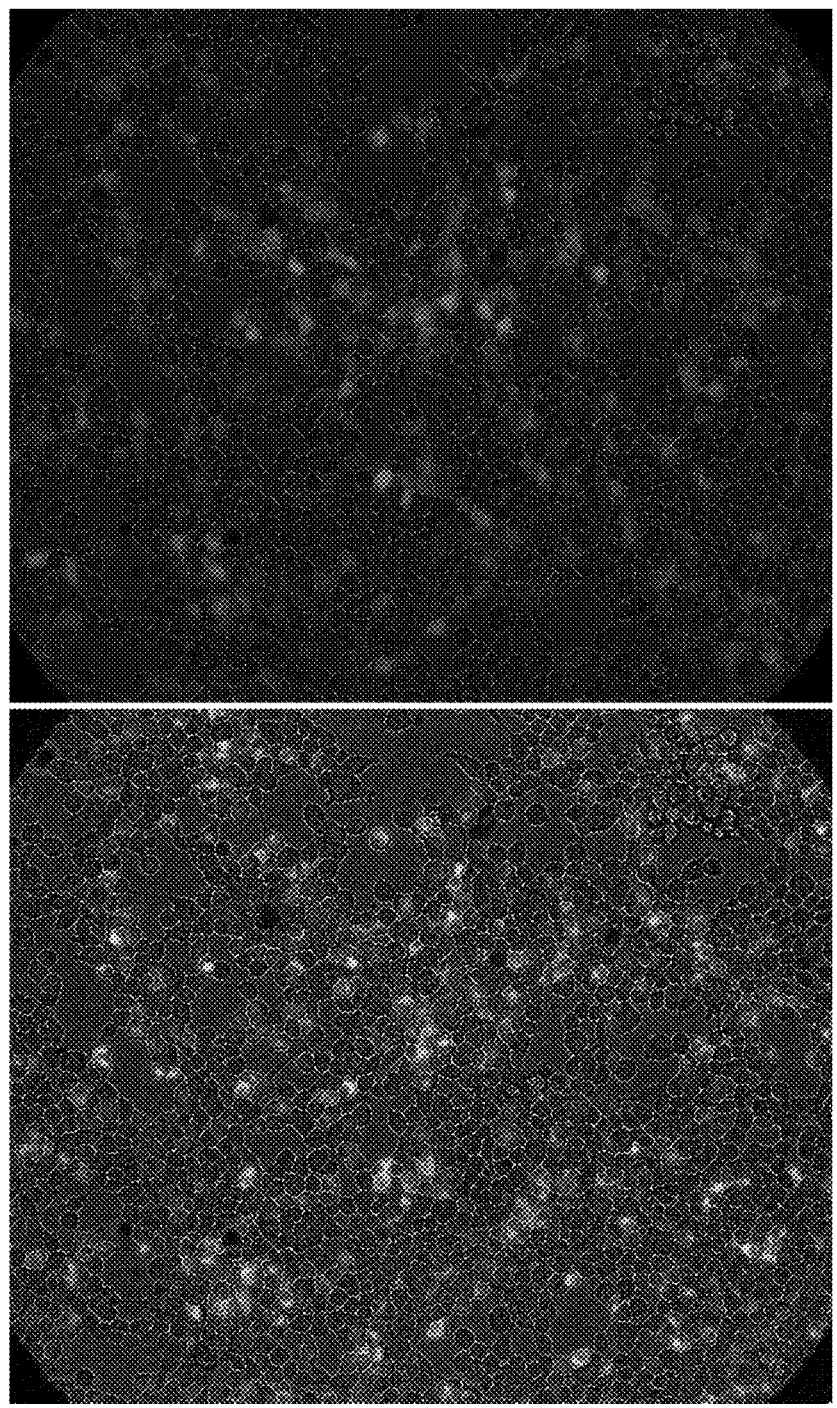
FIG. 8 shows transmission photomicrographs superimposed on photomicrographs taken in the red transmission channel (at the top, mKate2) and the green transmission channel (at the bottom, luciferase).

Presence of the expected recombinant product was verified by electrophoresis. An example of such an analysis for a fragment of luciferase from *Neonothopanus nambi* is shown in FIG. 6. A band in 28 kDa region approximately corresponding to the expected molecular mass of luciferase from *Neonothopanus nambi* can be observed. Aliquots of the isolated recombinant proteins were applied to polyacrylamide gel for electrophoresis. Also, they were used to verify the functionality and stability of recombinant proteins. The isolated recombinant proteins emitted light when 3-hydroxyhispidin was added, with emission maxima within the range of 520-535 nm, where the functional fragment of luciferase from *Neonothopanus nambi* had the highest intensity of emitted light, and that from *Omphalotus olearius* had the lowest intensity. Recombinant proteins were active in buffer solutions, pH 7-9, and showed the maximum intensity of bioluminescence at pH 7.3-8. An example of diagram of dependence of bioluminescence intensity on pH of the solution is shown in FIG. 7.

In order to analyze temperature stability, luciferases were incubated at different temperatures for 10 min, pH 7.4. At the end of incubation, 3-hydroxyhispidin was added to the proteins and bioluminescence intensity was analyzed as described above. Luciferases retained more than 10% of the maximum activity after incubation at temperatures below 50° C., more than 30% of activity at temperatures below 40° C., more than 70% at temperatures below 38° C. and 100% activity at temperatures below 34° C., inclusive Example 8. Using Luciferase from *Neonothopanus nambi* for Cell Labelling Vector containing luciferase from *Neonothopanus nambi* under the control of a cytomegaloviral promoter obtained as described in Example 3 was co-transfected with pTurboFP635-N vector (Evrogen, Russia) encoding the red fluorescent protein, into the cells of HEK293NT line. Transfection was performed using FuGENE HD transfection reagent (Promega) according to the protocol recommended by the manufacturer. 24 hours after the transfection procedure, 3-hydroxyhispidin was added to the medium up to a final concentration of 660 µg/ml; and cell luminescence was analysed using Leica DM6000 microscope with a 20× objective. The cells were visualized in transmitted light, in the green and red channels for detecting fluorescence (FIG. 6). Expression of luciferase from *Neonothopanus nambi* in human cells resulted in a distinct light signal in the green region of the spectrum. No signs of toxicity of luciferase expression to the cells were exhibited.

Example 9. Labelling Proteins Using Luciferase From *Neonothopanus nambi*

A humanized nucleic acid encoding luciferase from *Neonothopanus nambi* obtained as described in Example 3 was operably fused (cloned in-frame) to nucleic acids encoding cytoplasmic beta-actin and human fibrillarin. The obtained constructs were cloned into pmKate2-keratin vector as described in Example 3. 24 hours after the transfection procedure, 3-hydroxyhispidin was added to the culture medium up to a final concentration of 660 µg/ml, and the recorded bioluminescence corresponded to intracellular localization patterns typical of the corresponding cellular proteins.

Example 10. Labelling Organelles Using Luciferase from *Neonothopanus nambi*

A variant of sequence of luciferase from *Neonothopanus nambi* optimized for expression in human cells and obtained as described in Example 3 was operably fused in-frame to the following intracellular localization signals: a mitochondrial targeting signal (MTS) from subunit 7 of human cytochrome oxidase; signal encoded by the N-terminal 81 amino acids of human beta 1-4 galactosyltransferase [Watzele and Berger, Nucleic Acids. Res., 1990, 18:7174]; peroxisomal targeting signal [Gould et al. J. Biol. Chem., 1989, 108: 1657-1664; Gould et al. EMBO J., 1990, 9: 85-90; Monosov et al., J. Histo. Cytochem., 1996, 44: 581-589]; three copies of nuclear localization signal (NLS) of SV40 T antigen [Kalderon et al., Cell, 1984, 39: 499-509; Lanford et al., Cell, 1986, 46: 575-582]. Transfection of HeLa Kyoto cells with plasmids expressing chimeric constructs with luciferase from *Neonothopanus nambi* resulted in an efficient transfer of chimeric proteins to the corresponding organelles within the cells. Bioluminescence was detected 24 hours after transfection with the addition of 3-hydroxyhispidin to the medium at a final concentration of 660 µg/ml.

Example 11. Labelling Cells within Whole Organism

Vector containing the coding sequence of luciferase from *Neonothopanus nambi* under the control of a cytomegaloviral promoter was obtained as described in Example 3. In addition, a humanized nucleotide sequence encoding luciferase from *Photinus pyralis* firefly was synthesized and cloned into the same vector.

The obtained constructs were used to transfect CT26 cells (*Mus musculus* carcinoma cells). The cells expressing luciferase from *Neonothopanus nambi* were injected subcutaneously into the left half of a mouse's back, while cells expressing luciferase of *Photinus pyralis* were injected in the same manner into the right half of a mouse's back. 10 minutes after injection, a mixture of fungal luciferin (0.5 mg) and *Photinus pyralis* firefly luciferin (0.5 mg) was injected intraperitoneally. Bioluminescence of the mouse was then visualized using IVIS Spectrum CT (PerkinElmer). The tumour expressing luciferase from *Neonothopanus*

Figure 9:
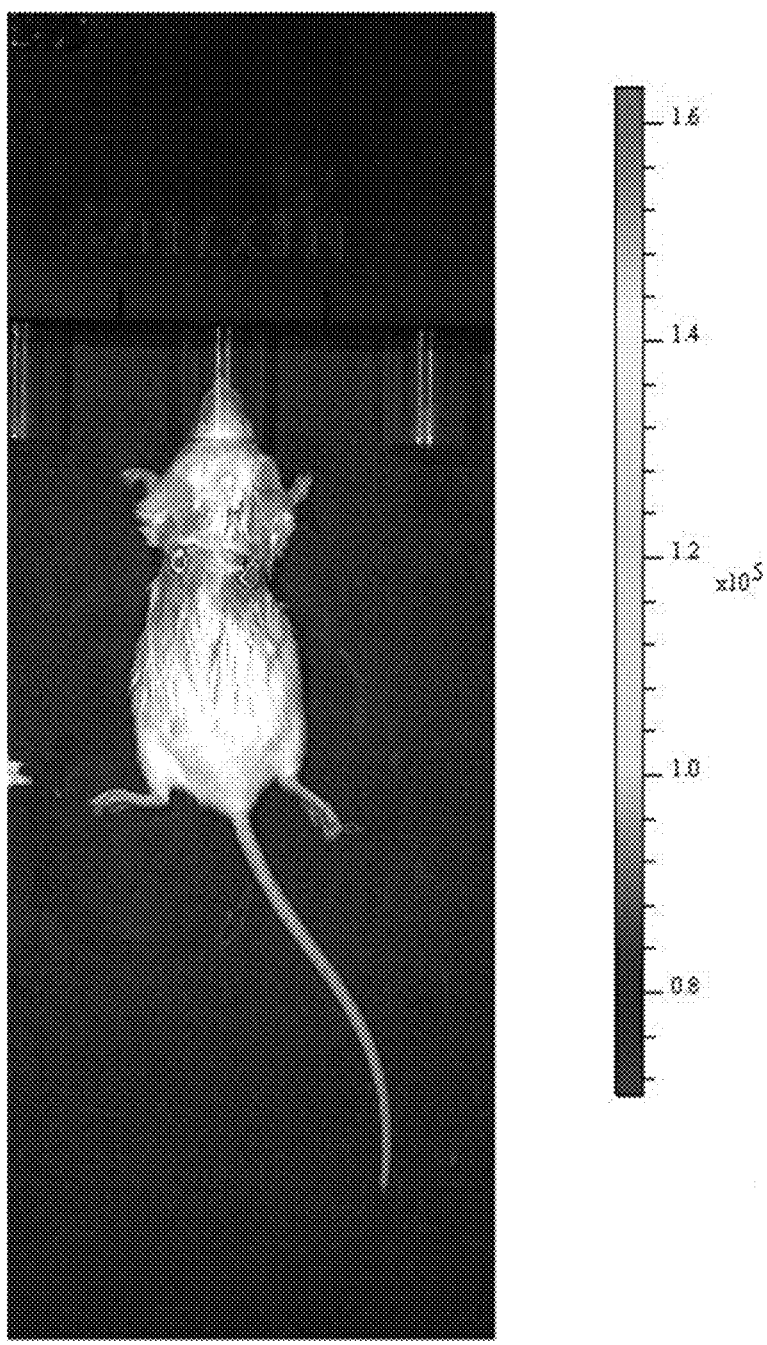
FIG. 9 shows labelling of tumour cells in a living mouse using luciferase from *Neonothopanus nambi* (implanted in the left half of the mouse's back) and *Photinus pyralis* luciferase (implanted in the right half). Superimposition of mouse photographs and recorded light signal coming from the implanted tumours is shown.
Figure 10:
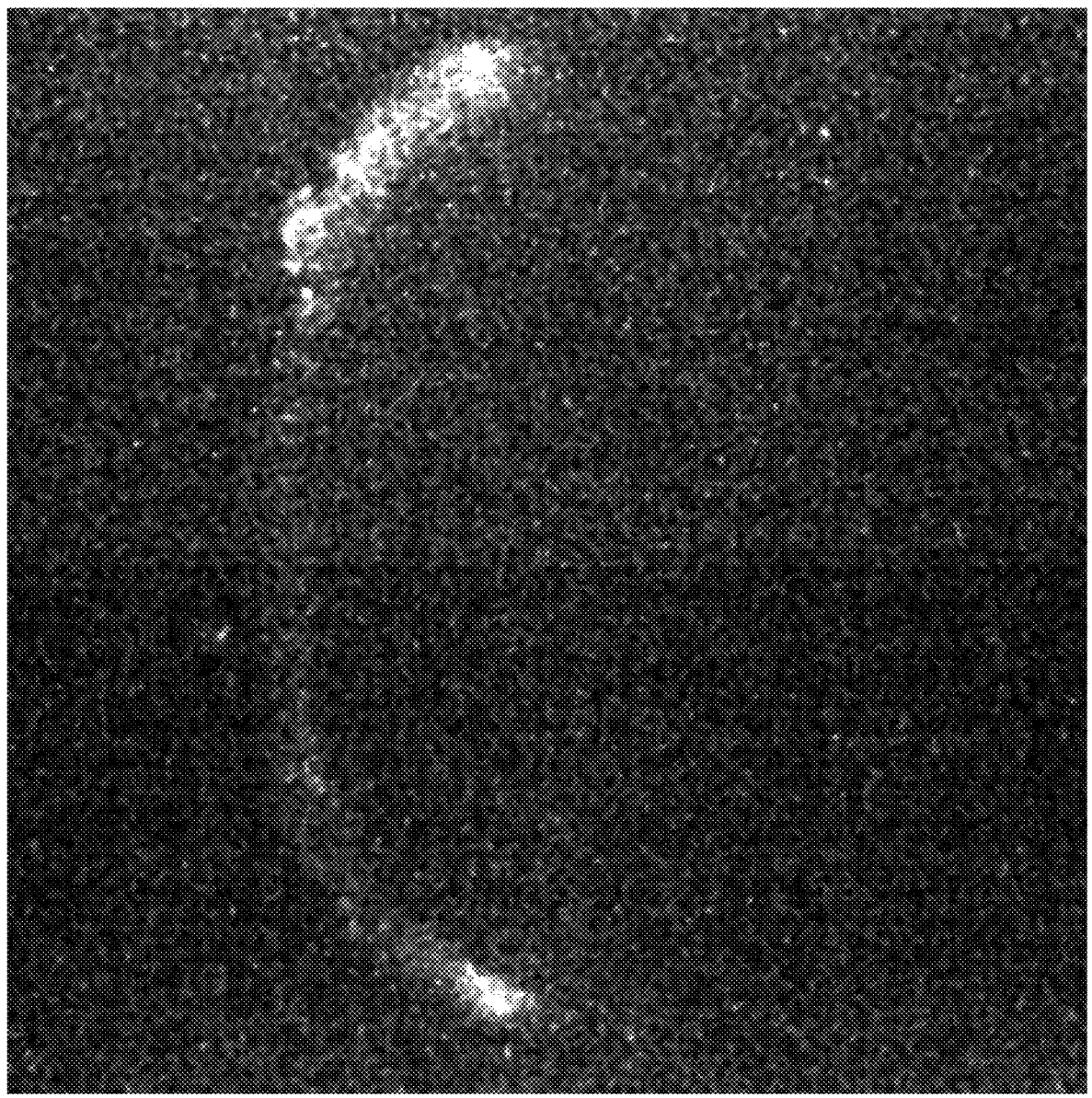
FIG. 10 shows labelling of the nervous system of a *Xenopus laevis* embryo in neurulation (stages 16-17) with the help of luciferase from *Neonothopanus nambi*. Luciferase bioluminescence is shown.

*nambi* exhibited the intensity of light emission at 20000000 cu, and the tumour expressing luciferase from *Photinus pyralis* exhibited that at 21000000 cu (FIG. 9).

mRNA of luciferase from *Neonothopanus nambi* was obtained via in vitro transcription of Acc65I linearized pCS2+ vector comprising a luciferase gene using SP6 polymerase from SP6 mMessage mMachine Kits (Ambion, USA). mRNA was further purified by CleanRNA Standard Kit (Evrogen) and injected into both blastomeres of two-cell *Xenopus laevis* embryos, 500 μg of mRNA per blastomere. For visualization, a 660 μg/ml luciferin solution was injected into blastocoel of the embryos at the early gastrula stage (stage 10.5). Embryo luminescence after rhodamine staining was detected during neurulation (stages 16-17) using Leica DM6000 microscope, in green and red fluorescence detection channels of the microscope, with a 5× objective (FIG. 10). The bioluminescent signal was detected in the nerve tissue of the embryo.

Example 12. Preparing Polyclonal Antibodies

The coding sequence of luciferase from *Neonothopanus nambi* with a deleted transmembrane domain shown in SEQ ID No: 19 was synthetically obtained as a double-stranded DNA and cloned into pQE-30 expression vector (Qiagen, Germany) in such a way that the N-terminus of the resulting recombinant protein contained a his-tag. After expression in *E. coli*, the recombinant protein was purified with a metal-affinity TALON resin (Clontech) under denaturing conditions. The purified protein preparation emulsified in Freund's adjuvant was used for four immunizations of rabbits at monthly intervals. The rabbit's blood was withdrawn on the tenth or eleventh days after immunizations. Activity of the obtained polyclonal antiserum was demonstrated by the recombinant protein using ELISA and Western immunoblotting methods.

Example 13. Obtaining Transgenic Plants

The coding sequence of luciferase from *Neonothopanus nambi* was optimized for expression as in *Physcomitrella patens* moss cells (SEQ ID NO: 54). A transcriptional unit containing the promoter of aktI gene of rice, 5'-untranslated region of human cytomegalovirus, a coding sequence of luciferase, a stop codon, and a terminator sequence from the *Agrobacterium tumefaciens* osc gene was then created in silico. The obtained sequence was generated synthetically and cloned using Gibson Assembly [Gibson et al., Nat Methods, 2009, 6: 343-5] method into pLand #1 expression vector between DNA fragments corresponding with the locus of genomic DNA of *Physcomitrella patens* moss between the sequences of highly expressed moss genes: Pp3c16_6440V3.1 and Pp3c16-6460V3.1. pLand #1 vector also contained a sequence of guide RNA (sgRNA) for Cas9 nuclease, which was complementary to the same DNA locus region.

The plasmid DNA preparation was cotransformed with the expression vector containing Cas9 nuclease sequence into *Physcotmitrella patens* protoplasts according to the polyethylene glycol transformation protocol described in [Cove et al., Cold Spring Harb Protoc., 2009, 2]. The protoplasts were then incubated in BCD medium for two days in the dark, shaking at 50 rpm to regenerate the cell wall. The protoplasts were then transferred to Petri dishes containing agar and BCD medium and grown under 16-hour illumination for a week. The transformed moss colonies were screened from external genomic primers by PCR to evaluate integration of the genetic construct into the genome, transferred to fresh Petri dishes and grown under the same illumination conditions for 30 days.

The obtained moss gametophytes were soaked in BCD medium containing 3-hydroxyhispidin at a concentration of 660 μg/ml and analyzed by IVIS Spectrum In Vivo Imaging System (Perkin Elmer). All sample transgenic plants exhibited bioluminescence with an intensity at least two orders of magnitude greater than the signal strength of wild-type control plants incubated in the same solution containing 3-hydroxyhispidin.

Example 14. Obtaining Transgenic Animals

Transgenic fishes (*Danio rerio*) containing the gene of luciferase from *Neonothopanus nambi* were created according to the method described in [Hisano et al., Sci Rep., 2015, 5:8841]. In order to create transgenic animals, DNA fragments containing the sequences of guide RNA and mRNA of Cas9 nuclease under the control of T7 bacteriophage polymerase promoter were synthesized. The obtained fragments were used for in vitro transcription using reagents from MAXIscript T7 kit (Life Technologies, USA), and the synthesized RNA was purified using an RNA isolation kit (Evrogen, Russia). A donor vector sequence containing the gene of luciferase from *Neonothopanus nambi*, flanked by 50 nucleotide sequences from krtt1c19e *Danio rerio* gene, was also obtained synthetically. The donor vector, mRNA of Cas9 nuclease and guide RNA were dissolved in injection buffer (40 mM HEPES, pH 7.4, 240 mM KCl with the addition of 0.5% phenolic red) and injected into 1-2-cell *Danio rerio* embryos in a volume of about 1-2 nl. About 50 out of 70 embryos survived injection and exhibited normal development on the fourth day after fertilization.

In order to record the bioluminescent signal, a solution of 3-hydroxyhispidin was injected intravenously into *Danio rerio* larvae according to the procedure described in [Cosentino et al., J Vis Exp. 2010; (42): 2079]. Bioluminescence was recorded using IVIS Spectrum In Vivo Imaging System (Perkin Elmer). After measurement, genomic DNA was isolated from the larvae to verify integration of the luciferase gene into the genome. All larvae with correct genome integration of the gene of luciferase from *Neonothopanus nambi* exhibited bioluminescence with intensity at least an order of magnitude greater than that of the signal from wild-type fish after injection of the 3-hydroxyhispidin solution.

All publications and patent applications herein are incorporated by reference to the same extent as if each individual publication or patent application was specifically and individually indicated to be incorporated by reference. Citation of each publication is offered by way of illustration and may be useful in understanding the present invention. It is not an admission that any publication specifically or implicitly referenced is prior art.

What is claimed is:

1. An isolated nucleic acid encoding a luciferase, having an amino acid sequence at least 95% identical to that of SEQ ID NO: 2.

2. An expression cassette comprising the nucleic acid molecule of claim 1 under the control of regulatory elements required for nucleic acid expression in the host cell, which, being integrated into the cell genome or introduced into the cell in the form of an extrachromosomal element, is capable of providing the expression of luciferase encoded by the nucleic acid.

3. A cell producing luciferase encoded by the nucleic acid of claim 1, comprising an expression cassette comprising the nucleic acid under the control of regulatory elements required for nucleic acid expression in the host cell, which, being integrated into the cell genome or introduced into the cell in the form of an extrachromosomal element, is capable of providing the expression of luciferase encoded by the nucleic acid in the form of an extrachromosomal element or an element integrated into the cell genome.

4. A kit containing:
   nucleic acid of claim 1, and
   luciferin capable of being oxidized by luciferase.

5. An expression cassette comprising the nucleic acid molecule of claim 1 operably fused to an intracellular localization signal, under the control of regulatory elements, required for the expression of the nucleic acid in the host cell, which, being integrated into the cell genome or introduced into the cell in the form of an extrachromosomal element, is capable of providing the expression of luciferase encoded by the nucleic acid, linked to the intracellular localization signal.

6. A kit containing:
   the expression cassette of claim 2, and
   luciferin capable of being oxidized by luciferase.

* * * * *

SEQUENCE LISTING

<160> NUMBER OF SEQ ID NOS: 54

<210> SEQ ID NO 1
<211> LENGTH: 801
<212> TYPE: DNA
<213> ORGANISM: Neonothopanus nambi

<400> SEQUENCE: 1

| | | | | | |
|---|---|---|---|---|---|
| atgcgcatta | acattagcct | ctcgtctctc | ttcgaacgtc | tctccaaact | tagcagtcgc | 60 |
| agcatagcga | ttacatgtgg | agttgttctc | gcctccgcaa | tcgcctttcc | catcatccgc | 120 |
| agagactacc | agactttcct | agaagtggga | ccctcgtacg | ctccgcagaa | ctttagagga | 180 |
| tacatcatcg | tctgtgtcct | ctcgctattc | cgccaagagc | agaaagggct | cgccatctat | 240 |
| gatcgtcttc | ccgagaaacg | caggtggttg | gccgaccttc | cctttcgtga | aggaaccaga | 300 |
| cccagcatta | ccagccatat | cattcagcga | cagcgcactc | aactggtcga | tcaggagttt | 360 |
| gccaccaggg | agctcataga | caaggtcatc | cctcgcgtgc | aagcacgaca | caccgacaaa | 420 |
| acgttcctca | gcacatcaaa | gttcgagttt | catgcgaagg | ccatatttct | cttgccttct | 480 |
| atcccaatca | acgaccctct | gaatatccct | agccacgaca | ctgtccgccg | aacgaagcgc | 540 |
| gagattgcac | atatgcatga | ttatcatgat | tgcacacttc | atcttgctct | cgctgcgcag | 600 |
| gatggaaagg | aggtgctgaa | gaaaggttgg | ggacaacgac | atcctttggc | tggtcctgga | 660 |
| gttcctggtc | caccaacgga | atggactttt | ctttatgcgc | tcgcaacga | agaagaggct | 720 |
| cgagtagtgg | agatgatcgt | tgaggcttcc | atagggtata | tgacgaacga | tcctgcagga | 780 |
| aagattgtag | aaaacgccaa | g | | | | 801 |

<210> SEQ ID NO 2
<211> LENGTH: 267
<212> TYPE: PRT
<213> ORGANISM: Neonothopanus nambi

<400> SEQUENCE: 2

Met Arg Ile Asn Ile Ser Leu Ser Ser Leu Phe Glu Arg Leu Ser Lys
1               5                   10                  15

Leu Ser Ser Arg Ser Ile Ala Ile Thr Cys Gly Val Val Leu Ala Ser
            20                  25                  30

Ala Ile Ala Phe Pro Ile Ile Arg Arg Asp Tyr Gln Thr Phe Leu Glu
        35                  40                  45

Val Gly Pro Ser Tyr Ala Pro Gln Asn Phe Arg Gly Tyr Ile Ile Val
    50                  55                  60

Cys Val Leu Ser Leu Phe Arg Gln Glu Gln Lys Gly Leu Ala Ile Tyr
65                  70                  75                  80

Asp Arg Leu Pro Glu Lys Arg Arg Trp Leu Ala Asp Leu Pro Phe Arg
                85                  90                  95

Glu Gly Thr Arg Pro Ser Ile Thr Ser His Ile Ile Gln Arg Gln Arg
            100                 105                 110

Thr Gln Leu Val Asp Gln Glu Phe Ala Thr Arg Glu Leu Ile Asp Lys
        115                 120                 125

Val Ile Pro Arg Val Gln Ala Arg His Thr Asp Lys Thr Phe Leu Ser
    130                 135                 140

Thr Ser Lys Phe Glu Phe His Ala Lys Ala Ile Phe Leu Leu Pro Ser
145                 150                 155                 160

Ile Pro Ile Asn Asp Pro Leu Asn Ile Pro Ser His Asp Thr Val Arg
                165                 170                 175

```
Arg Thr Lys Arg Glu Ile Ala His Met His Asp Tyr His Asp Cys Thr
            180                 185                 190

Leu His Leu Ala Leu Ala Ala Gln Asp Gly Lys Glu Val Leu Lys Lys
            195                 200                 205

Gly Trp Gly Gln Arg His Pro Leu Ala Gly Pro Gly Val Pro Gly Pro
        210                 215                 220

Pro Thr Glu Trp Thr Phe Leu Tyr Ala Pro Arg Asn Glu Glu Glu Ala
225                 230                 235                 240

Arg Val Val Glu Met Ile Val Glu Ala Ser Ile Gly Tyr Met Thr Asn
                245                 250                 255

Asp Pro Ala Gly Lys Ile Val Glu Asn Ala Lys
            260                 265
```

<210> SEQ ID NO 3
<211> LENGTH: 798
<212> TYPE: DNA
<213> ORGANISM: Armillaria gallica

<400> SEQUENCE: 3

```
atgtccttca tcgacagcat gaaacttgac ctcgtcggac acctctttgg catcaggaat      60
cgcggcttag ccgccgcttg ttgtgctcta gcagtcgcct ctactatcgc cttcccttac     120
attcgtaggg actaccagac attttttatct ggcggtccct cttacgctcc ccagaatatc    180
agaggatatt tcatcgtctg cgttctggcc ttgttccgtc aggagcaaaa gggccttgcg     240
atatatgatc gccttcccga gaagcgcagg tggctgcctg acttgcctcc tcgcaatggc     300
ccgcggccga tcacgaccag ccatataatc aaagacagc gcaaccaggc gccggacccc      360
aagttcgccc tcgaggaact caaggccacg gttattccac gggtgcaggc tcgccatact     420
gacctcaccc catctcagcct atccaaattc gagttccatg ctgaagcaat tttcctgctc    480
ccctctgtac ccatcgatga tccaaaaaat gttccaagtc acgacacggt gcgcaggacg    540
aaaagggaga tcgcgcatat gcacgactac catgacttca cgctgcatct tgcactggcc    600
gcccaagacg ggaaggaagt cgtgtcgaag ggatgggggc agcgacaccc cctagcaggc    660
cctggcgttc ctggtccacc tacggagtgg acatttattt atgcgccacg taacgaagag    720
gaactggcag tggtggaaat gattatcgag gcatcaatag gctatatgac caatgaccct   780
gctggagtag ttatcgca                                                 798
```

<210> SEQ ID NO 4
<211> LENGTH: 266
<212> TYPE: PRT
<213> ORGANISM: Armillaria gallica

<400> SEQUENCE: 4

```
Met Ser Phe Ile Asp Ser Met Lys Leu Asp Leu Val Gly His Leu Phe
1               5                  10                  15

Gly Ile Arg Asn Arg Gly Leu Ala Ala Ala Cys Cys Ala Leu Ala Val
            20                  25                  30

Ala Ser Thr Ile Ala Phe Pro Tyr Ile Arg Arg Asp Tyr Gln Thr Phe
            35                  40                  45

Leu Ser Gly Gly Pro Ser Tyr Ala Pro Gln Asn Ile Arg Gly Tyr Phe
        50                  55                  60

Ile Val Cys Val Leu Ala Leu Phe Arg Gln Glu Gln Lys Gly Leu Ala
65                  70                  75                  80

Ile Tyr Asp Arg Leu Pro Glu Lys Arg Arg Trp Leu Pro Asp Leu Pro
                85                  90                  95
```

```
Pro Arg Asn Gly Pro Arg Pro Ile Thr Thr Ser His Ile Ile Gln Arg
            100                 105                 110
Gln Arg Asn Gln Ala Pro Asp Pro Lys Phe Ala Leu Glu Glu Leu Lys
            115                 120                 125
Ala Thr Val Ile Pro Arg Val Gln Ala Arg His Thr Asp Leu Thr His
            130                 135                 140
Leu Ser Leu Ser Lys Phe Glu Phe His Ala Glu Ala Ile Phe Leu Leu
145                 150                 155                 160
Pro Ser Val Pro Ile Asp Pro Lys Asn Val Pro Ser His Asp Thr
                165                 170                 175
Val Arg Arg Thr Lys Arg Glu Ile Ala His Met His Asp Tyr His Asp
            180                 185                 190
Phe Thr Leu His Leu Ala Leu Ala Ala Gln Asp Gly Lys Glu Val Val
            195                 200                 205
Ser Lys Gly Trp Gly Gln Arg His Pro Leu Ala Gly Pro Gly Val Pro
            210                 215                 220
Gly Pro Pro Thr Glu Trp Thr Phe Ile Tyr Ala Pro Arg Asn Glu Glu
225                 230                 235                 240
Glu Leu Ala Val Val Glu Met Ile Ile Glu Ala Ser Ile Gly Tyr Met
                245                 250                 255
Thr Asn Asp Pro Ala Gly Val Val Ile Ala
            260                 265

<210> SEQ ID NO 5
<211> LENGTH: 801
<212> TYPE: DNA
<213> ORGANISM: Armillaria mellea

<400> SEQUENCE: 5
atgtccttct tcgacagcgt gaaacttgac ctcgtcggac gcctctttgg catcaggaat      60
cgcggcttag ctgttacttg ttgtgctgtg gcagtcgcct ctatcatcgc gttcccttac     120
attcgtaggg actaccagac attttatct gggggtccct cctacgctcc ccagaacatc     180
agaggatacc tcattgtctg cgtcctggcc ttgttccgtc aggagcaaaa aggccttgcg     240
atatacgacc gccttcccga gaagcgcagg tggctacctg acttgcctcc tcgcgatggc     300
ccacggccca tcacgaccag ccatataatc aaagacagc gcaaccaggc gccgaccctc     360
aagttcgccc tcgaggaact caaggccacg gtcattccac gggtgcaggc tcgccacact     420
gacctcaccc catctcagcct atccaagttc gagttccatg ctgaagcaat cttcctgctc     480
ccctctgtac ccatcgatga tccaaagaat gtgccaagtc acgacacggt gcgcaggacg     540
aagagggaaa ttgcgcatat gcacgactac catgactaca cgctgcatct tgcgttggcc     600
gcccaagacg ggaaggaagt cgtatcaaag ggatgggggc agcgacaccc gctggcaggc     660
cctggcgttc ctggtccacc gacggagtgg acgtttattt atgcgccacg taacgaagag     720
gagctggcag tggtggaaat gattatcgag gcatcgatag ctatatgac caatgaccct     780
gcaggaaaaa ctatcgcata g                                               801

<210> SEQ ID NO 6
<211> LENGTH: 266
<212> TYPE: PRT
<213> ORGANISM: Armillaria mellea

<400> SEQUENCE: 6

Met Ser Phe Phe Asp Ser Val Lys Leu Asp Leu Val Gly Arg Leu Phe
```

```
              1               5              10              15
            Gly Ile Arg Asn Arg Gly Leu Ala Val Thr Cys Cys Ala Val Ala Val
                            20              25              30
            Ala Ser Ile Ile Ala Phe Pro Tyr Ile Arg Arg Asp Tyr Gln Thr Phe
                            35              40              45
            Leu Ser Gly Gly Pro Ser Tyr Ala Pro Gln Asn Ile Arg Gly Tyr Leu
                        50              55              60
            Ile Val Cys Val Leu Ala Leu Phe Arg Gln Glu Gln Lys Gly Leu Ala
             65             70              75                  80
            Ile Tyr Asp Arg Leu Pro Glu Lys Arg Arg Trp Leu Pro Asp Leu Pro
                            85              90              95
            Pro Arg Asp Gly Pro Arg Pro Ile Thr Thr Ser His Ile Ile Gln Arg
                        100             105             110
            Gln Arg Asn Gln Ala Pro Asp Leu Lys Phe Ala Leu Glu Glu Leu Lys
                        115             120             125
            Ala Thr Val Ile Pro Arg Val Gln Ala Arg His Thr Asp Leu Thr His
                        130             135             140
            Leu Ser Leu Ser Lys Phe Glu Phe His Ala Glu Ala Ile Phe Leu Leu
             145             150             155                 160
            Pro Ser Val Pro Ile Asp Asp Pro Lys Asn Val Pro Ser His Asp Thr
                            165             170             175
            Val Arg Arg Thr Lys Arg Glu Ile Ala His Met His Asp Tyr His Asp
                            180             185             190
            Tyr Thr Leu His Leu Ala Leu Ala Ala Gln Asp Gly Lys Glu Val Val
                        195             200             205
            Ser Lys Gly Trp Gly Gln Arg His Pro Leu Ala Gly Pro Gly Val Pro
                        210             215             220
            Gly Pro Pro Thr Glu Trp Thr Phe Ile Tyr Ala Pro Arg Asn Glu Glu
             225             230             235                 240
            Glu Leu Ala Val Val Glu Met Ile Ile Glu Ala Ser Ile Gly Tyr Met
                            245             250             255
            Thr Asn Asp Pro Ala Gly Lys Thr Ile Ala
                            260             265

<210> SEQ ID NO 7
<211> LENGTH: 801
<212> TYPE: DNA
<213> ORGANISM: Armillaria ostoyae

<400> SEQUENCE: 7
atgtccttca tcgacagcat gaaacttgac ttcgtcggac acctctttgg catcaggaat      60
cgcggcttag ccaccgcttg ttgtgctgtg gcagtcgctt ctgccatcgc cttcccttac     120
attcgtaggg actaccagac attcttatct ggcggtccct cttacgctcc ccagaacatc     180
aaaggatatc tcatcgtctg cgtcctggcc ttgttccgtc aggagcaaaa gggccttgcg     240
atatatgacc gccttcccga gaagcgcagg tggctacctg acttgcctcc tcgcaatggc     300
ccgcggccca tcacgaccag ccatataatc caaagacagc gcaaccaggc gccagactcc     360
aagttcgccc tcgaggaact caaggctacg gtcattccac gggtgcaggc tcgccacact     420
gacctcaccc atctcagcct atccaagttc gagttccatg ctgaagcaat cttcctgctc     480
ccctctgtac ccatcgatga tccaaaaaat gttccaagtc atgacacggt gcgcaggacg     540
aagagggaga tcgcgcatat gcacgactac atgactttta cgttcatct tgcactggcc     600 gcccaagacg ggaaggaagt cgtggcgaag ggatgggggc agcgacaccc gctggcaggc     660
```

```
cctggcgttc ctggtccacc tacggagtgg acgtttattt atgcgccacg taacgaagag      720
gaactggcag tggtggaaat gattatcgag gcatcaatag gctatatgac caatgaccct      780
gctggaacag ttatcgtata g                                                801
```

<210> SEQ ID NO 8
<211> LENGTH: 266
<212> TYPE: PRT
<213> ORGANISM: Armillaria ostoyae

<400> SEQUENCE: 8

```
Met Ser Phe Ile Asp Ser Met Lys Leu Asp Phe Val Gly His Leu Phe
1               5                   10                  15

Gly Ile Arg Asn Arg Gly Leu Ala Thr Ala Cys Cys Ala Val Ala Val
            20                  25                  30

Ala Ser Ala Ile Ala Phe Pro Tyr Ile Arg Arg Asp Tyr Gln Thr Phe
        35                  40                  45

Leu Ser Gly Gly Pro Ser Tyr Ala Pro Gln Asn Ile Lys Gly Tyr Leu
    50                  55                  60

Ile Val Cys Val Leu Ala Leu Phe Arg Gln Glu Gln Lys Gly Leu Ala
65                  70                  75                  80

Ile Tyr Asp Arg Leu Pro Glu Lys Arg Arg Trp Leu Pro Asp Leu Pro
                85                  90                  95

Pro Arg Asn Gly Pro Arg Pro Ile Thr Thr Ser His Ile Ile Gln Arg
            100                 105                 110

Gln Arg Asn Gln Ala Pro Asp Ser Lys Phe Ala Leu Glu Glu Leu Lys
        115                 120                 125

Ala Thr Val Ile Pro Arg Val Gln Ala Arg His Thr Asp Leu Thr His
    130                 135                 140

Leu Ser Leu Ser Lys Phe Glu Phe His Ala Glu Ala Ile Phe Leu Leu
145                 150                 155                 160

Pro Ser Val Pro Ile Asp Asp Pro Lys Asn Val Pro Ser His Asp Thr
                165                 170                 175

Val Arg Arg Thr Lys Arg Glu Ile Ala His Met His Asp Tyr His Asp
            180                 185                 190

Phe Thr Leu His Leu Ala Leu Ala Ala Gln Asp Gly Lys Glu Val Val
        195                 200                 205

Ala Lys Gly Trp Gly Gln Arg His Pro Leu Ala Gly Pro Gly Val Pro
    210                 215                 220

Gly Pro Pro Thr Glu Trp Thr Phe Ile Tyr Ala Pro Arg Asn Glu Glu
225                 230                 235                 240

Glu Leu Ala Val Val Glu Met Ile Ile Glu Ala Ser Ile Gly Tyr Met
                245                 250                 255

Thr Asn Asp Pro Ala Gly Thr Val Ile Val
            260                 265
```

<210> SEQ ID NO 9
<211> LENGTH: 753
<212> TYPE: DNA
<213> ORGANISM: Mycena chlorophos

<400> SEQUENCE: 9

```
atggtccaac tcacccgaac ctccggattc atcgccgctg cggccattgt tgctgccatc       60
gccttcccgt tcattcgtcg agactaccag acgttccttc gtggtgggcc gtcctatgcc      120
ccacagaaca tccgcggcta tatcatcgtc ctggttctgt ccctcttccg cggcgaggag      180
```

```
aagggtcttg caatctacga gccccttcct gagaagcgca catggctgcc ggagcttccg    240
cggcgcgcgg gagaccggcc caagacgacg agccacatca tccaacggca gctcgaccag    300
taccccgacc cggactttgt cctcaaagcc ctgaaagcga cggtcatccc gcgtgtccaa    360
gcccggcaca cagacaagac tcacctcgcg ctgtccaagt tcgagttcca tgctgaggcc    420
atcttcgtgc gcccggaaat cgccatcgac gacccgaagc atatcccag ccacgacacg     480 gtgcgacgga cgaagcgcga gattgcgcac atgcacgact atcacgactg cacgctgcat    540
ttggcgctag cggcgcagga cgcgaagcag gtgctgcaga agggctgggg ccagcgccat    600
ccgctggcag ggcctgggat gccgggccg cccacggagt ggacgttctt gtatgccccg     660
aggaccgagg aggaagtgaa ggttgtggag accattgtcg aggcctctat cgcgtacatg    720
acgaacgcgg agaagccggt cgagctggtg cag                                 753
```

<210> SEQ ID NO 10
<211> LENGTH: 251
<212> TYPE: PRT
<213> ORGANISM: Mycena chlorophos

<400> SEQUENCE: 10

```
Met Val Gln Leu Thr Arg Thr Ser Gly Phe Ile Ala Ala Ala Ile
1               5                   10                  15

Val Ala Ala Ile Ala Phe Pro Phe Ile Arg Arg Asp Tyr Gln Thr Phe
            20                  25                  30

Leu Arg Gly Gly Pro Ser Tyr Ala Pro Gln Asn Ile Arg Gly Tyr Ile
        35                  40                  45

Ile Val Leu Val Leu Ser Leu Phe Arg Gly Glu Glu Lys Gly Leu Ala
    50                  55                  60

Ile Tyr Glu Pro Leu Pro Glu Lys Arg Thr Trp Leu Pro Glu Leu Pro
65                  70                  75                  80

Arg Arg Ala Gly Asp Arg Pro Lys Thr Thr Ser His Ile Ile Gln Arg
                85                  90                  95

Gln Leu Asp Gln Tyr Pro Asp Pro Asp Phe Val Leu Lys Ala Leu Lys
            100                 105                 110

Ala Thr Val Ile Pro Arg Val Gln Ala Arg His Thr Asp Lys Thr His
        115                 120                 125

Leu Ala Leu Ser Lys Phe Glu Phe His Ala Glu Ala Ile Phe Val Arg
    130                 135                 140

Pro Glu Ile Ala Ile Asp Asp Pro Lys His Ile Pro Ser His Asp Thr
145                 150                 155                 160

Val Arg Arg Thr Lys Arg Glu Ile Ala His Met His Asp Tyr His Asp
                165                 170                 175

Cys Thr Leu His Leu Ala Leu Ala Ala Gln Asp Ala Lys Gln Val Leu
            180                 185                 190

Gln Lys Gly Trp Gly Gln Arg His Pro Leu Ala Gly Pro Gly Met Pro
        195                 200                 205

Gly Pro Pro Thr Glu Trp Thr Phe Leu Tyr Ala Pro Arg Thr Glu Glu
    210                 215                 220

Glu Val Lys Val Val Glu Thr Ile Val Glu Ala Ser Ile Ala Tyr Met
225                 230                 235                 240

Thr Asn Ala Glu Lys Pro Val Glu Leu Val Gln
                245                 250
```

<210> SEQ ID NO 11

<211> LENGTH: 738
<212> TYPE: DNA
<213> ORGANISM: Mycena citricolor

<400> SEQUENCE: 11

```
atggcttatc agctcacttg gattcagact ctcgtgctgg gtgcccttgt ggcaatggca      60
gtagcgttcc ccttcatcaa gaaagactac gagacgttcc tgaagggcgg ccctcctat     120
gcgccccaaa acgttcgcgg atacatcatc gtgctcgtgc tcgcgctctt ccgcaagag     180
cagctcgggc tggagatcta cgaccgcatg cccgagaaac gtcgctggct cgcgaatctc    240
cctcagcgcg agggcccccg ccccaagacc acaagtcaca tcatccagcg gcagctcagc    300
cagcacacgg accccgcatt cggcgccgcg tacctcaaag acaccgtcat tccgcgcgtc    360
caggcgcggc acgcagccaa cacgcacatc gcgcgctcga cgttcgagtt ccacgccgcc    420
gcgatcttcc tgaacgcgga cgtgccgctg cccgagggcc tgcccgcaag cgagacggtg    480
cggcggacca agggcgagat cgcgcacatg cacgactacc acgacttcac gctgcacctc    540
gcgctcgcag cagcggatgg gaaggaggtg gtcggcaagg gctggggca gcgccatccg     600
ctggcgggac ccggcgtgcc gggtccgccg aacgagtgga cctttgtgta tgcgccgagg    660
aatgaagagg agatgggcgt ggtcgagcag atcgtagagg cggcgattgg gtacatgtcg    720
aacgtgcctg cgctggaa                                                   738
```

<210> SEQ ID NO 12
<211> LENGTH: 246
<212> TYPE: PRT
<213> ORGANISM: Mycena citricolor

<400> SEQUENCE: 12

```
Met Ala Tyr Gln Leu Thr Trp Ile Gln Thr Leu Val Leu Gly Ala Leu
1               5                   10                  15

Val Ala Met Ala Val Ala Phe Pro Phe Ile Lys Lys Asp Tyr Glu Thr
            20                  25                  30

Phe Leu Lys Gly Gly Pro Ser Tyr Ala Pro Gln Asn Val Arg Gly Tyr
        35                  40                  45

Ile Ile Val Leu Val Leu Ala Leu Phe Arg Gln Glu Gln Leu Gly Leu
    50                  55                  60

Glu Ile Tyr Asp Arg Met Pro Glu Lys Arg Arg Trp Leu Ala Asn Leu
65                  70                  75                  80

Pro Gln Arg Glu Gly Pro Arg Pro Lys Thr Thr Ser His Ile Ile Gln
                85                  90                  95

Arg Gln Leu Ser Gln His Thr Asp Pro Ala Phe Gly Ala Ala Tyr Leu
            100                 105                 110

Lys Asp Thr Val Ile Pro Arg Val Gln Ala Arg His Ala Ala Asn Thr
        115                 120                 125

His Ile Ala Arg Ser Thr Phe Glu Phe His Ala Ala Ile Phe Leu
    130                 135                 140

Asn Ala Asp Val Pro Leu Pro Glu Gly Leu Pro Ala Ser Glu Thr Val
145                 150                 155                 160

Arg Arg Thr Lys Gly Glu Ile Ala His Met His Asp Tyr His Asp Phe
                165                 170                 175

Thr Leu His Leu Ala Leu Ala Ala Ala Asp Gly Lys Glu Val Val Gly
            180                 185                 190

Lys Gly Trp Gly Gln Arg His Pro Leu Ala Gly Pro Gly Val Pro Gly
        195                 200                 205
```

```
Pro Pro Asn Glu Trp Thr Phe Val Tyr Ala Pro Arg Asn Glu Glu Glu
    210                 215                 220
Met Gly Val Val Glu Gln Ile Val Glu Ala Ala Ile Gly Tyr Met Ser
225                 230                 235                 240
Asn Val Pro Ala Leu Glu
                245

<210> SEQ ID NO 13
<211> LENGTH: 786
<212> TYPE: DNA
<213> ORGANISM: Omphalotus olearius

<400> SEQUENCE: 13
atgctcccag ctttcatcta caaaccaagg ctagtgatca cttgtgtatt cgttctggcc      60
tccgcactcg catttccctt catacgcaaa gattaccaga cttccctgga ggtgggaccc     120
tcgtacgccc cgcagaacct ccaaggatac atcatcgtct gtgtactctc tctgttccgg     180
caagaacaga aagacgtagc gatttatgat cgccttcctg agaaaaggag gtggttagga     240
gacctcccgt ttcgcgaggg gccaagaccg agtatcacta gccatatcat ccagcgacag     300
cgcacccaat tggctgacgc cgagttcgct accaaagagc tgataggcaa aatcatccct     360
cgcgtccaag cccgacacac aacacaaca ttcctcagca catctaaatt cgaattccac     420
gcccaggcca tcttcctttt gccctctatc ccaatcaacg accctcaaaa cattccaagc     480
cacgataccg ttcgtcgcac gaaacgcgag atcgcgcata tgcatgatta tcacgactgt     540
acgttgcatc tcgcacttgc tgctcaagat gggaaggagg ttttagagaa aggatggggt     600
cagcgacatc ctcttgctgg acctggtgtt cctggcccgc cgacggagtg gacgtttctt     660
tatgcaccgc gcagcgaaga ggaggttcgg gttgtggaga tgattgttga ggcatcagtt     720
gtgtatatga cgaatgatcc tgcggataaa atcgtagaag ctactgtgca gggtactgaa     780
gaatag                                                                786

<210> SEQ ID NO 14
<211> LENGTH: 261
<212> TYPE: PRT
<213> ORGANISM: Omphalotus olearius

<400> SEQUENCE: 14

Met Leu Pro Ala Phe Ile Tyr Lys Pro Arg Leu Val Ile Thr Cys Val
1               5                   10                  15

Phe Val Leu Ala Ser Ala Leu Ala Phe Pro Phe Ile Arg Lys Asp Tyr
            20                  25                  30

Gln Thr Phe Leu Glu Val Gly Pro Ser Tyr Ala Pro Gln Asn Leu Gln
        35                  40                  45

Gly Tyr Ile Ile Val Cys Val Leu Ser Leu Phe Arg Gln Glu Gln Lys
    50                  55                  60

Asp Val Ala Ile Tyr Asp Arg Leu Pro Glu Lys Arg Arg Trp Leu Gly
65                  70                  75                  80

Asp Leu Pro Phe Arg Glu Gly Pro Arg Pro Ser Ile Thr Ser His Ile
                85                  90                  95

Ile Gln Arg Gln Arg Thr Gln Leu Ala Asp Ala Glu Phe Ala Thr Lys
            100                 105                 110

Glu Leu Ile Gly Lys Ile Ile Pro Arg Val Gln Ala Arg His Thr Asn
        115                 120                 125

Thr Thr Phe Leu Ser Thr Ser Lys Phe Glu Phe His Ala Gln Ala Ile
    130                 135                 140
```

```
Phe Leu Leu Pro Ser Ile Pro Ile Asn Asp Pro Gln Asn Ile Pro Ser
145                 150                 155                 160

His Asp Thr Val Arg Thr Lys Arg Glu Ile Ala His Met His Asp
            165                 170                 175

Tyr His Asp Cys Thr Leu His Leu Ala Leu Ala Ala Gln Asp Gly Lys
            180                 185                 190

Glu Val Leu Glu Lys Gly Trp Gly Gln Arg His Pro Leu Ala Gly Pro
        195                 200                 205

Gly Val Pro Gly Pro Pro Thr Glu Trp Thr Phe Leu Tyr Ala Pro Arg
        210                 215                 220

Ser Glu Glu Glu Val Arg Val Val Glu Met Ile Val Glu Ala Ser Val
225                 230                 235                 240

Val Tyr Met Thr Asn Asp Pro Ala Asp Lys Ile Val Glu Ala Thr Val
                245                 250                 255

Gln Gly Thr Glu Glu
            260

<210> SEQ ID NO 15
<211> LENGTH: 747
<212> TYPE: DNA
<213> ORGANISM: Panellus stipticus

<400> SEQUENCE: 15
atgaacatca acctgaaagc tctgatcgga gtctgtgccg tgctcatcac cgctgcagtg    60 ttcccttcg ttcgtaaaga ctatcacacc tttcttgaag gtggaccatc ctacgcgccg   120
cagaatttgc aaggctatat catcgtgttg gtgctctcac tctttcgagg ggaggagacg   180
ggattggaaa tatacgaccg cttgcccgaa aaacgccgct ggctcgagga gctgcctgtt   240
cgcgaaggcc gcgcccaaa gacaaccagc cacatcattc agagacagtt gaatcagcac    300
gttgacccgg acttcggaat gaactctttg aaaggctccg tcatccggcg ccttcaatcc   360
cgccaccagg acataactca actcgcactc tcgaaattcg aattccacgc cgaggccata   420
tttctgcgcc ccgatgtcgc gatcaacgat cccaaacacg tcccgagcca cgacacggtg   480
cgccgcacaa agcgcgagat agctcacatg cacgactacc atgattacac gtgtcatttg   540
gcgctcgcag cgcaggatgg gaagcaagtg attgcaaaag ggtggggcca gagacatccg   600
ctcgccggac cgggcatgcc ggggccgccg acggagtgga cattttgta tgcgccgagg    660 aatgaggcgg aggttcaagt gttggagacg attatcgaag cgtcaatcgg gtacatgtcg   720
aacgcaccag ccttgggtgg gagcgag                                        747

<210> SEQ ID NO 16
<211> LENGTH: 249
<212> TYPE: PRT
<213> ORGANISM: Panellus stipticus

<400> SEQUENCE: 16

Met Asn Ile Asn Leu Lys Ala Leu Ile Gly Val Cys Ala Val Leu Ile
1               5                   10                  15

Thr Ala Ala Val Phe Pro Phe Val Arg Lys Asp Tyr His Thr Phe Leu
            20                  25                  30

Glu Gly Gly Pro Ser Tyr Ala Pro Gln Asn Leu Gln Gly Tyr Ile Ile
        35                  40                  45

Val Leu Val Leu Ser Leu Phe Arg Gly Glu Glu Thr Gly Leu Glu Ile
    50                  55                  60
```

Tyr Asp Arg Leu Pro Glu Lys Arg Arg Trp Leu Glu Glu Leu Pro Val
 65                  70                  75                  80

Arg Glu Gly Pro Arg Pro Lys Thr Thr Ser His Ile Ile Gln Arg Gln
                 85                  90                  95

Leu Asn Gln His Val Asp Pro Asp Phe Gly Met Asn Ser Leu Lys Gly
            100                 105                 110

Ser Val Ile Arg Arg Leu Gln Ser Arg His Gln Asp Ile Thr Gln Leu
        115                 120                 125

Ala Leu Ser Lys Phe Glu Phe His Ala Glu Ala Ile Phe Leu Arg Pro
130                 135                 140

Asp Val Ala Ile Asn Asp Pro Lys His Val Pro Ser His Asp Thr Val
145                 150                 155                 160

Arg Arg Thr Lys Arg Glu Ile Ala His Met His Asp Tyr His Asp Tyr
                165                 170                 175

Thr Cys His Leu Ala Leu Ala Ala Gln Asp Gly Lys Gln Val Ile Ala
            180                 185                 190

Lys Gly Trp Gly Gln Arg His Pro Leu Ala Gly Pro Gly Met Pro Gly
        195                 200                 205

Pro Pro Thr Glu Trp Thr Phe Leu Tyr Ala Pro Arg Asn Glu Ala Glu
    210                 215                 220

Val Gln Val Leu Glu Thr Ile Ile Glu Ala Ser Ile Gly Tyr Met Ser
225                 230                 235                 240

Asn Ala Pro Ala Leu Gly Gly Ser Glu
                245

<210> SEQ ID NO 17
<211> LENGTH: 747
<212> TYPE: DNA
<213> ORGANISM: Panellus stipticus

<400> SEQUENCE: 17

```
atgaacatca acctgaaagc tctgatcgga gtctgtgccg tgctcatcac cgctgcagtg    60
ttccccttcg ttcgtaaaga ctatcacacc tttcttgaag gtggaccatc ctacgcgccg   120
cagaatttgc aaggctatat catcgtgttg gtgctctcac tctttcgagg ggaggagacg   180
ggattggaaa tatacgaccg cttgcccgaa aaacgccgct ggctcgagga gctgcctgtt   240
cgcgaaggcc cgcgcccaaa gacaaccagc cacatcattc agagacagtt gaatcagcac   300
gttgacccgg acttcggaat gaactctttg aaaggctccg tcatccggcg ccttcaatcc   360
cgccaccagg acataactca actcgcactc tcgaaattcg aattccacgc cgaggccata   420
tttctgcgcc ccgatatcgc gatcaacgat cccaaacacg tcccgagcca cgacacggtg   480
cgccgcacaa agcgcgagat agctcacatg cacgactacc atgattacac gtgtcatttg   540
gcgctcgcag cgcaggatgg gaagcaagtg attgcaaaag ggtggggcca gagacatccg   600
ctcgccggac cgggcatgcc ggggccgccg acggagtgga catttttgta tgcgccgagg   660
aatgaggcgg aggttcaagt gttggagacg attatcgaag cgtcaatcgg gtacatgtcg   720
aacgcaccag ccttgggtgg gagcgag                                       747
```

<210> SEQ ID NO 18
<211> LENGTH: 249
<212> TYPE: PRT
<213> ORGANISM: Panellus stipticus

<400> SEQUENCE: 18

Met Asn Ile Asn Leu Lys Ala Leu Ile Gly Val Cys Ala Val Leu Ile

```
            1               5                  10                 15
        Thr Ala Val Phe Pro Phe Val Arg Lys Asp Tyr His Thr Phe Leu
                        20                 25                 30
        Glu Gly Gly Pro Ser Tyr Ala Pro Gln Asn Leu Gln Gly Tyr Ile Ile
                        35                  40                  45
        Val Leu Val Leu Ser Leu Phe Arg Gly Glu Glu Thr Gly Leu Glu Ile
                    50                  55                  60
        Tyr Asp Arg Leu Pro Glu Lys Arg Arg Trp Leu Glu Glu Leu Pro Val
        65                  70                  75                  80
        Arg Glu Gly Pro Arg Pro Lys Thr Thr Ser His Ile Ile Gln Arg Gln
                            85                  90                  95
        Leu Asn Gln His Val Asp Pro Asp Phe Gly Met Asn Ser Leu Lys Gly
                        100                 105                 110
        Ser Val Ile Arg Arg Leu Gln Ser Arg His Gln Asp Ile Thr Gln Leu
                        115                 120                 125
        Ala Leu Ser Lys Phe Glu Phe His Ala Glu Ala Ile Phe Leu Arg Pro
                    130                 135                 140
        Asp Ile Ala Ile Asn Asp Pro Lys His Val Pro Ser His Asp Thr Val
        145                 150                 155                 160
        Arg Arg Thr Lys Arg Glu Ile Ala His Met His Asp Tyr His Asp Tyr
                            165                 170                 175
        Thr Cys His Leu Ala Leu Ala Ala Gln Asp Gly Lys Gln Val Ile Ala
                        180                 185                 190
        Lys Gly Trp Gly Gln Arg His Pro Leu Ala Gly Pro Gly Met Pro Gly
                        195                 200                 205
        Pro Pro Thr Glu Trp Thr Phe Leu Tyr Ala Pro Arg Asn Glu Ala Glu
                    210                 215                 220
        Val Gln Val Leu Glu Thr Ile Ile Glu Ala Ser Ile Gly Tyr Met Ser
        225                 230                 235                 240
        Asn Ala Pro Ala Leu Gly Gly Ser Glu
                        245

<210> SEQ ID NO 19
<211> LENGTH: 690
<212> TYPE: DNA
<213> ORGANISM: artificial sequence
<220> FEATURE:
<223> OTHER INFORMATION: Nucleic acid coding the functional fragment of
      luciferase from Neonothopanus nambi

<400> SEQUENCE: 19
atcatccgca gagactacca gactttccta gaagtgggac cctcgtacgc tccgcagaac      60
tttagaggat acatcatcgt ctgtgtcctc tcgctattcc gccaagagca gaaagggctc     120
gccatctatg atcgtcttcc cgagaaacgc aggtggttgg ccgaccttcc ctttcgtgaa     180
ggaaccagac ccagcattac cagccatatc attcagcgac agcgcactca actggtcgat     240
caggagtttg ccaccaggga gctcatagac aaggtcatcc ctcgcgtgca agcacgacac     300
accgacaaaa cgttcctcag cacatcaaag ttcgagtttc atgcgaaggc catatttctc     360
ttgccttcta tcccaatcaa cgaccctctg aatatcccta gccacgacac tgtccgccga     420
acgaagcgcg agattgcaca tatgcatgat tatcatgatt gcacacttca tcttgctctc     480
gctgcgcagg atggaaagga ggtgctgaag aaaggttggg gacaacgaca tcctttggct     540
ggtcctggag ttcctggtcc accaacggaa tggacttttc tttatgcgcc tcgcaacgaa     600
gaagaggctc gagtagtgga gatgatcgtt gaggcttcca tagggtatat gacgaacgat     660
```

```
cctgcaggaa agattgtaga aaacgccaag                                       690
```

<210> SEQ ID NO 20
<211> LENGTH: 230
<212> TYPE: PRT
<213> ORGANISM: artificial sequence
<220> FEATURE:
<223> OTHER INFORMATION: Amino acid sequence of the functional fragment
of luciferase from Neonothopanus nambi

<400> SEQUENCE: 20

```
Ile Ile Arg Arg Asp Tyr Gln Thr Phe Leu Glu Val Gly Pro Ser Tyr
  1               5                  10                  15

Ala Pro Gln Asn Phe Arg Gly Tyr Ile Ile Val Cys Val Leu Ser Leu
                 20                  25                  30

Phe Arg Gln Glu Gln Lys Gly Leu Ala Ile Tyr Asp Arg Leu Pro Glu
             35                  40                  45

Lys Arg Arg Trp Leu Ala Asp Leu Pro Phe Arg Glu Gly Thr Arg Pro
         50                  55                  60

Ser Ile Thr Ser His Ile Ile Gln Arg Gln Thr Gln Leu Val Asp
 65                  70                  75                  80

Gln Glu Phe Ala Thr Arg Glu Leu Ile Asp Lys Val Ile Pro Arg Val
                 85                  90                  95

Gln Ala Arg His Thr Asp Lys Thr Phe Leu Ser Thr Ser Lys Phe Glu
            100                 105                 110

Phe His Ala Lys Ala Ile Phe Leu Leu Pro Ser Ile Pro Ile Asn Asp
        115                 120                 125

Pro Leu Asn Ile Pro Ser His Asp Thr Val Arg Arg Thr Lys Arg Glu
    130                 135                 140

Ile Ala His Met His Asp Tyr His Asp Cys Thr Leu His Leu Ala Leu
145                 150                 155                 160

Ala Ala Gln Asp Gly Lys Glu Val Leu Lys Lys Gly Trp Gly Gln Arg
                165                 170                 175

His Pro Leu Ala Gly Pro Gly Val Pro Gly Pro Pro Thr Glu Trp Thr
            180                 185                 190

Phe Leu Tyr Ala Pro Arg Asn Glu Glu Ala Arg Val Val Glu Met
        195                 200                 205

Ile Val Glu Ala Ser Ile Gly Tyr Met Thr Asn Asp Pro Ala Gly Lys
    210                 215                 220

Ile Val Glu Asn Ala Lys
225                 230
```

<210> SEQ ID NO 21
<211> LENGTH: 681
<212> TYPE: DNA
<213> ORGANISM: artificial
<220> FEATURE:
<223> OTHER INFORMATION: Nucleic acid coding the functional fragment of
luciferase from Armillaria gallica

<400> SEQUENCE: 21

```
tacattcgta gggactacca gacatttta tctggcggtc cctcttacgc tccccagaat      60
atcagaggat atttcatcgt ctgcgttctg gccttgttcc gtcaggagca aaagggcctt    120
gcgatatatg atcgccttcc cgagaagcgc aggtggctgc ctgacttgcc tcctcgcaat    180
ggcccgcggc cgatcacgac cagccatata atccaaagac agcgcaacca ggcgccggac    240
cccaagttcg ccctcgagga actcaaggcc acggttattc cacgggtgca ggctcgccat    300
```

```
actgacctca cccatctcag cctatccaaa ttcgagttcc atgctgaagc aattttcctg    360
ctcccctctg tacccatcga tgatccaaaa aatgttccaa gtcacgacac ggtgcgcagg    420
acgaaaaggg agatcgcgca tatgcacgac taccatgact tcacgctgca tcttgcactg    480
gccgcccaag acgggaagga agtcgtgtcg aagggatggg ggcagcgaca ccccctagca    540
ggccctggcg ttcctggtcc acctacggag tggacattta tttatgcgcc acgtaacgaa    600
gaggaactgg cagtggtgga aatgattatc gaggcatcaa taggctatat gaccaatgac    660
cctgctggag tagttatcgc a                                              681
```

<210> SEQ ID NO 22
<211> LENGTH: 227
<212> TYPE: PRT
<213> ORGANISM: artificial
<220> FEATURE:
<223> OTHER INFORMATION: Amino acid sequence of the functional fragment
    of luciferase from Armillaria gallica

<400> SEQUENCE: 22

```
Tyr Ile Arg Arg Asp Tyr Gln Thr Phe Leu Ser Gly Gly Pro Ser Tyr
1               5                   10                  15

Ala Pro Gln Asn Ile Arg Gly Tyr Phe Ile Val Cys Val Leu Ala Leu
            20                  25                  30

Phe Arg Gln Glu Gln Lys Gly Leu Ala Ile Tyr Asp Arg Leu Pro Glu
        35                  40                  45

Lys Arg Arg Trp Leu Pro Asp Leu Pro Pro Arg Asn Gly Pro Arg Pro
    50                  55                  60

Ile Thr Thr Ser His Ile Ile Gln Arg Gln Asn Gln Ala Pro Asp
65                  70                  75                  80

Pro Lys Phe Ala Leu Glu Glu Leu Lys Ala Thr Val Ile Pro Arg Val
                85                  90                  95

Gln Ala Arg His Thr Asp Leu Thr His Leu Ser Leu Ser Lys Phe Glu
            100                 105                 110

Phe His Ala Glu Ala Ile Phe Leu Leu Pro Ser Val Pro Ile Asp Asp
        115                 120                 125

Pro Lys Asn Val Pro Ser His Asp Thr Val Arg Arg Thr Lys Arg Glu
    130                 135                 140

Ile Ala His Met His Asp Tyr His Asp Phe Thr Leu His Leu Ala Leu
145                 150                 155                 160

Ala Ala Gln Asp Gly Lys Glu Val Val Ser Lys Gly Trp Gly Gln Arg
                165                 170                 175

His Pro Leu Ala Gly Pro Gly Val Pro Gly Pro Thr Glu Trp Thr
            180                 185                 190

Phe Ile Tyr Ala Pro Arg Asn Glu Glu Glu Leu Ala Val Val Glu Met
        195                 200                 205

Ile Ile Glu Ala Ser Ile Gly Tyr Met Thr Asn Asp Pro Ala Gly Val
    210                 215                 220

Val Ile Ala
225
```

<210> SEQ ID NO 23
<211> LENGTH: 681
<212> TYPE: DNA
<213> ORGANISM: artificial
<220> FEATURE:
<223> OTHER INFORMATION: Nucleic acid coding the functional fragment of
    luciferase from Armillaria mellea

<400> SEQUENCE: 23

```
tacattcgta gggactacca gacattttta tctgggggtc cctcctacgc tccccagaac    60
atcagaggat acctcattgt ctgcgtcctg gccttgttcc gtcaggagca aaaaggcctt   120
gcgatatacg accgccttcc cgagaagcgc aggtggctac ctgacttgcc tcctcgcgat   180
ggcccacggc ccatcacgac cagccatata atccaaagac agcgcaacca ggcgccggac   240
ctcaagttcg ccctcgagga actcaaggcc acggtcattc cacgggtgca ggctcgccac   300
actgacctca cccatctcag cctatccaag ttcgagttcc atgctgaagc aatcttcctg   360
ctcccctctg tacccatcga tgatccaaag aatgtgccaa gtcacgacac ggtgcgcagg   420
acgaagaggg aaattgcgca tatgcacgac taccatgact acacgctgca tcttgcgttg   480
gccgcccaag acgggaagga agtcgtatca aagggatggg ggcagcgaca cccgctggca   540
ggccctggcg ttcctggtcc accgacggag tggacgttta tttatgcgcc acgtaacgaa   600
gaggagctgg cagtggtgga aatgattatc gaggcatcga taggctatat gaccaatgac   660
cctgcaggaa aaactatcgc a                                             681
```

<210> SEQ ID NO 24
<211> LENGTH: 227
<212> TYPE: PRT
<213> ORGANISM: artificial
<220> FEATURE:
<223> OTHER INFORMATION: Amino acid sequence of the functional fragment
of luciferase from Armillaria mellea

<400> SEQUENCE: 24

```
Tyr Ile Arg Arg Asp Tyr Gln Thr Phe Leu Ser Gly Gly Pro Ser Tyr
1               5                   10                  15
Ala Pro Gln Asn Ile Arg Gly Tyr Leu Ile Val Cys Val Leu Ala Leu
            20                  25                  30
Phe Arg Gln Glu Gln Lys Gly Leu Ala Ile Tyr Asp Arg Leu Pro Glu
        35                  40                  45
Lys Arg Arg Trp Leu Pro Asp Leu Pro Pro Arg Asp Gly Pro Arg Pro
    50                  55                  60
Ile Thr Thr Ser His Ile Ile Gln Arg Gln Arg Asn Gln Ala Pro Asp
65                  70                  75                  80
Leu Lys Phe Ala Leu Glu Glu Leu Lys Ala Thr Val Ile Pro Arg Val
                85                  90                  95
Gln Ala Arg His Thr Asp Leu Thr His Leu Ser Leu Ser Lys Phe Glu
            100                 105                 110
Phe His Ala Glu Ala Ile Phe Leu Leu Pro Ser Val Pro Ile Asp Asp
        115                 120                 125
Pro Lys Asn Val Pro Ser His Asp Thr Val Arg Thr Lys Arg Glu
    130                 135                 140
Ile Ala His Met His Asp Tyr His Asp Tyr Thr Leu His Leu Ala Leu
145                 150                 155                 160
Ala Ala Gln Asp Gly Lys Glu Val Val Ser Lys Gly Trp Gly Gln Arg
                165                 170                 175
His Pro Leu Ala Gly Pro Gly Val Pro Gly Pro Pro Thr Glu Trp Thr
            180                 185                 190
Phe Ile Tyr Ala Pro Arg Asn Glu Glu Glu Leu Ala Val Val Glu Met
        195                 200                 205
Ile Ile Glu Ala Ser Ile Gly Tyr Met Thr Asn Asp Pro Ala Gly Lys
    210                 215                 220
```

Thr Ile Ala
225

<210> SEQ ID NO 25
<211> LENGTH: 798
<212> TYPE: DNA
<213> ORGANISM: artificial
<220> FEATURE:
<223> OTHER INFORMATION: Nucleic acid coding the functional fragment of
      luciferase from Armillaria ostoyae

<400> SEQUENCE: 25

```
atgtccttca tcgacagcat gaaacttgac ttcgtcggac acctctttgg catcaggaat      60
cgcggcttag ccaccgcttg ttgtgctgtg gcagtcgctt ctgccatcgc cttcccttac     120
attcgtaggg actaccagac attcttatct ggcggtccct cttacgctcc ccagaacatc     180
aaaggatatc tcatcgtctg cgtcctggcc ttgttccgtc aggagcaaaa gggccttgcg     240
atatatgacc gccttcccga gaagcgcagg tggctacctg acttgcctcc tcgcaatggc     300
ccgcggccca tcacgaccag ccatataatc aaagacagc gcaaccaggc gccagactcc      360
aagttcgccc tcgaggaact caaggctacg gtcattccac gggtgcaggc tcgccacact     420
gacctcaccc atctcagcct atccaagttc gagttccatg ctgaagcaat cttcctgctc     480
ccctctgtac ccatcgatga tccaaaaaat gttccaagtc atgacacggt gcgcaggacg     540
aagagggaga tcgcgcatat gcacgactac catgacttta cgttgcatct tgcactggcc     600
gcccaagacg ggaaggaagt cgtggcgaag ggatgggggc agcgacaccc gctggcaggc     660
cctggcgttc ctggtccacc tacggagtgg acgtttattt atgcgccacg taacgaagag     720
gaactggcag tggtggaaat gattatcgag gcatcaatag gctatatgac caatgaccct     780
gctggaacag ttatcgta                                                   798
```

<210> SEQ ID NO 26
<211> LENGTH: 266
<212> TYPE: PRT
<213> ORGANISM: artificial
<220> FEATURE:
<223> OTHER INFORMATION: Amino acid sequence of the functional fragment
      of luciferase from Armillaria ostoyae

<400> SEQUENCE: 26

Met Ser Phe Ile Asp Ser Met Lys Leu Asp Phe Val Gly His Leu Phe
1               5                   10                  15

Gly Ile Arg Asn Arg Gly Leu Ala Thr Ala Cys Cys Ala Val Ala Val
            20                  25                  30

Ala Ser Ala Ile Ala Phe Pro Tyr Ile Arg Arg Asp Tyr Gln Thr Phe
        35                  40                  45

Leu Ser Gly Gly Pro Ser Tyr Ala Pro Gln Asn Ile Lys Gly Tyr Leu
    50                  55                  60

Ile Val Cys Val Leu Ala Leu Phe Arg Gln Glu Gln Lys Gly Leu Ala
65                  70                  75                  80

Ile Tyr Asp Arg Leu Pro Glu Lys Arg Arg Trp Leu Pro Asp Leu Pro
                85                  90                  95

Pro Arg Asn Gly Pro Arg Pro Ile Thr Thr Ser His Ile Ile Gln Arg
            100                 105                 110

Gln Arg Asn Gln Ala Pro Asp Ser Lys Phe Ala Leu Glu Glu Leu Lys
        115                 120                 125

Ala Thr Val Ile Pro Arg Val Gln Ala Arg His Thr Asp Leu Thr His

```
Leu Ser Leu Ser Lys Phe Glu Phe His Ala Glu Ala Ile Phe Leu Leu
            145                 150                 155                 160

Pro Ser Val Pro Ile Asp Asp Pro Lys Asn Val Pro Ser His Asp Thr
                165                 170                 175

Val Arg Arg Thr Lys Arg Glu Ile Ala His Met His Asp Tyr His Asp
            180                 185                 190

Phe Thr Leu His Leu Ala Leu Ala Ala Gln Asp Gly Lys Glu Val Val
        195                 200                 205

Ala Lys Gly Trp Gly Gln Arg His Pro Leu Ala Gly Pro Gly Val Pro
    210                 215                 220

Gly Pro Pro Thr Glu Trp Thr Phe Ile Tyr Ala Pro Arg Asn Glu Glu
225                 230                 235                 240

Glu Leu Ala Val Val Glu Met Ile Ile Glu Ala Ser Ile Gly Tyr Met
                245                 250                 255

Thr Asn Asp Pro Ala Gly Thr Val Ile Val
            260                 265

<210> SEQ ID NO 27
<211> LENGTH: 684
<212> TYPE: DNA
<213> ORGANISM: artificial
<220> FEATURE:
<223> OTHER INFORMATION: Nucleic acid coding the functional fragment of
      luciferase from Mycena chlorophos

<400> SEQUENCE: 27
ttcattcgtc gagactacca gacgttcctt cgtggtgggc cgtcctatgc cccacagaac      60
atccgcggct atatcatcgt cctggttctg tccctcttcc gcggcgagga gaagggtctt     120
gcaatctacg agccccttcc tgagaagcgc acatggctgc cggagcttcc gcggcgcgcg     180
ggagaccggc ccaagacgac gagccacatc atccaacggc agctcgacca gtaccccgac     240
ccggactttg tcctcaaagc cctgaaagcg acggtcatcc cgcgtgtcca agcccggcac     300
acagacaaga ctcacctcgc gctgtccaag ttcgagttcc atgctgaggc catcttcgtg     360 cgccccggaaa tcgccatcga cgacccgaag catatcccca gccacgacac ggtgcgacgg    420
acgaagcgcg agattgcgca catgcacgac tatcacgact gcacgctgca tttggcgcta    480
gcggcgcagg acgcgaagca ggtgctgcag aagggctggg gccagcgcca tccgctggca    540
gggcctggga tgcccgggcc gcccacggag tggacgttct tgtatgcccc gaggaccgag    600
gaggaagtga aggttgtgga gaccattgtc gaggcctcta tcgcgtacat gacgaacgcg    660
gagaagccgg tcgagctggt gcag                                            684

<210> SEQ ID NO 28
<211> LENGTH: 228
<212> TYPE: PRT
<213> ORGANISM: artificial
<220> FEATURE:
<223> OTHER INFORMATION: Amino acid sequence of the functional fragment
      of luciferase from Mycena chlorophos

<400> SEQUENCE: 28

Phe Ile Arg Arg Asp Tyr Gln Thr Phe Leu Arg Gly Gly Pro Ser Tyr
1               5                   10                  15

Ala Pro Gln Asn Ile Arg Gly Tyr Ile Ile Val Leu Val Leu Ser Leu
            20                  25                  30

Phe Arg Gly Glu Glu Lys Gly Leu Ala Ile Tyr Glu Pro Leu Pro Glu
```

```
                    35                  40                  45
Lys Arg Thr Trp Leu Pro Glu Leu Pro Arg Arg Ala Gly Asp Arg Pro
 50                  55                  60

Lys Thr Thr Ser His Ile Ile Gln Arg Gln Leu Asp Gln Tyr Pro Asp
 65                  70                  75                  80

Pro Asp Phe Val Leu Lys Ala Leu Lys Ala Thr Val Ile Pro Arg Val
                 85                  90                  95

Gln Ala Arg His Thr Asp Lys Thr His Leu Ala Leu Ser Lys Phe Glu
             100                 105                 110

Phe His Ala Glu Ala Ile Phe Val Arg Pro Glu Ile Ala Ile Asp Asp
         115                 120                 125

Pro Lys His Ile Pro Ser His Asp Thr Val Arg Arg Thr Lys Arg Glu
     130                 135                 140

Ile Ala His Met His Asp Tyr His Asp Cys Thr Leu His Leu Ala Leu
145                 150                 155                 160

Ala Ala Gln Asp Ala Lys Gln Val Leu Gln Lys Gly Trp Gly Gln Arg
                165                 170                 175

His Pro Leu Ala Gly Pro Gly Met Pro Gly Pro Thr Glu Trp Thr
            180                 185                 190

Phe Leu Tyr Ala Pro Arg Thr Glu Glu Val Lys Val Val Glu Thr
        195                 200                 205

Ile Val Glu Ala Ser Ile Ala Tyr Met Thr Asn Ala Glu Lys Pro Val
    210                 215                 220

Glu Leu Val Gln
225
```

<210> SEQ ID NO 29
<211> LENGTH: 666
<212> TYPE: DNA
<213> ORGANISM: artificial
<220> FEATURE:
<223> OTHER INFORMATION: Nucleic acid coding the functional fragment of
      luciferase from Mycena citricolor

<400> SEQUENCE: 29

```
ttcatcaaga aagactacga gacgttcctg aagggcggcc cctcctatgc gccccaaaac       60
gttcgcggat acatcatcgt gctcgtgctc gcgctcttcc gccaagagca gctcgggctg      120
gagatctacg accgcatgcc cgagaaacgt cgctggctcg cgaatctccc tcagcgcgag      180
ggcccccgcc ccaagaccac aagtcacatc atccagcggc agctcagcca gcacacggac      240
cccgcattcg gcgccgcgta cctcaaagac accgtcattc cgcgcgtcca ggcgcggcac      300
gcagccaaca cgcacatcgc cgctcgacg ttcgagttcc acgccgccgc gatcttcctg       360
aacgcggacg tgccgctgcc cgagggcctg cccgcaagcg agacggtgcg gcggaccaag      420
ggcgagatcg cgcacatgca cgactaccac gacttcacgc tgcacctcgc gctcgcagca      480
gcggatggga aggaggtggt cggcaagggc tggggcagc gccatccgct ggcgggaccc       540
ggcgtgccgg gtccgccgaa cgagtggacc tttgtgtatg cgccgaggaa tgaagaggag      600
atgggcgtgg tcgagcagat cgtagaggcg gcgattgggt acatgtcgaa cgtgcctgcg      660
ctggaa                                                                 666
```

<210> SEQ ID NO 30
<211> LENGTH: 222
<212> TYPE: PRT
<213> ORGANISM: artificial
<220> FEATURE:

<223> OTHER INFORMATION: Amino acid sequence of the functional fragment
      of luciferase from Mycena citricolor

<400> SEQUENCE: 30

Phe Ile Lys Lys Asp Tyr Glu Thr Phe Leu Lys Gly Gly Pro Ser Tyr
1               5                   10                  15

Ala Pro Gln Asn Val Arg Gly Tyr Ile Val Leu Val Leu Ala Leu
            20                  25                  30

Phe Arg Gln Glu Gln Leu Gly Leu Glu Ile Tyr Asp Arg Met Pro Glu
            35                  40                  45

Lys Arg Arg Trp Leu Ala Asn Leu Pro Gln Arg Glu Gly Pro Arg Pro
        50                  55                  60

Lys Thr Thr Ser His Ile Ile Gln Arg Gln Leu Ser Gln His Thr Asp
65                  70                  75                  80

Pro Ala Phe Gly Ala Ala Tyr Leu Lys Asp Thr Val Ile Pro Arg Val
                85                  90                  95

Gln Ala Arg His Ala Ala Asn Thr His Ile Ala Arg Ser Thr Phe Glu
            100                 105                 110

Phe His Ala Ala Ala Ile Phe Leu Asn Ala Asp Val Pro Leu Pro Glu
        115                 120                 125

Gly Leu Pro Ala Ser Glu Thr Val Arg Arg Thr Lys Gly Glu Ile Ala
    130                 135                 140

His Met His Asp Tyr His Asp Phe Thr Leu His Leu Ala Leu Ala Ala
145                 150                 155                 160

Ala Asp Gly Lys Glu Val Val Gly Lys Gly Trp Gln Arg His Pro
                165                 170                 175

Leu Ala Gly Pro Gly Val Pro Gly Pro Pro Asn Glu Trp Thr Phe Val
            180                 185                 190

Tyr Ala Pro Arg Asn Glu Glu Met Gly Val Val Glu Gln Ile Val
            195                 200                 205

Glu Ala Ala Ile Gly Tyr Met Ser Asn Val Pro Ala Leu Glu
    210                 215                 220

<210> SEQ ID NO 31
<211> LENGTH: 705
<212> TYPE: DNA
<213> ORGANISM: artificial
<220> FEATURE:
<223> OTHER INFORMATION: Nucleic acid coding the functional fragment of
      luciferase from Omphalotus olearius

<400> SEQUENCE: 31
ttcatacgca aagattacca gactttcctg gaggtgggac cctcgtacgc cccgcagaac     60
ctccaaggat acatcatcgt ctgtgtactc tctctgttcc ggcaagaaca gaaagacgta    120
gcgatttatg atcgccttcc tgagaaaagg aggtggttag gagacctccc gtttcgcgag    180
gggccaagac cgagtatcac tagccatatc atccagcgac agcgcaccca attggctgac    240
gccgagttcg ctaccaaaga gctgataggc aaaatcatcc ctcgcgtcca gcccgacac     300 accaacacaa cattcctcag cacatctaaa ttcgaattcc acgcccaggc catcttcctt    360
ttgccctcta tcccaatcaa cgaccctcaa acattccaa gccacgatac cgttcgtcgc     420
acgaaacgcg agatcgcgca tatgcatgat tatcacgact gtacgttgca tctcgcactt    480
gctgctcaag atgggaagga ggttttagag aaaggatggg gtcagcgaca tcctcttgct    540
ggacctggtg ttcctggccc gccgacggag tggacgtttc tttatgcacc gcgcagcgaa    600
gaggaggttc gggttgtgga gatgattgtt gaggcatcag ttgtgtatat gacgaatgat    660
cctgcggata aaatcgtaga agctactgtg cagggtactg aagaa           705

<210> SEQ ID NO 32
<211> LENGTH: 235
<212> TYPE: PRT
<213> ORGANISM: artificial
<220> FEATURE:
<223> OTHER INFORMATION: Amino acid sequence of the functional fragment
      of luciferase from Omphalotus olearius

<400> SEQUENCE: 32

Phe Ile Arg Lys Asp Tyr Gln Thr Phe Leu Glu Val Gly Pro Ser Tyr
1               5                   10                  15

Ala Pro Gln Asn Leu Gln Gly Tyr Ile Ile Val Cys Val Leu Ser Leu
            20                  25                  30

Phe Arg Gln Glu Gln Lys Asp Val Ala Ile Tyr Asp Arg Leu Pro Glu
        35                  40                  45

Lys Arg Arg Trp Leu Gly Asp Leu Pro Phe Arg Glu Gly Pro Arg Pro
    50                  55                  60

Ser Ile Thr Ser His Ile Ile Gln Arg Gln Arg Thr Gln Leu Ala Asp
65                  70                  75                  80

Ala Glu Phe Ala Thr Lys Glu Leu Ile Gly Lys Ile Ile Pro Arg Val
                85                  90                  95

Gln Ala Arg His Thr Asn Thr Thr Phe Leu Ser Thr Ser Lys Phe Glu
            100                 105                 110

Phe His Ala Gln Ala Ile Phe Leu Leu Pro Ser Ile Pro Ile Asn Asp
        115                 120                 125

Pro Gln Asn Ile Pro Ser His Asp Thr Val Arg Arg Thr Lys Arg Glu
    130                 135                 140

Ile Ala His Met His Asp Tyr His Asp Cys Thr Leu His Leu Ala Leu
145                 150                 155                 160

Ala Ala Gln Asp Gly Lys Glu Val Leu Glu Lys Gly Trp Gly Gln Arg
                165                 170                 175

His Pro Leu Ala Gly Pro Gly Val Pro Gly Pro Pro Thr Glu Trp Thr
            180                 185                 190

Phe Leu Tyr Ala Pro Arg Ser Glu Glu Val Arg Val Val Glu Met
        195                 200                 205

Ile Val Glu Ala Ser Val Val Tyr Met Thr Asn Asp Pro Ala Asp Lys
    210                 215                 220

Ile Val Glu Ala Thr Val Gln Gly Thr Glu Glu
225                 230                 235

<210> SEQ ID NO 33
<211> LENGTH: 681
<212> TYPE: DNA
<213> ORGANISM: artificial
<220> FEATURE:
<223> OTHER INFORMATION: Nucleic acid coding the functional fragment of
      luciferase from Panellus stipticus

<400> SEQUENCE: 33
ttcgttcgta aagactatca cacctttctt gaaggtggac catcctacgc gccgcagaat           60
ttgcaaggct atatcatcgt gttggtgctc tcactctttc gaggggagga gacgggattg          120
gaaatatacg accgcttgcc cgaaaaacgc cgctggctcg aggagctgcc tgttcgcgaa          180
ggcccgcgcc caaagacaac cagccacatc attcagagac agttgaatca gcacgttgac          240
ccggacttcg gaatgaactc tttgaaaggc tccgtcatcc ggcgccttca atcccgccac          300

-continued

```
caggacataa ctcaactcgc actctcgaaa ttcgaattcc acgccgaggc catatttctg    360
cgccccgatg tcgcgatcaa cgatcccaaa cacgtcccga gccacgacac ggtgcgccgc    420
acaaagcgcg agatagctca catgcacgac taccatgatt acacgtgtca tttggcgctc    480
gcagcgcagg atgggaagca agtgattgca aaagggtggg gccagagaca tccgctcgcc    540
ggaccgggca tgccggggcc gccgacggag tggacatttt tgtatgcgcc gaggaatgag    600
gcggaggttc aagtgttgga gacgattatc gaagcgtcaa tcgggtacat gtcgaacgca    660
ccagccttgg gtgggagcga g                                             681
```

<210> SEQ ID NO 34
<211> LENGTH: 227
<212> TYPE: PRT
<213> ORGANISM: artificial
<220> FEATURE:
<223> OTHER INFORMATION: Amino acid sequence of the functional fragment
of luciferase from Panellus stipticus

<400> SEQUENCE: 34

```
Phe Val Arg Lys Asp Tyr His Thr Phe Leu Glu Gly Gly Pro Ser Tyr
1               5                   10                  15

Ala Pro Gln Asn Leu Gln Gly Tyr Ile Ile Val Leu Val Leu Ser Leu
            20                  25                  30

Phe Arg Gly Glu Glu Thr Gly Leu Glu Ile Tyr Asp Arg Leu Pro Glu
        35                  40                  45

Lys Arg Arg Trp Leu Glu Glu Leu Pro Val Arg Glu Gly Pro Arg Pro
    50                  55                  60

Lys Thr Thr Ser His Ile Ile Gln Arg Gln Leu Asn Gln His Val Asp
65                  70                  75                  80

Pro Asp Phe Gly Met Asn Ser Leu Lys Gly Ser Val Ile Arg Arg Leu
                85                  90                  95

Gln Ser Arg His Gln Asp Ile Thr Gln Leu Ala Leu Ser Lys Phe Glu
            100                 105                 110

Phe His Ala Glu Ala Ile Phe Leu Arg Pro Asp Val Ala Ile Asn Asp
        115                 120                 125

Pro Lys His Val Pro Ser His Asp Thr Val Arg Arg Thr Lys Arg Glu
    130                 135                 140

Ile Ala His Met His Asp Tyr His Asp Tyr Thr Cys His Leu Ala Leu
145                 150                 155                 160

Ala Ala Gln Asp Gly Lys Gln Val Ile Ala Lys Gly Trp Gly Gln Arg
                165                 170                 175

His Pro Leu Ala Gly Pro Gly Met Pro Gly Pro Pro Thr Glu Trp Thr
            180                 185                 190

Phe Leu Tyr Ala Pro Arg Asn Glu Ala Glu Val Gln Val Leu Glu Thr
        195                 200                 205

Ile Ile Glu Ala Ser Ile Gly Tyr Met Ser Asn Ala Pro Ala Leu Gly
    210                 215                 220

Gly Ser Glu
225
```

<210> SEQ ID NO 35
<211> LENGTH: 211
<212> TYPE: PRT
<213> ORGANISM: artificial
<220> FEATURE:
<223> OTHER INFORMATION: Consensus sequence
<220> FEATURE:

<221> NAME/KEY: MISC_FEATURE
<222> LOCATION: (3)..(214)
<223> OTHER INFORMATION: ? ? any amino acid

<400> SEQUENCE: 35

Asp Tyr Xaa Thr Phe Leu Xaa Xaa Gly Pro Ser Tyr Ala Pro Gln Asn
1               5                   10                  15

Xaa Xaa Gly Tyr Xaa Ile Val Xaa Val Leu Xaa Leu Phe Arg Xaa Glu
            20                  25                  30

Xaa Xaa Xaa Xaa Ile Tyr Xaa Xaa Xaa Pro Glu Lys Arg Xaa Trp Leu
        35                  40                  45

Xaa Xaa Leu Pro Xaa Arg Xaa Gly Xaa Arg Pro Xaa Xaa Thr Ser His
    50                  55                  60

Ile Ile Gln Arg Gln Xaa Xaa Gln Xaa Xaa Asp Xaa Xaa Phe Xaa Xaa
65                  70                  75                  80

Xaa Xaa Leu Xaa Xaa Xaa Ile Xaa Arg Xaa Gln Xaa Arg His Xaa
            85                  90                  95

Xaa Xaa Thr Xaa Xaa Xaa Ser Xaa Phe Glu Phe His Ala Xaa Ala Ile
            100                 105                 110

Phe Xaa Xaa Xaa Xaa Xaa Xaa Xaa Pro Xaa Xaa Xaa Pro Xaa Xaa
    115                 120                 125

Xaa Thr Val Arg Arg Thr Lys Xaa Glu Ile Ala His Met His Asp Tyr
    130                 135                 140

His Asp Xaa Thr Xaa His Leu Ala Leu Ala Ala Xaa Asp Xaa Lys Val
145                 150                 155                 160

Xaa Xaa Lys Gly Trp Gly Gln Arg His Pro Leu Ala Gly Pro Gly Xaa
            165                 170                 175

Pro Gly Pro Pro Xaa Glu Trp Thr Phe Xaa Tyr Ala Pro Arg Xaa Glu
            180                 185                 190

Xaa Glu Xaa Xaa Val Xaa Glu Xaa Ile Xaa Glu Ala Xaa Xaa Xaa Tyr
        195                 200                 205

Met Xaa Asn
    210

<210> SEQ ID NO 36
<211> LENGTH: 38
<212> TYPE: DNA
<213> ORGANISM: artificial
<220> FEATURE:
<223> OTHER INFORMATION: Primer 1711
<220> FEATURE:
<221> NAME/KEY: misc_feature
<222> LOCATION: (6)..(36)
<223> OTHER INFORMATION: R - A or G, Y - C or T, S - G or C, W - A or T,
      H - A or T, N ? any base

<400> SEQUENCE: 36
atcgcnttyc cntwcathcc narrgaytac saracntt                            38

<210> SEQ ID NO 37
<211> LENGTH: 35
<212> TYPE: DNA
<213> ORGANISM: artificial
<220> FEATURE:
<223> OTHER INFORMATION: Primer 1712
<220> FEATURE:
<221> NAME/KEY: misc_feature
<222> LOCATION: (6)..(3)
<223> OTHER INFORMATION: R - A or G, Y - C or T, S - G or C, W - A or T,
      H - A or T, N ? any base
<220> FEATURE:
<221> NAME/KEY: misc_feature

```
<222> LOCATION: (6)..(6)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u

<400> SEQUENCE: 37
atcgcnttyc cntwcathcc narrgaytac sarac                              35

<210> SEQ ID NO 38
<211> LENGTH: 32
<212> TYPE: DNA
<213> ORGANISM: artificial
<220> FEATURE:
<223> OTHER INFORMATION: Primer 1713
<220> FEATURE:
<221> NAME/KEY: misc_feature
<222> LOCATION: (6)..(31)
<223> OTHER INFORMATION: R - A or G, Y - C or T, S - G or C, W - A or T,
      H - A or T, N ? any base

<400> SEQUENCE: 38
atcgcnttyc cntwcathcc narrgaytac sa                                 32

<210> SEQ ID NO 39
<211> LENGTH: 29
<212> TYPE: DNA
<213> ORGANISM: artificial
<220> FEATURE:
<223> OTHER INFORMATION: Primer 1714
<220> FEATURE:
<221> NAME/KEY: misc_feature
<222> LOCATION: (6)..(27)
<223> OTHER INFORMATION: R - A or G, Y - C or T, S - G or C, W - A or T,
      H - A or T, N ? any base

<400> SEQUENCE: 39
atcgcnttyc cntwcathcc narrgayta                                     29

<210> SEQ ID NO 40
<211> LENGTH: 42
<212> TYPE: DNA
<213> ORGANISM: artificial
<220> FEATURE:
<223> OTHER INFORMATION: Primer 1715
<220> FEATURE:
<221> NAME/KEY: misc_feature
<222> LOCATION: (1)..(40)
<223> OTHER INFORMATION: R - A or G, Y - C or T, S - G or C, W - A or T,
      H - A or T, N ? any base

<400> SEQUENCE: 40
ngcagggncn ttsgtcatat asccnatnga ngcytcnayn at                      42

<210> SEQ ID NO 41
<211> LENGTH: 36
<212> TYPE: DNA
<213> ORGANISM: artificial
<220> FEATURE:
<223> OTHER INFORMATION: Primer 1716
<220> FEATURE:
<221> NAME/KEY: misc_feature
<222> LOCATION: (1)..(34)
<223> OTHER INFORMATION: R - A or G, Y - C or T, S - G or C, W - A or T,
      H - A or T, N ? any base
```

```
<400> SEQUENCE: 41
ngcagggncn ttsgtcatat asccnatnga ngcytc                             36

<210> SEQ ID NO 42
<211> LENGTH: 32
<212> TYPE: DNA
<213> ORGANISM: artificial
<220> FEATURE:
<223> OTHER INFORMATION: Primer 1717
<220> FEATURE:
<221> NAME/KEY: misc_feature
<222> LOCATION: (7)..(30)
<223> OTHER INFORMATION: R - A or G, Y - C or T, S - G or C, W - A or T,
      H - A or T, N ? any base

<400> SEQUENCE: 42
gcagggncnt tsgtcatata sccnatngan gc                                 32

<210> SEQ ID NO 43
<211> LENGTH: 30
<212> TYPE: DNA
<213> ORGANISM: artificial
<220> FEATURE:
<223> OTHER INFORMATION: Primer 1718
<220> FEATURE:
<221> NAME/KEY: misc_feature
<222> LOCATION: (1)..(28)
<223> OTHER INFORMATION: R - A or G, Y - C or T, S - G or C, W - A or T,
      H - A or T, N ? any base

<400> SEQUENCE: 43
ngcagggncn ttsgtcatat asccnatnga                                    30

<210> SEQ ID NO 44
<211> LENGTH: 801
<212> TYPE: DNA
<213> ORGANISM: artificial
<220> FEATURE:
<223> OTHER INFORMATION: Humanized nucleic acid coding luciferase from
      Neonothopanus nambi

<400> SEQUENCE: 44
atgcgcatta acatctccct ttcatctctt ttcgagcgat tgagcaaact gagttccagg    60
agtattgcaa tcacttgtgg ggttgtcctc gcgagcgcca tcgcattccc catcatccgg   120
agagattatc agacgtttct tgaggtgggc cctagctatg caccacagaa cttccgagga   180
tatatcatcg tgtgtgtact gtcactgttt aggcaagaac aaaagggatt ggctatctat   240
gataggttgc ctgagaaacg gcggtggctc gctgatctcc catttagaga ggggacacga   300
ccgagcatca cttcacacat catacaaaga cagcgaacgc agctcgttga ccaagagttc   360
gcaactaggg aactgattga taaggtgata cccagagtac aggcgcgaca caccgataaa   420
acttttcttt ccacctctaa attcgagttc catgccaaag ctattttctt gttgccttcc   480
ataccgatta tgatcctct gaatattcca tcccacgaca cagttcgacg gacgaaacgc   540
gaaattgcgc acatgcacga ctatcacgat tgcactttgc acctggcact ggctgctcaa   600
gacggaaaag aagttctgaa aaagggttgg gggcaaagac atccgctggc gggacccggt   660
gtacctgggc cgcctacgga atggacattt ttgtacgcac cgaggaacga agaggaggcc   720
agggtcgttg agatgattgt tgaggctagt attgggtaca tgacgaatga tccggctggt   780
aaaattgttg aaaatgcaaa g                                             801

<210> SEQ ID NO 45
```

<211> LENGTH: 798
<212> TYPE: DNA
<213> ORGANISM: artificial
<220> FEATURE:
<223> OTHER INFORMATION: Humanized nucleic acid coding luciferase from
      Armillaria gallica

<400> SEQUENCE: 45

| | |
|---|---:|
| atgagcttta tagactcaat gaaacttgat cttgtaggac acctcttcgg catacgcaac | 60 |
| agaggactcg cagcagcctg ttgcgccctt gcagtagctt ccacgatagc tttcccttat | 120 |
| atccgccggg attaccaaac gttccttagc ggtggccctt cttacgcgcc acagaacata | 180 |
| cgaggctatt ttatcgtgtg tgtgctcgct ctgtttcgcc aagaacagaa agggctggcg | 240 |
| atttatgacc gacttcctga aaacgaagg tggcttcctg accttcctcc ccggaatggc | 300 |
| cctcgcccga ttcgacctc tcatattata caaagacaga ggaaccaagc gccagatccg | 360 |
| aaatttgccc tggaggagct caaggccact gtgattccac gagtccaagc ccgccatacg | 420 |
| gatcttacac atctcagtct tagcaaattt gagtttcatg ccgaggcaat ttttcttttg | 480 |
| ccgtccgttc cgatagacga ccccaaaaat gtaccctcac acgatacggt caggcgcaca | 540 |
| aagagggaga tcgcccatat gcatgactat cacgacttta ccctgcatct cgctctggcg | 600 |
| gcacaagacg gcaaggaggt agtcagcaaa ggctggggcc aaaggcatcc gctcgcgggc | 660 |
| ccaggggttc cggggccacc tacagagtgg actttcatct atgcgccgcg aaacgaggaa | 720 |
| gaactcgcag tagttgagat gatcatagag gcatcaattg gctacatgac gaacgatcct | 780 |
| gccggagtcg ttatagcc | 798 |

<210> SEQ ID NO 46
<211> LENGTH: 798
<212> TYPE: DNA
<213> ORGANISM: artificial
<220> FEATURE:
<223> OTHER INFORMATION: Humanized nucleic acid coding luciferase from
      Armillaria mellea

<400> SEQUENCE: 46

| | |
|---|---:|
| atgagttttt ttgactctgt caaacttgat ctggtgggac ggctcttcgg catccgaaac | 60 |
| aggggacttg cggttacttg ctgcgcggta gcggtcgcct ctattatcgc cttcccatac | 120 |
| attcgccgcg actatcagac cttcctgtca ggcggaccttt cttatgcacc gcagaatata | 180 |
| aggggctatc ttattgtttg tgtactggct ctctttcggc aagaacaaaa aggtctggct | 240 |
| atctacgata gacttcctga aaacgacgc tggctgccag atcttccccc cgcgacggc | 300 |
| ccaaggccca taacaacaag tcatattata cagagacaac ggaaccaggc cccagacctc | 360 |
| aagtttgccc tcgaggagct gaaagcgact gttatacccta gagtacaggc gagacataca | 420 |
| gacttgaccc atttgagcct gagcaagttt gaattccatg ccgaagcaat ctttcttctg | 480 |
| ccttccgtac ccattgacga tccaaaaaac gtcccctcac atgatactgt aagacgcacg | 540 |
| aagcgagaga tcgcacacat gcacgactac catgactaca ctctgcacct tgccttggca | 600 |
| gctcaggatg gcaaggaagt tgtatccaag gggtggggcc aaagacaccc cttggctggc | 660 |
| ccgggagtgc ctggaccccc gaccgaatgg acgttttattt acgcaccaag gaacgaggaa | 720 |
| gaattggccg tcgttgaaat gattattgaa gcgtccatag gatatatgac caacgatccg | 780 |
| gccggaaaga caatcgcg | 798 |

<210> SEQ ID NO 47
<211> LENGTH: 798

```
<212> TYPE: DNA
<213> ORGANISM: artificial
<220> FEATURE:
<223> OTHER INFORMATION: Humanized nucleic acid coding luciferase from
      Armillaria ostoyae

<400> SEQUENCE: 47
atgtctttta ttgacagtat gaagcttgat ttcgtaggtc acttgtttgg tatacgaaac     60
cgaggtctcg ctactgcgtg ctgcgcggtg cagtagcga gtgctatagc attcccgtat    120
atccgccgag attaccagac atttcttagc ggtggaccta gctatgcacc ccagaatatt    180
aaagggtatt tgatcgtttg tgtgcttgca ctgtttcgcc aggagcagaa gggtcttgct    240
atttacgacc gactgcctga gaaaaggcga tggttgcctg accttccacc cagaaacggt    300
cccaggccca tcacgacctc acacataatc aacggcaga ggaaccaggc tccagattca    360
aagtttgcgc ttgaggaact caaggctact gtaataccta gagtccaggc cagacatacg    420
gatctcaccc atctcagcct cagtaagttt gagtttcatg cggaagctat tttcctgctc    480
ccgagcgtac ccattgatga ccccaagaat gtccctcac atgatacggt acgacgcacg    540
aagcgggaga tagctcacat gcacgactac catgatttca ctctgcatct cgccttggca    600
gcgcaggatg gcaaggaggt agtagcgaaa ggatgggggc agagacaccc gctggcaggc    660
cctggggttc ccggccctcc gaccgaatgg acatttatct atgcgccccg caacgaagag    720
gagctcgcag ttgttgagat gatcattgaa gcatccattg ggtacatgac aaatgaccca    780
gccggtacag tcattgtt                                                   798

<210> SEQ ID NO 48
<211> LENGTH: 753
<212> TYPE: DNA
<213> ORGANISM: artificial
<220> FEATURE:
<223> OTHER INFORMATION: Humanized nucleic acid coding luciferase from
      Mycena chlorophos

<400> SEQUENCE: 48
atggtacagc tcacgcgaac ctcagggttt attgcagcgg ctgcgattgt tgccgccatc     60
gcgttcccgt ttattcgacg ggactatcag acttttctgc gaggggggccc ctcatatgcc    120 ccacagaata ttcgcggcta tatcattgtc ctggtcttgt ccctcttcag aggagaagaa    180
aagggtctgg ctatctatga gccgcttcca gagaaacgga cgtggttgcc agagttgcct    240
agacgggcgg gcgatagacc caaaactacc agccatataa tacaacgaca actcgaccaa    300
tatcccgacc cggacttcgt acttaaagca ttgaaagcaa ctgtaatacc gagagttcag    360
gcaaggcaca ctgataaaac ccatcttgca cttttccaagt ttgaattcca cgccgaggca    420
atcttcgtcc gaccagagat agccatagac gatccgaaac atatcccaag tcatgacaca    480
gtcagacgaa cgaaacggga gatagcccat atgcatgatt atcatgactg caccctgcac    540
cttgcgcttg cggcacagga cgcaaaacag gtcttgcaaa aaggatgggg acagagacac    600
ccccttgccg gacctggcat gccgggtccg cctactgaat ggacattcct ctacgccccg    660
agaactgagg aggaggtgaa agtggttgaa accatagtgg aggcgagtat agcttacatg    720
accaatgcag aaaaaccagt agaactcgta caa                                   753

<210> SEQ ID NO 49
<211> LENGTH: 738
<212> TYPE: DNA
<213> ORGANISM: artificial
<220> FEATURE:
```

<223> OTHER INFORMATION: Humanized nucleic acid coding luciferase from
      Mycena citricolor

<400> SEQUENCE: 49

| | | | | | | |
|---|---|---|---|---|---|---|
| atggcttatc | agttgacatg | gattcagact | cttgtattgg | gtgctctcgt | ggctatggct | 60 |
| gttgcatttc | cattcatcaa | aaaagattat | gagaccttcc | tcaagggcgg | cccttcatac | 120 |
| gcccccaga | atgtccgcgg | ttatattatc | gtactcgtcc | tcgcgctgtt | cagacaagaa | 180 |
| caattggggc | ttgagatata | tgaccgcatg | cccgaaaaac | gcaggtggct | cgctaacctc | 240 |
| cctcaacggg | aaggtccgcg | accgaaaacc | actagccata | tcattcagcg | ccagctctct | 300 |
| cagcataccg | accccgcctt | tggagcggct | tatctgaaag | acaccgtaat | cccgcgagtg | 360 |
| caggcgcggc | atgcagcgaa | cactcacata | gcgcgaagta | cgttcgaatt | cacgcagcg | 420 |
| gctatctttc | tcaacgcaga | cgtgccgttg | cccgaaggac | tgccagctag | cgaaacagtg | 480 |
| agacgaacca | aggagaaat | cgcgcacatg | cacgattacc | acgattttac | gctgcacctg | 540 |
| gcacttgcgg | cagcggacgg | aaagaggtg | gtcggcaaag | gatggggaca | gagacatcca | 600 |
| ctcgctggcc | ctggggtgcc | tggccctccg | aatgagtgga | cattcgtgta | cgctcccagg | 660 |
| aacgaggaag | agatgggcgt | agtagagcag | attgtagagg | ctgcaatcgg | ttacatgtca | 720 |
| aatgtccctg | ctctcgag | | | | | 738 |

<210> SEQ ID NO 50
<211> LENGTH: 783
<212> TYPE: DNA
<213> ORGANISM: artificial
<220> FEATURE:
<223> OTHER INFORMATION: Humanized nucleic acid coding luciferase from
      Omphalotus olearius

<400> SEQUENCE: 50

| | | | | | | |
|---|---|---|---|---|---|---|
| atgctcccgg | ctttcatata | taaaccgaga | ttggtcatta | cgtgcgtttt | tgttctcgct | 60 |
| agtgcattgg | cttttcccctt | cataagaaag | gactatcaga | ctttcctcga | agtcgggccg | 120 |
| tcttatgctc | ctcaaaacct | tcaagggtat | atcatagtct | gcgtattgtc | actcttcaga | 180 |
| caagagcaaa | aagatgtagc | catatacgat | agactccccg | agaaaagaag | gtggcttggt | 240 |
| gacctgccgt | tcagagaagg | gccgcgcccg | tctattacct | cccacattat | ccaacgccaa | 300 |
| agaacgcaac | ttgctgatgc | agagttcgca | acaaaggagt | tgattgggaa | gatcattccg | 360 |
| agggtgcagg | caaggcatac | aaataccact | ttcttgtcaa | cgagtaaatt | tgagtttcac | 420 |
| gcccaggcaa | tctttctgct | tccttcaatt | cccataaacg | atccacaaaa | tatcccaagt | 480 |
| cacgatacgg | tacggcgcac | gaagcgcgag | atcgcccaca | tgcatgatta | tcatgattgc | 540 |
| acgcttcact | tggctctcgc | cgcgcaggac | gggaaagagg | tgcttgagaa | ggggtggggt | 600 |
| cagcggcatc | cactcgccgg | gccaggtgtt | cccggtcccc | caaccgaatg | gacatttctc | 660 |
| tatgcgcccc | gctctgaaga | gaggtacgg | gtcgtggaaa | tgatagtcga | ggctagcgtg | 720 |
| gtttatatga | cgaatgatcc | tgcggacaag | attgtagagg | ccaccgtcca | gggcaccgaa | 780 |
| gag | | | | | | 783 |

<210> SEQ ID NO 51
<211> LENGTH: 747
<212> TYPE: DNA
<213> ORGANISM: artificial
<220> FEATURE:
<223> OTHER INFORMATION: Humanized nucleic acid coding luciferase from
      Panellus stipticus

<400> SEQUENCE: 51

```
atgaatataa atctgaaagc acttattggt gtctgtgcgg tactcatcac cgctgctgtc    60
tttccttttg tacggaaaga ctatcacacc tttttggagg gcggcccttc ctatgctcca   120
cagaacttgc agggctacat aatagtcctc gtcttgtcac tcttcagggg agaggagact   180
ggtttggaaa tttatgatcg cttgccagaa aagcggcgat ggctggaaga actgccagtg   240
cgggagggac cgcggcctaa gactacgagt cacatcatcc aacgccagct caaccagcac   300
gttgaccccg acttcggcat gaatagcttg aaaggctctg tgatacggag gcttcaatcc   360
cgccaccaag atataacgca gcttgctctt tccaagtttg agtttcacgc cgaagcaatt   420
tttctccggc ctgacgtcgc aatcaatgac cccaaacacg tgccatctca tgacactgtc   480
cgacgcacaa agagggagat cgctcacatg cacgactacc acgattacac ttgccatttg   540
gcccttgccg cccaagatgg caaacaagtg atagcgaagg gctgggtca aagacatccg   600
cttgctgggc ccggtatgcc tggacctcct accgagtgga ccttcctta tgccccacgc   660
aacgaagcag aggtgcaagt gctggaaact attattgagg caagtatagg atatatgagt   720
aacgcacctg ccctgggagg ttccgaa                                       747
```

<210> SEQ ID NO 52
<211> LENGTH: 60
<212> TYPE: DNA
<213> ORGANISM: artificial
<220> FEATURE:
<223> OTHER INFORMATION: Nucleic acid coding site of transcription
      initiation and His-tag

<400> SEQUENCE: 52

```
atggctagca tgactggtgg acagcaaatg ggtcgcggat cccaccacca ccaccaccac    60
```

<210> SEQ ID NO 53
<211> LENGTH: 20
<212> TYPE: PRT
<213> ORGANISM: artificial
<220> FEATURE:
<223> OTHER INFORMATION: N-terminal amino acid sequence comprising
      His-tag

<400> SEQUENCE: 53

```
Met Ala Ser Met Thr Gly Gly Gln Gln Met Gly Arg Gly Ser His His
1               5                   10                  15
His His His His
            20
```

<210> SEQ ID NO 54
<211> LENGTH: 801
<212> TYPE: DNA
<213> ORGANISM: artificial
<220> FEATURE:
<223> OTHER INFORMATION: Nucleic acid coding the luciferase from
      Neonothopanus nambi, optimised fro expression in Physcomitrella
      patens

<400> SEQUENCE: 54

```
atgaggataa atatctcttt gtctagtctc tttgagagac tgagcaaatt gtcatcccga    60
tccatcgcaa ttacctgcgg cgtagtcttg gcaagtgcaa tagcattccc aattatccga   120
agagactatc aaacgttcct tgaagtcggt ccgagctatg ccccacagaa cttccgaggc   180
tatatcatcg tttgtgtctt gtcactttt aggcaagagc agaaagggtt ggcaatctat   240
gacaggcttc cagaaaagag gcgttggctt gccgacttgc cgtttcgtga aggacgagg   300
```

```
ccatccataa cctcccacat tatacagcgt cagcgtactc agctggtaga tcaagagttt      360
gcaaccagag aacttatcga taaggtgatc ccacgtgtgc aagcaagaca cacagacaaa      420
acttttctca gtacgtcaaa atttgagttt catgcaaagg ccatcttcct tctcccctct      480
atccctatta atgatcctct taacattccc tcacacgata cggtaagaag aaccaagcgt      540
gagatcgctc acatgcatga ttaccatgat tgcactctgc acttggctct tgctgctcag      600
gatggtaagg aagttttgaa gaaggggtgg ggccagcgtc acccactggc cggaccagga      660
gtcccaggcc ctcctactga gtggaccttc ctttacgcac caaggaacga agaggaggcc      720
agagttgtcg agatgatagt cgaagctagt attggctaca tgactaacga tcctgctggt      780
aagattgtcg aaaatgccaa g                                                801
```